United States Patent
Vardon et al.

(10) Patent No.: US 11,420,912 B2
(45) Date of Patent: Aug. 23, 2022

(54) FUELS AND METHODS OF MAKING THE SAME

(71) Applicant: Alliance for Sustainable Energy, LLC, Golden, CO (US)

(72) Inventors: Derek Richard Vardon, Lakewood, CO (US); Xiangchen Huo, Golden, CO (US); Nabila Huq, Golden, CO (US); Huong Thi Thanh Nguyen, Arvada, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 17/121,336

(22) Filed: Dec. 14, 2020

(65) Prior Publication Data

US 2021/0188734 A1    Jun. 24, 2021

Related U.S. Application Data

(60) Provisional application No. 62/947,580, filed on Dec. 13, 2019, provisional application No. 63/033,331, filed on Jun. 2, 2020.

(51) Int. Cl.
| | |
|---|---|
| *C07C 1/22* | (2006.01) |
| *C12P 7/26* | (2006.01) |
| *C07C 45/41* | (2006.01) |
| *C07C 45/68* | (2006.01) |
| *C07C 9/15* | (2006.01) |

(Continued)

(52) U.S. Cl.
CPC ............. *C07C 1/22* (2013.01); *C07C 9/15* (2013.01); *C07C 9/16* (2013.01); *C07C 45/41* (2013.01); *C07C 45/68* (2013.01); *C10L 1/04* (2013.01); *C10L 2200/0469* (2013.01); *C10L 2270/04* (2013.01)

(58) Field of Classification Search
None
See application file for complete search history.

(56) References Cited

U.S. PATENT DOCUMENTS

| | | |
|---|---|---|
| 9,828,354 B2 | 11/2017 | Chen et al. |
| 10,207,961 B2 | 2/2019 | Sreekumar |
| 2007/0135316 A1 | 6/2007 | Koivusalmi |

(Continued)

FOREIGN PATENT DOCUMENTS

| | | |
|---|---|---|
| WO | 2006/084285 A2 | 8/2006 |
| WO | 2008152200 A1 | 12/2008 |

(Continued)

OTHER PUBLICATIONS

English translation of WO 2011/115394 A2 Abstract to Chung, Y.M. et al., published Sep. 22, 2011, 1 page.

(Continued)

*Primary Examiner* — Philip Y Louie
(74) *Attorney, Agent, or Firm* — Michael A. McIntyre

(57) ABSTRACT

The present disclosure relates to a method that includes a first treating of a first mixture that includes a carboxylic acid having between 2 and 12 carbon atoms, inclusively, to form a second mixture that includes a ketone having between 2 and 25 carbon atoms, inclusively, and a second treating of at least a first portion of the second mixture to form a first product that includes a paraffin having 8 or more carbon atoms.

14 Claims, 25 Drawing Sheets

(51) Int. Cl.
*C07C 9/16* (2006.01)
*C10L 1/04* (2006.01)

(56) References Cited

U.S. PATENT DOCUMENTS

| | | | |
|---|---|---|---|
| 2011/0150813 A1 | 6/2011 | Desenne et al. | |
| 2012/0198760 A1* | 8/2012 | Blommel | C10G 3/50 |
| | | | 44/437 |
| 2013/0017590 A1* | 1/2013 | Chung | C10M 105/04 |
| | | | 435/167 |
| 2014/0073826 A1* | 3/2014 | Miller | C10L 1/04 |
| | | | 585/256 |
| 2014/0335586 A1 | 11/2014 | Zhang | |
| 2017/0080672 A1 | 3/2017 | Amano | |
| 2018/0086677 A1 | 3/2018 | Myllyoja et al. | |
| 2019/0218466 A1* | 7/2019 | Slade | C10G 3/50 |

FOREIGN PATENT DOCUMENTS

| | | |
|---|---|---|
| WO | 2015148412 A2 | 10/2015 |
| WO | 2018/001694 A1 | 1/2018 |

OTHER PUBLICATIONS

Alonso, D.M. et al., "Production of liquid hydrocarbon transportation fuels by oligomerization of biomass-derived C9 alkenes," RSC Green Chemistry, vol. 12, 2010, 8 pages.
Amer, M. et al., "Low carbon strategies for sustainable bio-alkane gas production and renewable energy," RSC Energy & Environmental Science, vol. 13, 2020, 14 pages.
Atasoy, M. et al., "Bio-based volatile fatty acid production and recovery from waste streams: Current status and future challenges," Elsevier Bioresource Technology, vol. 268, 2018, 14 pages.
Balakrishnan, M. et al., "Novel pathways for fuels and lubricants from biomass optimized using life-cycle greenhouse gas assessment," PNAS, vol. 112, No. 25, Jun. 23, 2015, 6 pages.
Bhatt, A. H. et al., "Value Proposition of Untapped Wet Wastes: Carboxylic Acid Production through Anaerobic Digestion," iScience, vol. 23, Jun. 26, 2020, 29 pages.
Ciesielski, P.N. et al., "Advances in Multiscale Modeling of Lignocellulosic Biomass," ACS Sustainable Chemistry & Engineering, vol. 8, 2020, 20 pages.
Fufachev, E. et al., "Tandem catalytic aromatization of volatile fatty acids," RSC Green Chemistry, vol. 22, 2020, 10 pages.
Gaertner, C.A., "Ketonization Reactions of Carboxylic Acids and Esters over Ceria-Zirconia as Biomass-Upgrading Processes," ACS, Ind. Eng. Chem. Res. vol. 49, No. 13, 2010, 7 pages.
Glinski, M. et al., "Catalytic Ketonization of Carboxylic Acids Synthesis of Saturated and Unsaturated Ketones," React. Kinet. Catal. Lett., vol. 69, No. 1, 2000, 6 pages.
Hafenstine, G.R. et al., "Single-phase catalysis for reductive etherification of diesel bioblendstocks," RSC Green Chemistry, vol. 22, 2020, 10 pages.
Harvey, B.G. et al., "1-Hexene: a renewable C6 platform for full-performance jet and diesel fuels," RSC Green Chemistry, vol. 16, 2014, 7 pages.
Holtzapple, M.T. et al., "Biomass Conversion to Mixed Alcohol Fuels Using the MixAlco Process," Applied Biochemistry and Biotechnology, vol. 77-79, 1999, 23 pages.
Huo, X. et al., "Tailoring diesel bioblendstock from integrated catalytic upgrading of carboxylic acids: a "fuel property first" approach," RSC Green Chemistry, vol. 21, 2019, 5 pages.
Huq, N.A. et al., "Performance-advantaged ether diesel bioblendstock production by a priori design," PNAS, vol. 116, No. 52, Dec. 26, 2019, 10 pages.
Jahromi, H. et al., "Hydrodeoxygenation of Aqueous-Phase Catalytic Pyrolysis Oil to Liquid Hydrocarbons Using Multifunctional Nickel Catalyst," Ind. Eng. Chem. Res., vol. 57, 2018, 12 pages.
Jiang, B. et al., "Ce/MgAl mixed oxides derived from hydrotalcite LDH precursors as highly efficient catalysts for ketonization of carboxylic acid," RSC Catalysis Science & Technology, DOI: 10.1039/c9cy01323g, 2019, 10 pages.
Pham, T.N. et al., "Ketonization of Carboxylic Acids: Mechanisms, Catalysts, and Implications for Biomass Conversion," ACS Catalysis, vol. 3, 2013, 18 pages.
Pham, T.N. et al., "Reaction kinetics and mechanism of ketonization of aliphatic carboxylic acids with different carbon chain lengths over Ru/TiO2 catalyst," Elsevier Journal of Catalysis, vol. 314, 2014, 10 pages.
Pacchioni, G., "Ketonization of Carboxylic Acids in Biomass Conversion over TiO2 and ZrO2 Surfaces: A DFT Perspective," ACS Catalysis, vol. 4, 2014, 15 pages.
Phung, T.K. et al., "Catalytic pyrolysis of vegetable oils to biofuels: Catalyst functionalities and the role of ketonization on the oxygenate paths," Elsevier Fuel Processing Technology, vol. 140, 2015, 6 pages.
Rabaev, M. et al., "Improvement of hydrothermal stability of Pt/SAPO-11 catalyst in hydrodeoxygenation-isomerization-aromatization of vegetable oil," Elsevier Journal of Catalysis, vol. 332, 2015, 13 pages.
Ramos, R. et al., "Towards understanding the hydrodeoxygenation pathways of furfural-acetone aldol condensation products over supported Pt catalysts," RSC Catalysis Science & Technology, vol. 6, 2016, 13 pages.
Sacia, E.R. et al., "Highly Selective Condensation of Biomass-Derived Methyl Ketones as a Source of Aviation Fuel," ChemSusChem, vol. 8, 2015, 11 pages.
Shylesh, S. et al., "Integrated catalytic sequences for catalytic upgrading of bio-derived carboxylic acids to fuels, lubricants and chemical feedstocks," RSC Sustainable Energy & Fuels, vol. 1, 2017, 5 pages.
Shylesh, S. et al., "Experimental and Computational Studies of Carbon-Carbon Bond Formation via Ketonization and Aldol Condensation over Site-Isolated Zirconium Catalysts," ACS Catalysis, vol. 10, 2020, 14 pages.
Takanabe, K. et al., "Catalyst deactivation during steam reforming of acetic acid over Pt/ZrO2," Elsevier Chemical Engineering Journal, vol. 120, 2006, 5 pages.
Yang, X. et al., "Hydrodeoxygenation (HDO) of Biomass Derived Ketones Using Supported Transition Metals in a Continuous Reactor," ACS Sustainable Chemistry & Engineering, vol. 7, 2019, 10 pages.
Milbrandt, A. et al., "Wet waste-to-energy resources in the United States," Elsevier Resources, Conservation Recycling, vol. 137, 2018, 16 pages.
Badgett, A. et al., "Economic analysis of wet waste-to-energy resources in the United States," Elsevier Energy, vol. 176, 2019, 11 pages.
Davis, R. et al., "Process Design and Economics for the Conversion of Lignocellulosic Biomass to Hydrocarbon Fuels and Coproducts: 2018 Biochemical Design Case Update," NREL Technical Report NREL/TP-5100-71949; Nov. 2018; 147 pages.
International Search Report and Written Opinion for International (PCT) Application No. PCT/US21/61938, dated Mar. 16, 2022, pp. 1-8.

* cited by examiner

1

2

Theoretical C Yield (%)

3

FUELS AND METHODS OF MAKING THE SAME

CROSS-REFERENCE TO RELATED APPLICATIONS

This application claims priority from U.S. Provisional Patent Application Nos. 62/947,580 and 63/033,331 filed on Dec. 13, 2019 and Jun. 2, 2020, respectively, the contents of which are incorporated herein by reference in their entirety.

CONTRACTUAL ORIGIN

This invention was made with government support under Contract No. DE-AC36-08GO28308 awarded by the Department of Energy. The government has certain rights in the invention.

BACKGROUND

Typical renewable liquid fuels rely on alcohol carbon coupling chemistry to produce predominantly iso-paraffin hydrocarbons that limit the volumetric energy. In addition, these iso-paraffin-rich fuels lack cycloparaffins which can provide sufficient polymer seal swelling for aviation fuel system infrastructure compatibility if used for this application. For these and other reasons, there remains a need for advanced methods for producing bioderived liquid fuels, such as aviation fuels and diesel fuels, having improved volumetric energy and other improved performance metrics.

SUMMARY

An aspect of the present disclosure is a method that includes a first treating of a first mixture that includes a carboxylic acid having between 2 and 12 carbon atoms, inclusively, to form a second mixture that includes a ketone having between 2 and 25 carbon atoms, inclusively, and a second treating of at least a first portion of the second mixture to form a first product that includes a paraffin having 8 or more carbon atoms.

In some embodiments of the present disclosure, the carboxylic acid may have between 2 and 8 carbon atoms, inclusively. In some embodiments of the present disclosure, the ketone may have between 3 and 15 carbon atoms, inclusively. In some embodiments of the present disclosure, the first treating may include the reaction

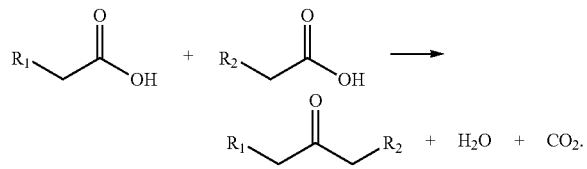

where $R_1$ includes between 1 and 11 carbon atoms, and $R_2$ includes between 1 and 11 carbon atoms.

In some embodiments of the present disclosure, the second treating may result in the deoxygenation of at least a portion of the ketone to form the paraffin. In some embodiments of the present disclosure, the paraffin may include a normal paraffin. In some embodiments of the present disclosure, the normal paraffin may have between 8 and 15 carbon atoms, inclusively. In some embodiments of the present disclosure, at least a portion of the carboxylic acid may be bioderived as determined by ASTM-D6866. In some embodiments of the present disclosure, the method may further include, prior to the second treating, separating the second mixture to form the first portion of the second mixture and a second portion of the second mixture, where the first portion includes a ketone having 8 or more carbon atoms, and the second portion includes a ketone having less than 8 carbon atoms.

In some embodiments of the present disclosure, the method may further include, a third treating of the second portion to form a third mixture than includes an intermediate, where the third treating includes the reaction

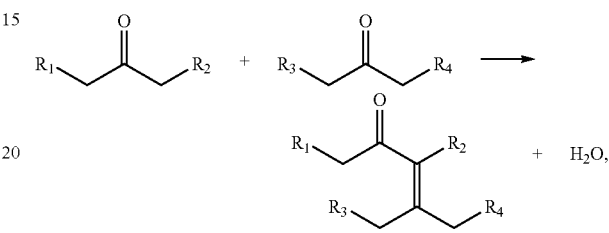

resulting in the forming of the intermediate and water, $R_1$ includes between 1 and 6 carbon atoms, inclusively, $R_2$ includes between 1 and 6 carbon atoms, inclusively, $R_3$ includes between 1 and 6 carbon atoms, inclusively, $R_4$ includes between 1 and 6 carbon atoms, inclusively, and the intermediate has a form that includes at least one of a linear molecule, a branched molecule, and/or a cyclic molecule.

In some embodiments of the present disclosure, the method may further include a fourth treating of at least a portion of the third mixture to form a second product that includes a paraffin having 10 or more carbon atom. In some embodiments of the present disclosure, the paraffin of the second product may include a branched paraffin. In some embodiments of the present disclosure, the fourth treating may result in the deoxy enation of at least a portion of the intermediate to form the paraffin. In some embodiments of the present disclosure, the method may further include mixing at least a portion of the first product with at least a portion of the second product to form a blended product. In some embodiments of the present disclosure, the method may further include co-feeding the second mixture and the third mixture with at least one of a fat, an oil, and/or a grease to a deoxygenation step.

An aspect of the present disclosure is a method that includes a first reacting of a secondary alcohol resulting in the conversion of at least a portion of the secondary alcohol to an alkene, a second reacting of the alkene resulting in the conversion of at least a portion of the alkene to a branched alkene, and a third reacting of the branched alkene resulting the conversion of at least a portion of the branched alkene to a branched paraffin.

An aspect of the present disclosure is a composition for a liquid fuel, where the composition includes a normal paraffin having more than 7 carbon atoms, where the normal paraffin is bioderived, and the composition is characterized by at least one of a physical property and/or a performance metric that is improved compared to the same physical property and/or the same performance metric of a reference petroleum-based liquid fuel. In some embodiments of the present disclosure, the reference petroleum-based liquid fuel may include diesel fuel or jet fuel.

An aspect of the present disclosure is composition for a liquid fuel, where the composition includes an iso-paraffin having more than 7 carbon atoms, where the iso-paraffin is bioderived. In some embodiments of the present disclosure, the iso-paraffin may have more than 9 carbon atoms.

BRIEF DESCRIPTION OF THE DRAWINGS

Some embodiments of the present disclosure are illustrated in the referenced figures of the drawings. It is intended that the embodiments and figures disclosed herein are to be considered illustrative rather than limiting.

Figure 1:
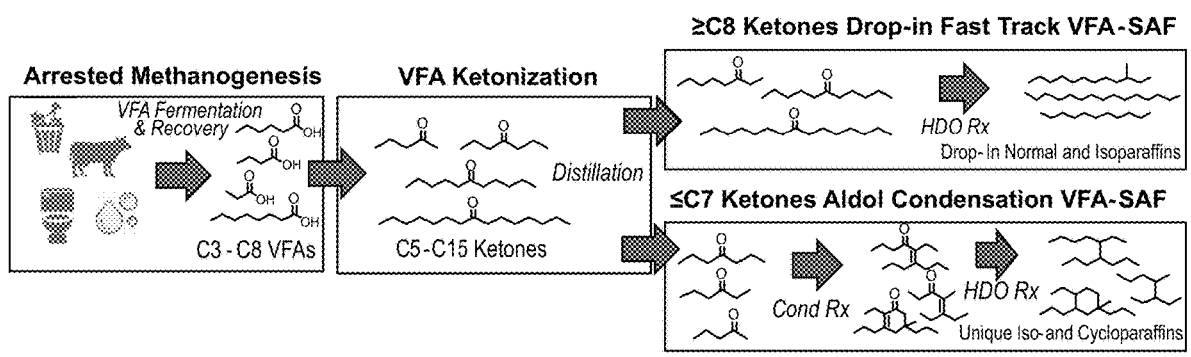
FIG. 1 illustrates a method for converting acids, for example carboxylic acids, to fuels and/or fuel blendstocks that include paraffins, e.g. normal paraffins and/or iso-paraffins, according to some embodiments of the present disclosure.

| REFERENC NUMERALS | |
|---|---|
| 200 | system |
| 205 | carboxylic acid stream |
| 210 | ketonization reactor |
| 212 | intermediate ketone stream |
| 220 | separating unit |
| 222 | first ketone stream (8 or more carbon atoms) |
| 224 | second ketone stream (less than 8 carbon atoms) |
| 230 | first hydrodeoxygenation reactor |
| 232 | normal paraffin stream (i.e. straight chained product) |
| 240 | aldol condensation reactor |
| 242 | oxygenated iso-olefin stream |
| 250 | second hydrodeoxygenation reactor |
| 252 | first iso-paraffin stream (i.e. branched product) |
| 255 | alcohol stream |
| 260 | dehydration reactor |
| 262 | normal olefin stream |
| 270 | oligomerization reactor |
| 272 | iso-olefin stream |
| 280 | hydrogenation reactor |
| 282 | second iso-paraffin stream (i.e. branched product) |
| 300 | method |
| 305 | first mixture (carboxylic acids) |
| 310 | first treating (ketonization) |
| 315 | second mixture (ketones) |
| 320 | separating |
| 322 | first portion of second mixture (C8 and higher) |
| 324 | second portion of second mixture (<C8) |
| 330 | second treating (deoxygenation) |
| 332 | first product (normal paraffins) |
| 340 | third treating (aldol condensation) |
| 342 | third mixture (oxygenated iso-olefins) |
| 350 | fourth treating (deoxygenation) |
| 352 | second product (iso-paraffins) |
| 355 | fourth mixture (alcohols) |
| 360 | first reacting (dehydration) |
| 362 | fifth mixture (normal olefins) |
| 370 | second reacting (oligomerization) |
| 372 | sixth mixture (iso-olefins) |
| 380 | third reacting (hydrogenation) |
| 382 | third product (iso-paraffins) |

DETAILED DESCRIPTION

The present disclosure may address one or more of the problems and deficiencies of the prior art discussed above. However, it is contemplated that some embodiments as disclosed herein may prove useful in addressing other problems and deficiencies in a number of technical areas. Therefore, the embodiments described herein should not necessarily be construed as limited to addressing any of the particular problems or deficiencies discussed herein.

References in the specification to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein the term "substantially" is used to indicate that exact values are not necessarily attainable. By way of example, one of ordinary skill in the art will understand that in some chemical reactions 100% conversion of a reactant is possible, yet unlikely. Most of a reactant may be converted to a product and conversion of the reactant may asymptotically approach 100% conversion. So, although from a practical perspective 100% of the reactant is converted, from a technical perspective, a small and sometimes difficult to define amount remains. For this example of a chemical reactant, that amount may be relatively easily defined by the detection limits of the instrument used to test for it. However, in many cases, this amount may not be easily defined, hence the use of the term "substantially". In some embodiments of the present invention, the term "substantially" is defined as approaching a specific numeric value or target to within 20%, 15%, 10%, 5%, or within 1% of the value or target. In further embodiments of the present invention, the term "substantially" is defined as approaching a specific numeric value or target to within 1%, 0.9%, 0.8%, 0.7%, 0.6%, 0.5%, 0.4%, 0.3%, 0.2%, or 0.1% of the value or target.

As used herein, the term "about" is used to indicate that exact values are not necessarily attainable. Therefore, the term "about" is used to indicate this uncertainty limit. In some embodiments of the present invention, the term "about" is used to indicate an uncertainty limit of less than or equal to ±20%, ±15%, ±10%, ±5%, or ±1% of a specific numeric value or target. In some embodiments of the present invention, the term "about" is used to indicate an uncertainty limit of less than or equal to ±1%, ±0.9%, ±0.8%, ±0.7%, ±0.6%, ±0.5%, ±0.4%, ±0.3%, ±0.2%, or ±0.1% of a specific numeric value or target.

The present disclosure relates to methods for producing unique, bioderived fuels, including aviation fuels such as jet fuel. In some embodiments of the present disclosure, a tunable mixture of volatile fatty acids (VFAs) may be used as the feedstock, which are processed via ketone carbon coupling chemistry to produce a controllable, targeted mixture of normal paraffin hydrocarbons (i.e. straight-chained alkanes), iso-paraffin hydrocarbons (i.e. branched alkanes), cycloparaffin hydrocarbons, and/or aromatic hydrocarbons. In some embodiments of the present disclosure, at least one of a ketonization step, a condensation step, an aldol condensation step, and/or a hydrodeoxygenation (HDO) step may be used to convert VFAs to one or more high value fuels. Among other things, such mixtures may be used for performance advantaged aviation fuels. In some embodiments of the present disclosure, the use of cycloparaffins may help reduce the aromatic content when blended into petrol aviation fuel, resulting in at least one of lower sooting, improved thermal stability, and/or other improved physical properties and/or performance metrics.

The present disclosure also relates to the conversion of secondary alcohols to iso-paraffins, which may also be used as fuels and/or fuel blendstocks. In some embodiments of the present disclosure, alcohol-derived iso-paraffins may be used individually as a fuel and/or blendstock. In some embodiments of the present disclosure, alcohol-derived iso-paraffins may be blended with VFA-derived paraffins (e.g. normal paraffins and/or iso-paraffins) to be subsequently used as a fuel and/or blendstock.

Therefore, among other things, the present disclosure relates to systems and/or methods for the up-grading of bioderived materials, e.g. wet waste volatile fatty acids (VFAs) and/or alcohols, to useful fuels and/or fuel blendstocks. FIG. 1 illustrates a system 100 for producing liquid fuels, according to some embodiments of the present disclosure. Currently, anaerobic digestion to produce biogas is a leading technology to recover energy from wet wastes. However, as described herein, anaerobic digestion of wet waste can be arrested prior to methanogenesis to generate VFAs, which may be used as precursors for biofuels and biobased chemicals. VFA production by arrested methanogenesis offers the potential to utilize existing biogas infrastructure and a wide variety of wet waste feedstocks. As shown herein, in some embodiments of the present disclosure, VFAs may be catalytically upgraded to bioderived fuels through carbon coupling and deoxygenation chemistries. Depending on their chain length, VFAs may be converted into normal paraffins similar and/or identical to those found in petroleum and/or undergo an additional carbon coupling step (via aldol condensation, dehydration, and/or oligomerization) to generate iso-paraffin hydrocarbons, cycloparaffin hydrocarbons, and/or aromatic hydrocarbons with molecular structures distinct from those typically found fossil-derived jet fuels, with examples illustrated in FIG. 1.

As shown herein, a ketonization reaction may be performed on one or more VFAs, resulting in the elongation of the carbon backbone of the VFAs and conversion of the VFAs to ketones. A generalized ketonization reaction is shown in Reaction 1 below, according to some embodiments of the present disclosure.

Reaction 1

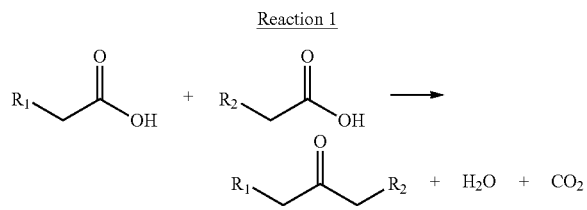

As shown in Reaction 1, two VFAs may react to produce a single ketone that is one carbon shorter than the sum of both carboxylic acids and resulting in the removal of oxygen in the form of water and carbon dioxide. In some embodiments of the present disclosure, $R_1$ may include between 1 and 11 carbon atoms, inclusively, and $R_2$ may include between 1 and 11 carbon atoms, inclusively.

In some embodiments of the present disclosure, $R_1$ and $R_2$ may be the same functional group, or $R_1$ and $R_2$ may be different functional groups. Reaction 1 may include a first mixture that includes at least one carboxylic acid having between 2 and 12 carbon atoms to form a second mixture that includes at least one ketone having between 2 and 25 carbon atoms. In some embodiments of the present disclosure, $R_1$ may include an alkyl group having between 1 and 11 carbon atoms, inclusively. In some embodiments of the present disclosure, $R_2$ may include an alkyl group having between 1 and 11 carbon atoms, inclusively. The VFAs chain length may be either a straight hydrocarbon chain (normal, n-) and/or a branched hydrocarbon chain (iso-). Examples of VFAs include acetic acid, propionic acid, n-butyric acid, iso-butyric acid, n-pentanoic acid, iso-pentanoic acid, n-hexanoic acid, n-heptanoic acid, and n-octanoic acid.

In some embodiments of the present disclosure, following ketonization, ketones having 8 or more carbon atoms may be reacted with hydrogen ($H_2$) to undergo hydrodeoxygenation (see the top right of FIG. 1) to produce normal paraffins. This reaction is illustrated below as Reaction 2.

Reaction 2

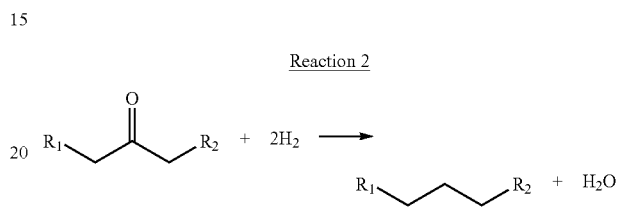

In comparison, in some embodiments of the present disclosure, ketones having less than 8 carbon atoms may undergo a second carbon coupling step prior to hydrodeoxygenation, via an aldol condensation reaction, to produce oxygenated branched olefins having between 3 and 30 carbon atoms (see the bottom right of FIG. 1). Reaction 3 illustrates an aldol condensation reaction, according to some embodiments of the present disclosure. This reaction may also be referred to as an oligomerization reaction, as the reaction of the two ketones results in the formation of a larger molecular weight oligomer.

Reaction 3

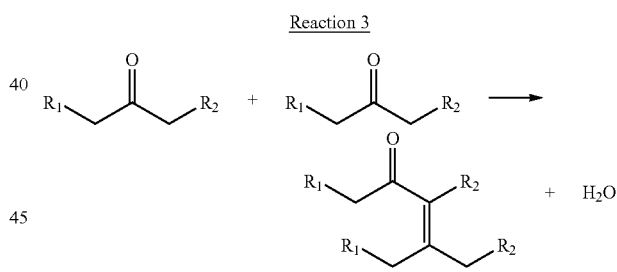

Thus, referring to Reaction 3, in some embodiments of the present disclosure, ketones with $R_1$ and/or $R_2$ functional groups having three or less carbon atoms may be reacted with similar sized ketones to produce branched, oxygenated olefins having larger molecular weights. In some embodiments of the present disclosure, $R_1$ and/or $R_2$ may include an alkyl group having between 1 and 3 carbon atoms, inclusively. Although the example shown in Reaction 3 illustrates two identical ketones reacting with each other, this is for exemplary purposes. Different ketones, having different $R_1$ and $R_2$ groups may react to form the branched product shown in Reaction 3, according to some embodiments of the present disclosure.

Following the aldol condensation reaction, the resultant branched, oxygenated olefins may be reacted with hydrogen ($H_2$) to undergo hydrodeoxygenation (see the bottom right of FIG. 1) to produce deoxygenated branched saturated hydrocarbons; i.e. iso-paraffins. This is illustrated below as Reaction 4.

Reaction 4

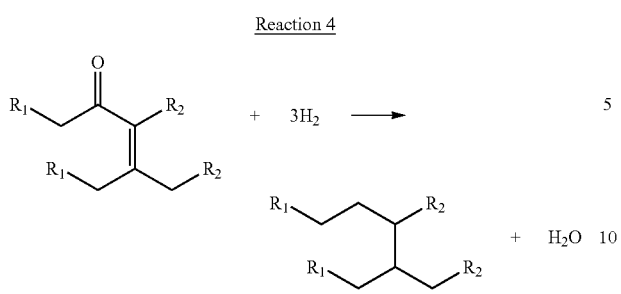

Ketone carbon coupling can take place by various pathways including aldol condensation chemistry, as well as ketone reduction to alcohols for further dehydration and oligomerization, which is discussed in more detail below. As shown herein, aldol condensation of central ketones can generate structurally unique iso-paraffins, having significantly lower freezing points, making them uniquely suitable for jet fuel applications, due to the high degree of branching of the iso-paraffins, as well as reduce the intrinsic sooting tendency relative to aromatic hydrocarbons by over two-fold by interruption of the carbon chain length. In some embodiments of the present disclosure, the reactions described above enable one to synthesize paraffins and/or paraffin mixtures having specific targeted physical properties, such as vapor pressure and/or flashpoint temperatures. Referring again to Reaction 4, only two functional groups are shown, $R_1$ and $R_2$. This is for illustrative purposes only, and both reactants and products of Reaction 4 may include functional groups that are the same or different; e.g. $R_1=R_2$, $R_1 \neq R_2$, the reactant and product include three different functional groups, and/or the reactant and product include four different functional groups.

Normal paraffins produced from VFAs (see the top right of FIG. 1) can provide fungible hydrocarbons similar to and/or identical to those in petroleum that offer a near-term path to, among other things, sustainable aviation fuels (SAFs). In the United States, new SAF conversion routes must complete a rigorous qualification process to ensure fuel safety and operability overseen by ASTM International, the Federal Aviation Administration, and aviation original equipment manufacturers (OEMs). There are currently five ASTM approved routes for SAF that include alcohol-to-jet, Fischer-Tropsch, and hydrotreated esters and fatty acids (HEFA). Historically, ASTM qualification can require jet fuel volumes of over 100,000 gallons in order to pass a four-tiered screening process and two OEM review stage gates that may take place over a period of 3 to 7 years. To help reduce this barrier, in January 2020 ASTM approved a new "Fast Track" qualification process for SAF routes that produce hydrocarbons structurally comparable to those in petroleum jet with a 10 vol % blend limit. "Fast Track" eliminates two tiers of testing and facilitates approval with under 1,000 gal of fuel and within the timeframe of 1 to 2 years.

In contrast, iso-paraffins derived from, for example, aldol condensation and hydrodeoxygenation (Reactions 3 and 4) can offer complementary fuel properties to increase the renewable blend content of VFA-SAF blends, but the unique chemical structures do not qualify for "Fast Track" approval. To accelerate the approval of SAF routes that produce molecules distinct from petroleum jet, small-volume fuel tests and predictive tools are being developed for the most critical bulk properties, which screen for potentially deleterious engine operability effects, e.g., lean blowout, cold ignition, and altitude relight. These tests, referred to as Tier α and β prescreening, evaluate SAF candidates for established ASTM D7566 properties, as well as novel properties observed to be important through the National Jet Fuels Combustion Program (NJFCP) (see Table 1). New properties include surface tension and derived cetane number (DCN), which impact ignition and lean blowout propensity, respectively. At less than one mL of test volume, Tier α can utilize GC and GCxGC method data to predict all critical properties. With between 50 mL and 150 mL of neat material (depending on the CN measurement method used), Tier β test methods can measure the critical unblended operability properties. In terms of emissions, low-volume sooting tendency measurement methods have been developed that require <1 mL of fuel versus the 10 mL required to measure smoke point. Combined, these new methods allow for rapid evaluation of developing bioderived fuels (e.g. SAF) and/or bioderived fuel blendstocks and/or methods/systems for making these materials.

TABLE 1

Volume required and method for measuring associated properties for Tier α, Tier β, and additional measurements

| Evaluation Category | Measured Property | Predicted Property | Test Volume |
|---|---|---|---|
| Tier α | Hydrocarbon Type Analysis (GC × GC) Simulated Distillation (ASTM D2887) | nHOC, Density, Surface tension, Freeze point, Viscosity, DCN, Flash point | ~1 mL |
| Tier β | Density (ASTM D4052) Viscosity (ASTM D7042) Surface tension (ASTM D1331A) Freeze point (ASTM D5972) Flash point (ASTM D3828A) | nHOC | ~10 mL |
| | ICN (ASTM D8183) | | ~40 mL (140 mL with conventional DCN ASTM D6890) |
| Additional Measurements | Net Heat of Combustion (D240 calculation) | — | — |
| | HOC (ASTM D4809) | | ~6 mL |
| | % H (LECO CHN 628 elemental analyzer) | | ~0.6 mL |
| | Acid Content (ASTM D664) | | ~5 mL |
| | Nitrogen Quant. (ASTM D4629) | | ~5 mL |
| | Yield sooting index (published method(16)) | | ~0.5 mL |

To advance the technology and fuel readiness level of VFA-SAF, as well as other materials, the present disclosure describes work that evaluates the production of drop-in normal paraffins and structurally unique iso-paraffins from food-waste derived VFAs. As shown herein, VFAs were biologically produced from food waste and recovered neat by an industry partner, Earth Energy Renewables. A simplified kinetic model was then developed for mixed VFA ketonization to determine the ketone carbon chain length distribution suitable for SAF production by each conversion route, with model results compared to experiments with biogenic VFAs. VFA ketonization was assessed for >100 hours of continuous time-on-stream operation, with trace impurities characterized within the incoming biogenic VFA feed. Catalyst regeneration was evaluated for coke and impurity removal, as well as to fresh and regenerated catalyst activity. Following VFA ketonization, ≥$C_8$ ketones were processed by direct hydrodeoxygenation to generate predominantly normal paraffins suitable for 10% blend testing for ASTM Fast Track, hereon referred to as "Fast Track VFA-SAF." In parallel, VFA-derived ketones ≤$C_7$ were processed via aldol condensation and hydrodeoxygenation to produce predominantly iso-paraffin hydrocarbons for Tier α and Tier β prescreening, hereon referred to as "Aldol Condensation VFA-SAF." Higher blends with both VFA-SAF fractions were examined to increase the renewable carbon content and to reduce soot formation, while still meeting fuel property specifications.

Further, as mentioned above, in some embodiments of the present disclosure, ketones may be reduced to alcohols for further dehydration and oligomerization to produce iso-paraffins. This series of four reactions (A, B, C, and D) is illustrated in Reaction 5 below.

Reaction 5

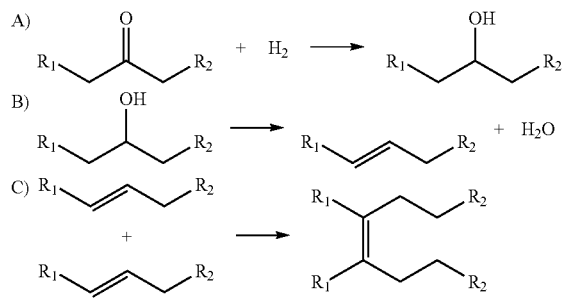

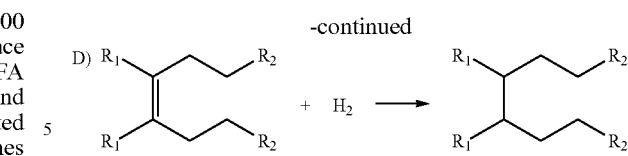

As shown in Reaction 5, in some embodiments of the present disclosure, a ketone may be reacted with hydrogen to form a secondary alcohol (Step A). The secondary alcohol may be subsequently reacted to form an alkene(s), via dehydration (Step B). Subsequently, the alkene may be reacted (Step C) with itself and/or another alkene (not shown) to produce a larger molecular weight molecule, e.g. an oligomer, branched alkene (i.e. iso-olefin). Finally, the iso-paraffin may be hydrogenated to produce the targeted iso-paraffin (Step D). In some embodiments of the present disclosure, one or more of Steps A, B, C, and D of Reaction 5 may be performed essentially in series, in separate reactors. In some embodiments of the present disclosure, two or more of Steps A, B, C, D of Reaction 5 may be performed essentially simultaneously, in a single reactor. In some embodiments of the present disclosure, $R_1$ and/or $R_2$ may include an alkyl group having between 1 and 10 carbon atoms, inclusively. Reaction 6 illustrates a specific example Steps B, C, and D of Reaction 5, where both $R_1$ and $R_2$ are both propyl groups, according to some embodiments of the present disclosure. Referring again to Reaction 5, only two functional groups are shown, $R_1$ and $R_2$. This is for illustrative purposes only, and both reactants and products of Reaction 5 may include functional groups that are the same or different; e.g. $R_1$=$R_2$, $R_1$≠$R_2$, the reactants and products include three different functional groups, and/or the reactants and products include four different functional groups.

Reaction 6

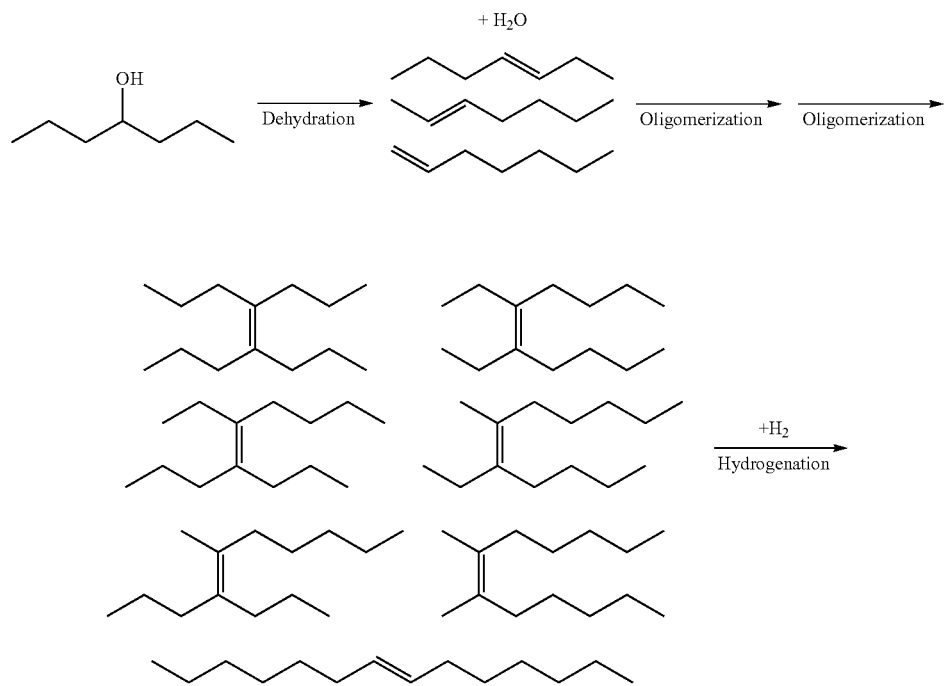

-continued

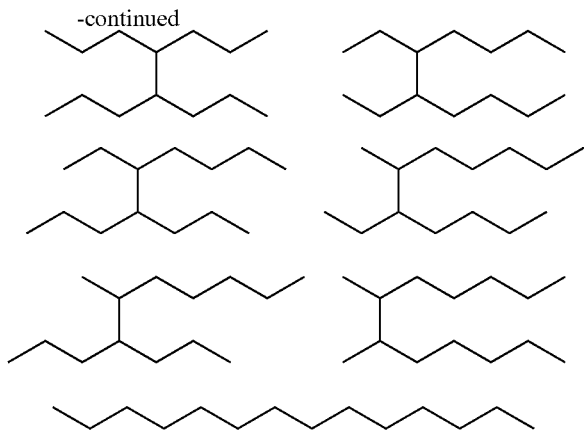

Figure 2:
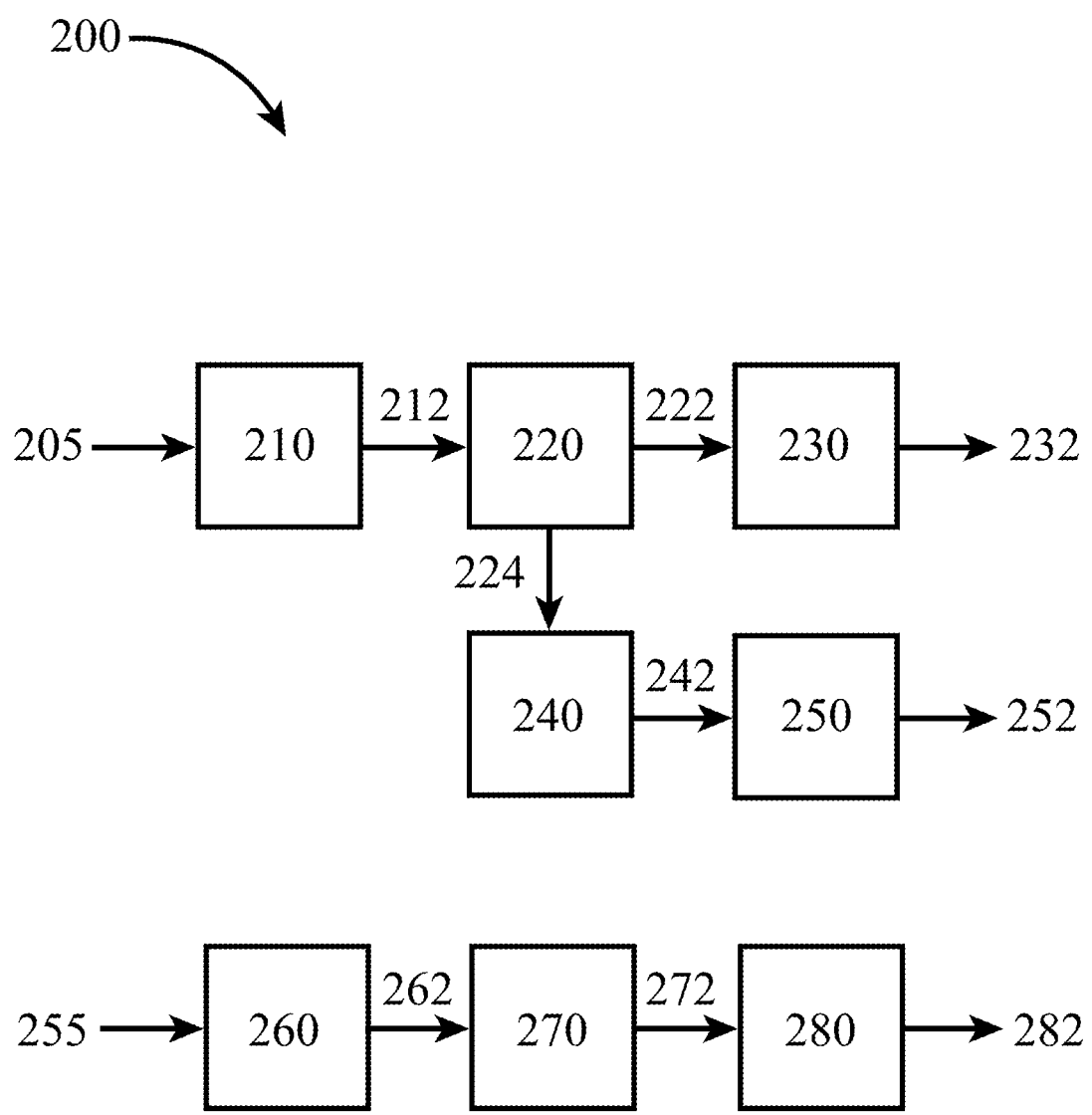
FIG. 2 illustrates a system for converting carboxylic acids and/or alcohols to fuels and/or fuel blendstocks, according to some embodiments of the present disclosure.

FIG. 2 illustrates a system 200 for producing paraffins for use as fuels and/or fuel blendstocks as described above, according to some embodiments of the present disclosure. In this exemplary system 200, a carboxylic acid stream 205, e.g. VFAs, may be directed to a ketonization reactor 210, such that at least a portion of the carboxylic acids is converted to a one or more ketones, resulting in the forming of an intermediate ketone stream 212. This conversion of carboxylic acids to ketones is show in Reaction 1 above and results in the formation of water and $CO_2$ byproducts (not shown in FIG. 2). In some embodiments of the present disclosure, as described herein, a carboxylic acid stream 205 may be bioderived; e.g. from a municipal solid waste, a food waste, a diary waste, etc. In some embodiments of the present disclosure, ketonization may be performed in a packed bed reactor containing a solid catalyst (not shown). In some embodiments of the present disclosure, the solid catalyst used in a ketonization reactor 210 may include a transition metal on a solid support. Examples of a solid support include a metal oxide, such as on oxide of at least one of zirconium, titanium, and/or niobium. Examples of transition metals suitable for the ketonization of carboxylic acids include at least one of platinum, palladium, ruthenium, nickel, cobalt, and/or molybdenum.

A ketonization catalyst may be in the form of a powder and/or pellet characterized by a number of physical properties including surface area and acidity. In some embodiments of the present disclosure a solid ketonization catalyst may have a surface area between about 25 $m^2/g$ and about 250 $m^2/g$, or between about 180 $m^2/g$ and about 220 $m^2/g$. In some embodiments of the present disclosure a solid ketonization catalyst may have a total acidity between about 100 umol/g and about 400 umol/g, or between about 210 umol/g and about 260 umol/g. In some embodiments of the present disclosure, the total acidity of a solid ketonization catalyst may be due substantially to Lewis acid sites. Further, the flow of the carboxylic acid stream 205 through a packed bed ketonization reactor 210 may be characterized by a weight hourly space velocity (WHSV) between about 1 $h^{-1}$ and about 10 $h^{-1}$, or between about 4 $h^{-1}$ and about 8 $h^{-1}$.

In some embodiments of the present disclosure, ketonization of a carboxylic acid stream 205 in a ketonization reactor 210 may be performed at a temperature between about 300° C. and about 450° C., or between about 325° C. and about 375° C., where this temperature is the average temperature of the mass contained within the ketonization reactor 210. Further, the ketonization reaction may be performed at a pressure between about −10 psig and about 250 psig, or between about 0 psig and about 10 psig. In some embodiments of the present disclosure, a carboxylic acid stream 205 directed to a ketonization reactor 210 may further include, in addition to the carboxylic acid(s), at least one of $H_2$ gas, an inert gas, and/or water. Water may be present in the carboxylic acid stream 205 at a concentration between greater than 0 wt % and about 25 wt %.

Referring again to FIG. 2, this exemplary system 200 then directs the intermediate ketone stream 212 formed in the ketonization reactor 210 to a separating unit 220. As described above, in some embodiments of the present disclosure, an intermediate ketone stream 212 may include a mixture of ketones. Referring again to Reaction 1 above, a ketone may be a central ketone having two alkyl group, each with between 1 and 11 carbon atoms, or more. Thus, in order to, among other things, meet the "Fast Track" requirement, the intermediate ketone stream 212 may be directed to a separating unit 220, which separates the intermediate ketone stream 212 into a first ketone stream 222 containing ketones having 8 or more carbon atoms, and a second ketone stream 224 having less than 8 carbon atoms. In some embodiments of the present disclosure, a separating unit 220 may include a distillation column.

Once separated the intermediate ketone stream 212 has been separated into two different ketone streams (222 and 224) according to their size, each can be further processed to yield their respective target molecules. Referring again to FIG. 2, the first ketone stream 222 of ketones have 8 or more carbon atoms may be directed to a first hydrodeoxygenation reactor 230, where the oxygen is removed from the ketones, resulting in the forming of one or more normal paraffins, as shown in Reaction 2 above. Note that this deoxygenation reaction utilizes hydrogen ($H_2$) and results in the formation of a water byproduct (not shown in FIG. 2).

In some embodiments of the present disclosure, deoxygenation of the ketones may be performed in packed bed hydrodeoxygenation reactor 230 containing a solid catalyst (not shown). In some embodiments of the present disclosure, the solid catalyst used in a hydrodeoxygenation reactor 230 (and/or 250) may include at least one of a transition metal and/or sulfur on a solid support. Examples of a solid support include a metal oxide, such as on oxide of at least one of aluminum, zirconium, titanium, and/or niobium. Examples of transition metals suitable for the hydrodeoxygenation of ketones include at least one of platinum, palladium, ruthenium, nickel, cobalt, and/or molybdenum.

A hydrodeoxygenation catalyst may be in the form of a powder and/or pellet characterized by a number of physical properties including surface area and acidity. In some embodiments of the present disclosure a solid hydrodeoxygenation catalyst may have a surface area between about 25 $m^2/g$ and about 550 $m^2/g$, or between about 180 $m^2/g$ and about 220 $m^2/g$. In some embodiments of the present disclosure a solid hydrodeoxygenation catalyst may have a total acidity between about 100 umol/g and about 400 umol/g, or between about 300 umol/g and about 360 umol/g. In some embodiments of the present disclosure, the total acidity of a solid hydrodeoxygenation catalyst may be due substantially to Lewis acid sites. Further, the flow of the ketone stream 222 through a packed bed hydrodeoxygenation reactor 230 may be characterized by a weight hourly space velocity (WHSV) between about 1 $h^{-1}$ and about 10 $h^{-1}$, or between about 4 $h^{-1}$ and about 8 $h^{-1}$.

In some embodiments of the present disclosure, deoxygenation of a first ketone stream 222 in a hydrodeoxygenation reactor 230 to form a normal paraffin stream 232, may be performed at a temperature between about 250° C. and about 450° C., or between about 300° C. and about 370° C., where this temperature is the average temperature of the mass contained within the hydrodeoxygenation reactor 230. Further, deoxygenation of a ketone may occur in a hydrodeoxygenation reactor 230 at a pressure between about 0 psig and about 1500 psig, or between about 400 psig and about 600 psig. In some embodiments of the present disclosure, the first ketone stream 222 may also include water, in addition to the ketones, with the water present at a concentration between greater than 0 wt % and about 25 wt %.

Referring again to FIG. 2, in this exemplary system 200, the separating unit 220 also produces a second ketone stream 224 that includes ketones having less than 8 carbon atoms. As described above, these smaller molecules can be oligomerized, i.e. their molecular weight increased, in order to be further synthesized into suitable liquid fuels. Thus, as shown in FIG. 2, the second ketone stream 224 from the separating unit 220 may be directed to an aldol condensation reactor 240, where the reaction shown in Reaction 3 may be performed, resulting in the formation of an oxygenated iso-olefin stream 242. As shown in Reaction 3, this condensation reaction also produces a water byproduct stream (not shown in FIG. 2). In some embodiments of the present disclosure, an aldol condensation reaction may be performed at a temperature between about 150° C. and about 230° C., at a pressure between about 0 psig and about 100 psig. Reaction 3 may utilize a solid catalyst that is acidic or amphoteric and may have a surface area between about 50 $m^2/g$ and about 250 $m^2/g$. The ketone feed may be diluted with a solvent such as at least one of toluene, octane, and/or decane, to a concentration of the ketone between about 10 vol % and about 50 vol % in the solvent. The residence time may be between about 2 hours and about 24 hours, or between about 4 hours and about 8 hours.

The oxygenated iso-olefin stream 242 produced in the aldol condensation reactor 240 may be subsequently directed to a second hydrodeoxygenation reactor 250 resulting in the conversion of at least a portion of oxygenated iso-olefin stream 242 to a first iso-paraffin stream 252. This conversion is summarized in Reaction 4 above. Note that this deoxygenation reaction utilizes hydrogen ($H_2$) and results in the formation of a water byproduct (not shown in FIG. 2). In some embodiments of the present disclosure, a second hydrodeoxygenation reactor 250 may be operated at essentially the same process conditions, using essentially the same catalyst, as the conditions and catalyst described above for a first hydrodeoxygenation reactor 230. In some embodiments of the present disclosure, at least a portion of the oxygenated iso-olefin stream 242 may be combined with at least a portion of the first ketone stream 222 to be subsequently fed to at least one of the first hydrodeoxygenation reactor 230 and/or the second hydrodeoxygenation reactor 250. In some embodiments of the present disclosure, a system 200 may utilize a single hydrodeoxygenation reactor (230 or 250) to deoxygenate both a first ketone stream 222 (having 8 or more carbon atoms) and a second ketone stream 224 (having less than 8 carbons atoms).

Referring again to FIG. 2, in some embodiments of the present disclosure, a system 200 may also convert a secondary alcohol(s) to an iso-paraffin stream for use as a fuel and/or fuel blendstock. As shown in Reactions 5 and 6 above, this conversion process may be accomplished by four reactions performed in series, conversion of a ketone to an alcohol, a dehydration reaction, an oligomerization reaction, and a hydrogenation reaction. However, in some embodiments of the present disclosure, referring again to Reaction 5, only Steps B, C, and D may be needed, or only Steps C and D, or only Step D, depending on the reactants available. As shown in the exemplary process of FIG. 2 where only Steps B, C, and D are performed, an alcohol stream 255 (e.g. a bioderived alcohol) that includes at least one secondary alcohol may be directed to a dehydration reactor 260, such that at least a portion of the alcohol is converted to a normal olefin stream (Part A of Reaction 5), resulting in the forming of a normal olefin stream 262. Next, the normal olefin stream 262 may be directed to an oligomerization reactor 270, such that at least a portion of the normal olefin is converted to at least one of an iso-olefin, an aromatic, and/or a cyclo-olefin (Part B of Reaction 5), resulting in the forming of an iso-olefin stream 272. Finally, the iso-olefin stream 272 may be directed to a hydrogenation reactor 280, where it is combined with and reacts with hydrogen ($H_2$) to form iso-paraffins (Part C of Reaction 5) contained in a second iso-paraffin stream 282.

In some embodiments of the present disclosure, the dehydration reaction and oligomerization reaction may be performed in a single reactor and/or in two reactor in series. Dehydration may be performed at a reaction temperature between about 100° C. and about 200° C., while at a reaction pressure between about 0 psig and about 600 psig. Oligomerization may be performed at reaction temperature between about 80 C and about 200° C., while at a reaction pressure between about 20 psig and about 1000 psig. Hydrogenation may be performed at a reaction temperature between about 50° C. and about 350° C., while at a reaction pressure between about 60 psig and about 100 psig. Dehydration may be performed with at least one of an acid catalyst and/or an acid supported metal catalyst. Acids catalysts include zeolites, silica-alumina, ion exchange resins, metal oxides (alumina, titania, or mixed of these oxides), and/or P-modified version of these aforementioned acids. Metal-doping of acid catalysts may be achieved using at least one of Cu, Ni, Ga, Cr, Fe, and/or Co. Hydrogenation may be accomplished utilizing catalysts the same as, or similar to, the catalysts used for Reaction 2, as described above.

Referring again to FIG. 2, two or more of the normal paraffin stream 232, the first iso-paraffin stream 252, and/or the second iso-paraffin stream 282 may be blended together to achieve a blend having specific targeted physical properties and/or performance metrics. In addition, in some embodiments of the present disclosure, at least one of the normal paraffin stream 232, the first iso-paraffin stream 252, and/or the second iso-paraffin stream 282 may be blended with some other fuel and/or fuel blendstock to achieve a blend having specific targeted physical properties and/or performance metrics. Examples of fuels that may be blended with the blendstocks described herein include at least one of commercial fossil jet fuel and/or diesel, gasoline, E10, biodiesel, renewable diesel and/or renewable jet from hydrotreating esters and fatty acids (HEFA), alcohol-to-jet fuel, Fischer Tropsch fuel, hydrocarbons from the catalytic upgrading of sugars, farnesane, algal, and/or other bioderived fuels (pyrolysis oil, hydrothermal liquefaction oil).

Figure 3:
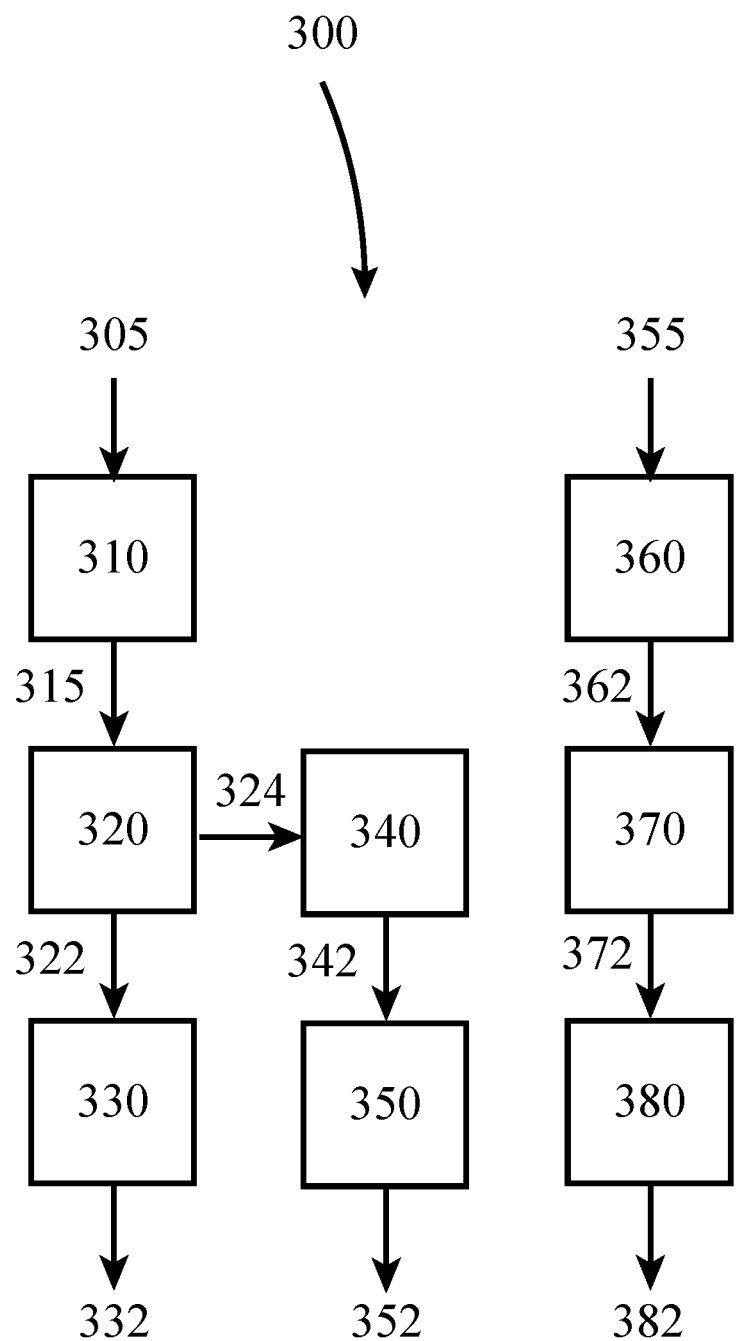
FIG. 3 illustrates a method for converting carboxylic acids and/or alcohols to fuels and/or fuel blendstocks, according to some embodiments of the present disclosure.

FIG. 3 illustrates a method 300 for producing fuels and/or fuel blendstocks, from one or more bioderived feed stocks. Such a method 300 may be accomplished using one or more of the components described above for a system 200. More specifically, FIG. 3 illustrates a method 300 for producing various normal paraffins, i.e. (a first product 332) and/or iso-paraffins (a second product 352 and/or a third product 382) synthesized from bioderived carboxylic acids (a first mixture 305) and/or bioderived alcohols (a fourth mixture 355). In summary, a first stream 305 that includes a carboxylic acid (e.g. one or more VFAs) may undergo a first treating 310, ketonization, such that at least a portion of the carboxylic acids are converted to one or more ketones, thereby creating a second mixture 315 containing the ketones. The second mixture 315 may than undergo a separating 320, whereby the separating creates a mixture having ketones with 8 or more carbon atoms, referred to herein as a first portion of the second mixture 322, and another mixture having ketones with less than 8 carbon atoms, referred to herein as a second portion of the second mixture 324. Each of these portions may then be treated to produce either normal paraffins or iso-paraffins.

Referring again to FIG. 3, the first portion of the second mixture 322 may be directed to a second treating 330 (i.e. hydrodeoxygenation), whereby the ketones (having 8 or more carbon atoms) are reacted with hydrogen (not shown) to produce a first product 332 containing normal paraffins. These normal paraffins may be subsequently used as a fuel and/or a fuel blendstock. The second portion of the second mixture 324 may be directed to a third treating 340 (i.e. aldol condensation), such that at least a portion of the ketones contained in the second portion of the second mixture 324 react (i.e. oligomerize) to form a third mixture 342 that includes oxygenated iso-olefins. This third mixture 342 may then be directed to a fourth treating 350 (i.e. hydrodeoxygenation), thereby forming a second product stream 352 containing iso-paraffins. In some embodiments of the present disclosure, the second treating 330 and the fourth treating 350 may be combined into a single step.

Referring again to FIG. 3, this exemplary method 300 also includes converting a fourth mixture 355 that includes alcohols to a second stream containing iso-paraffins, referred to herein as the third product 382. As shown herein, this may be achieved by directing the fourth mixture 355 of alcohols to a first reacting 360, i.e. dehydration reaction, such that at least a portion of the alcohols are converted to a fifth mixture 362 including normal olefins. Next, the fifth mixture 362 may be directed to a second reacting 370, i.e. oligomerization reaction, such that at least a portion of the normal olefins are converted to a sixth mixture 372 containing iso-olefins. Finally, the sixth mixture 372 may be directed to a third reacting 380, i.e. hydrogenation, such that at least a portion of the iso-olefins are converted to a third product 382 containing iso-paraffins.

Figure 4A:
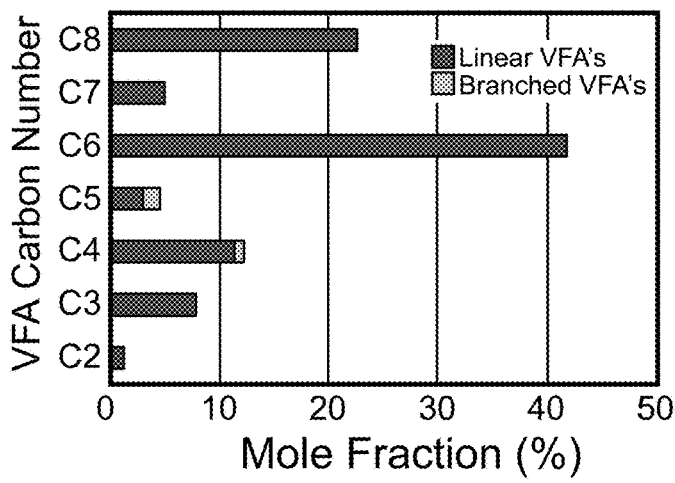
FIG. 4A illustrates modeled and experimental VFA ketonization carbon yields, according to some embodiments of the present disclosure. For the $C_6/C_8$ VFA feed, (1) VFA carbon chain length distribution, (2) ketone and $CO_2$ carbon yield and (3) model and experimental ketone carbon number profile. Blue represents $\geq C_8$ ketone carbon chain lengths suitable for Fast Track VFA-SAF, while orange represents $\leq C_7$ ketones that require coupling for Aldol Condensation VFA-SAF.
Figure 4A:
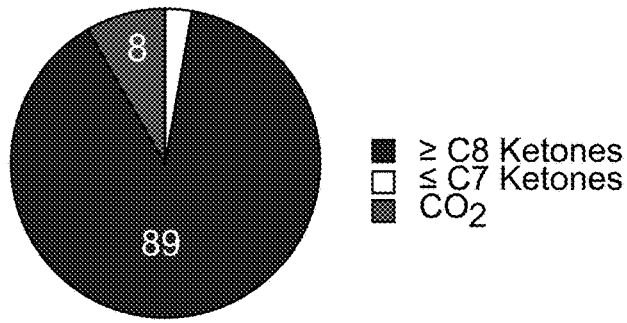
Figure 4A:
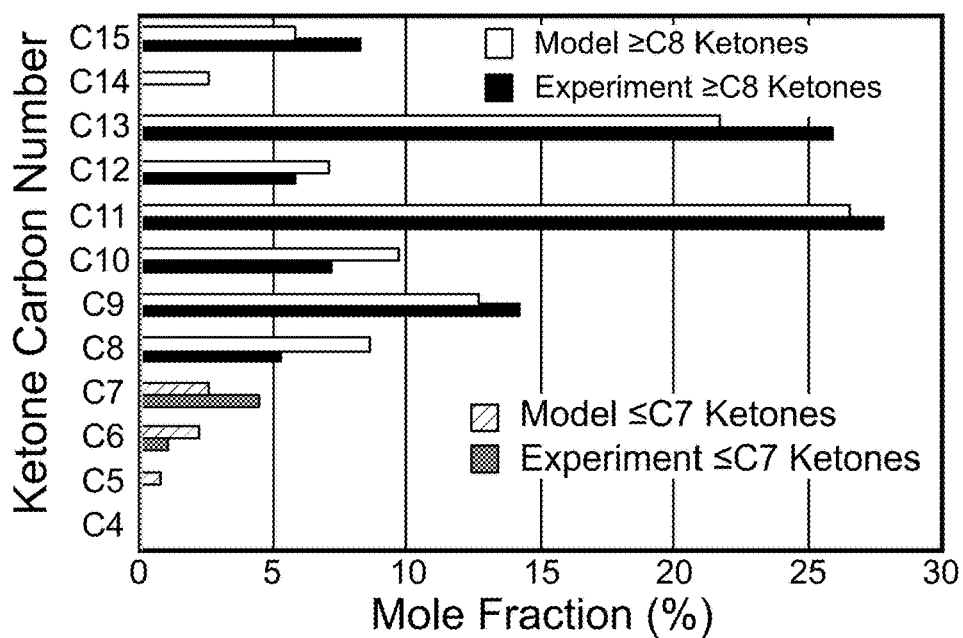
Figure 4B:
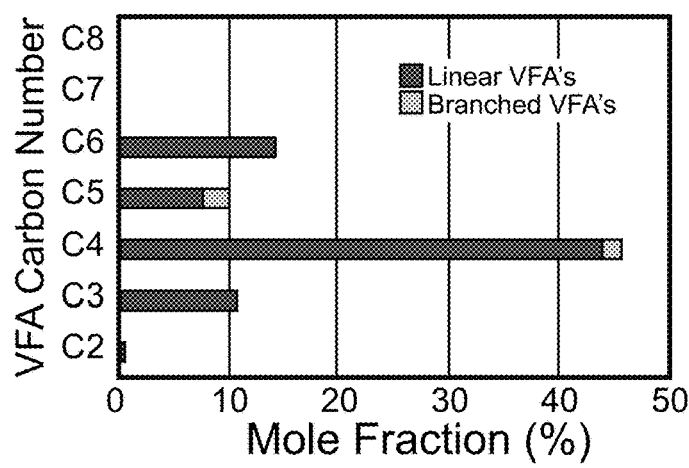
FIG. 4B illustrates modeled and experimental VFA ketonization carbon yields, according to some embodiments of the present disclosure. For the $C_4/C_6$ VFA feed, (1) VFA carbon chain length distribution, (2) ketone and $CO_2$ carbon yield and (3) model and experimental ketone carbon number profile. Blue represents $\geq C_8$ ketone carbon chain lengths suitable for Fast Track VFA-SAF, while orange represents $\leq C_7$ ketones that require coupling for Aldol Condensation VFA-SAF.
Figure 4B:
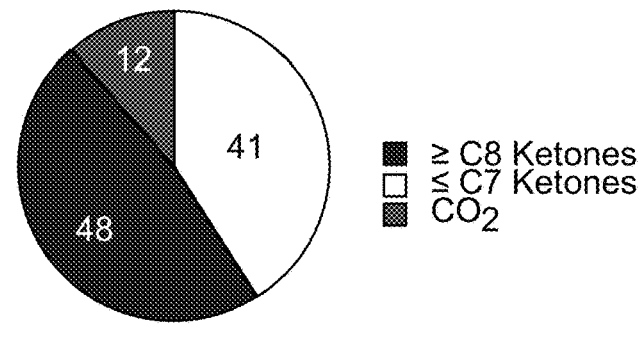
Figure 4B:
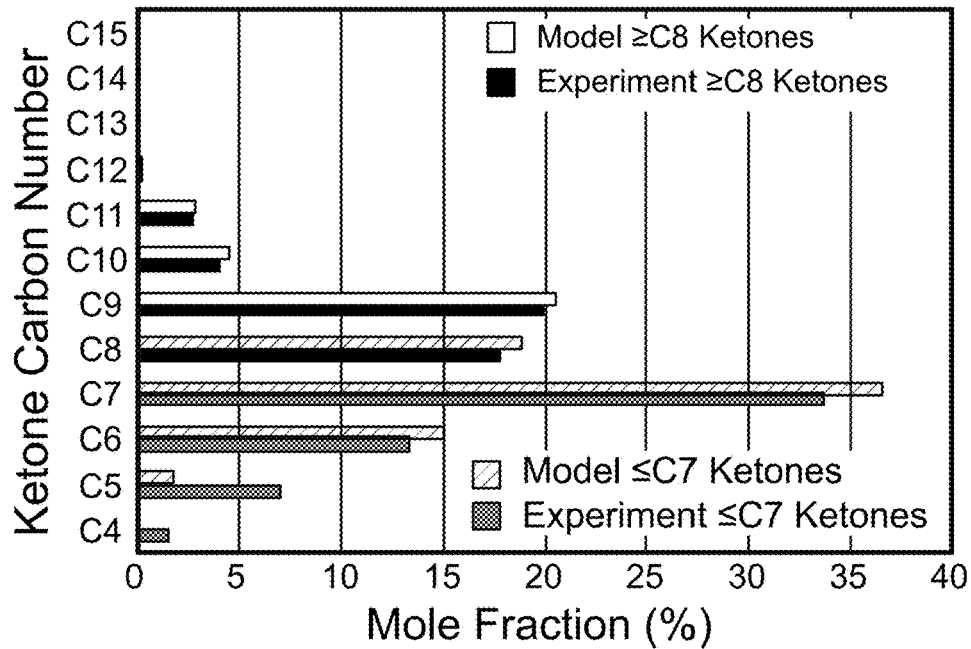

As mentioned above, and described in more detail below, the systems and methods for the conversion of bioderived carboxylic acids and/or alcohols result in the forming of unique bioderived fuels and/or fuel blendstocks, containing mixtures of paraffins, including iso-paraffins, normal paraffins, and/or cycloparaffins. For example, mixed VFAs were produced (having less than 3 wt % water) by an anaerobic digestion process of food waste via arrested methanogenesis. VFA chain lengths ranging from $C_3$-$C_8$ were produced and recovered. Table 2 summarizes the carbon number distributions resulting from these food waste derived VFAs. Two VFA samples of predominantly of $C_6/C_8$ and $C_4/C_6$ VFA were then prepared for downstream catalytic upgrading (see Panels 1 FIGS. 4A and 4B).

TABLE 2

Biogenic VFA distributions (mol %, dry basis) that were prepared as feedstocks for ketonization reactions. These same distributions were used for ketonization model calculations.

| Sample | $C_2$ | $C_3$ | $C_4$ | $i$-$C_4$ | $C_5$ | $i$-$C_5$ | $C_6$ | $C_7$ | $C_8$ |
|---|---|---|---|---|---|---|---|---|---|
| $C_4$ | 0.8 | 15.9 | 64.5 | 2.5 | 11.3 | 3.5 | 1.5 | 0.0 | 0.0 |
| $C_4/C_6$ | 0.5 | 13.3 | 53.9 | 2.1 | 9.4 | 2.4 | 17.7 | 0.0 | 0.0 |
| $C_6/C_8$ | 0.0 | 1.6 | 14.3 | 0.1 | 5.1 | 0.6 | 49.7 | 0.9 | 27.7 |

Figure 5:
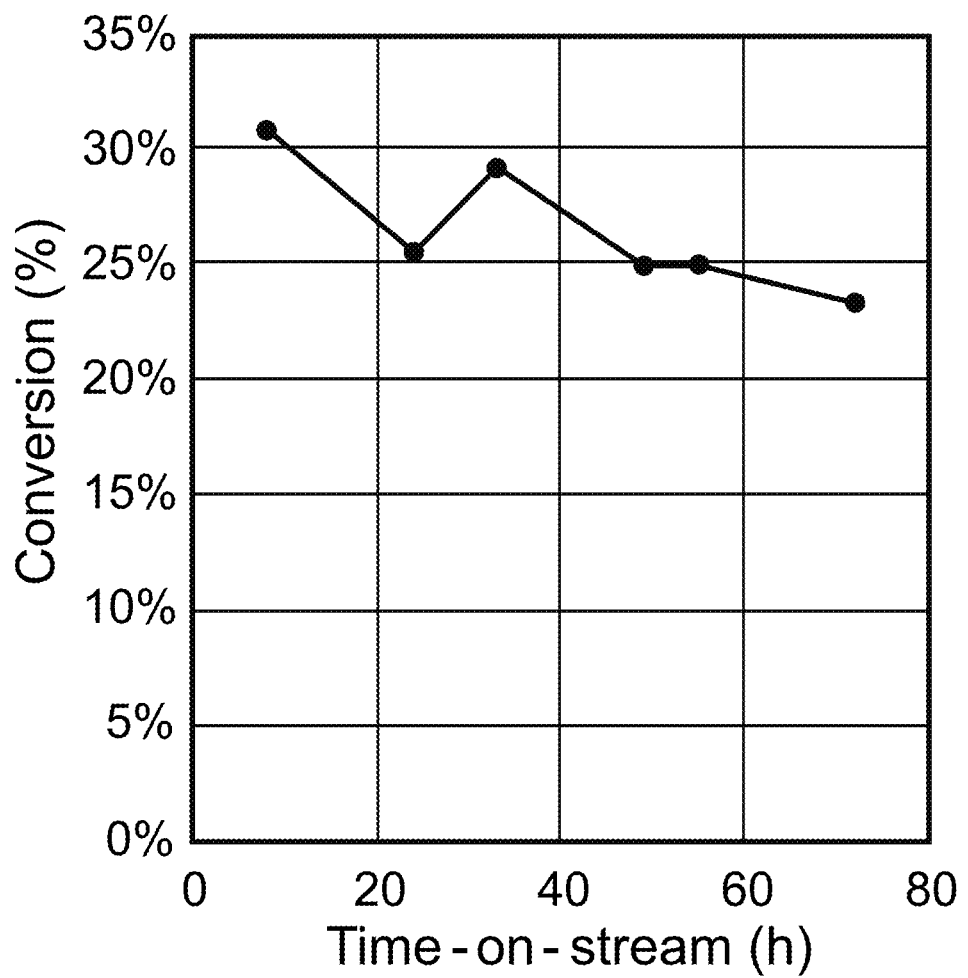
FIG. 5 illustrates ketonization catalyst stability under partial conversion conditions for 72 h of time-on-stream using model VFA's (Sigma-Aldrich) with a distribution to simulate the $C_4/C_6$ stream, according to some embodiments of the present disclosure. Reaction conditions: Catalyst loading 2 g $ZrO_2$, Ar flow 166 mL(STP) min$^{-1}$ at 1 atm, bed temperature 290° C., WHSV 7.7 h$^{-1}$ based on VFA mass flow rate.

Ketonization was then performed on these VFAs using a $ZrO_2$ catalyst. Conversion conditions were evaluated with mixed model VFAs reflective of the $C_4/C_6$ profile to assess stability with 72 hours of time-on-stream (TOS) (see FIG. 5). The first 48 hours of TOS resulted in a 6% drop in conversion, which appeared to stabilize, with the final 24 hours showing only 2% drop in conversion.

Figure 6A:
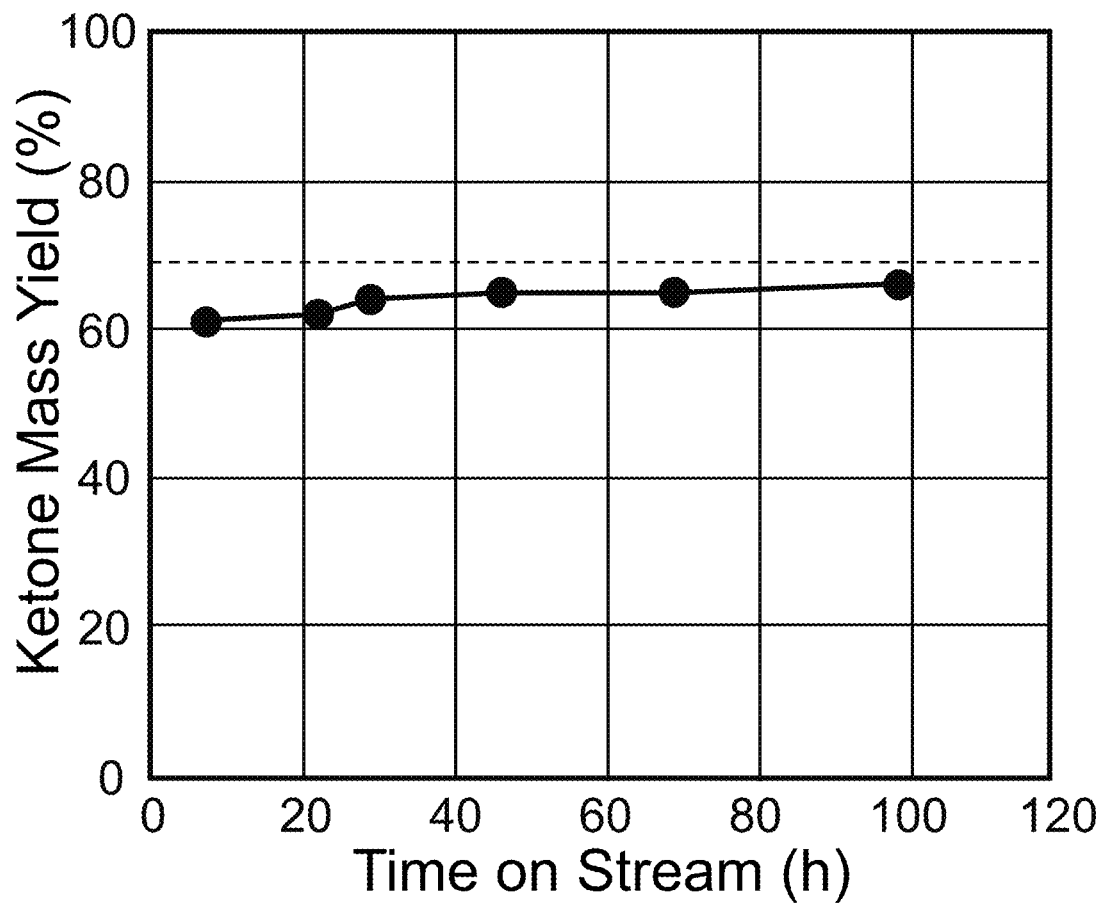
FIG. 6A illustrates ketonization catalyst performance with the biogenic $C_6/C_8$ VFA sample, according to some embodiments of the present disclosure. Complete conversion conditions with near theoretical yields. Reaction conditions: Catalyst loading 5 g $ZrO_2$, Ar flow 166 mL(STP) min$^{-1}$ at 1 atm, bed temperature 350° C., weight hourly space velocity (WHSV) 3.1 h$^{-1}$ based on VFA mass flow rate.
Figure 6B:
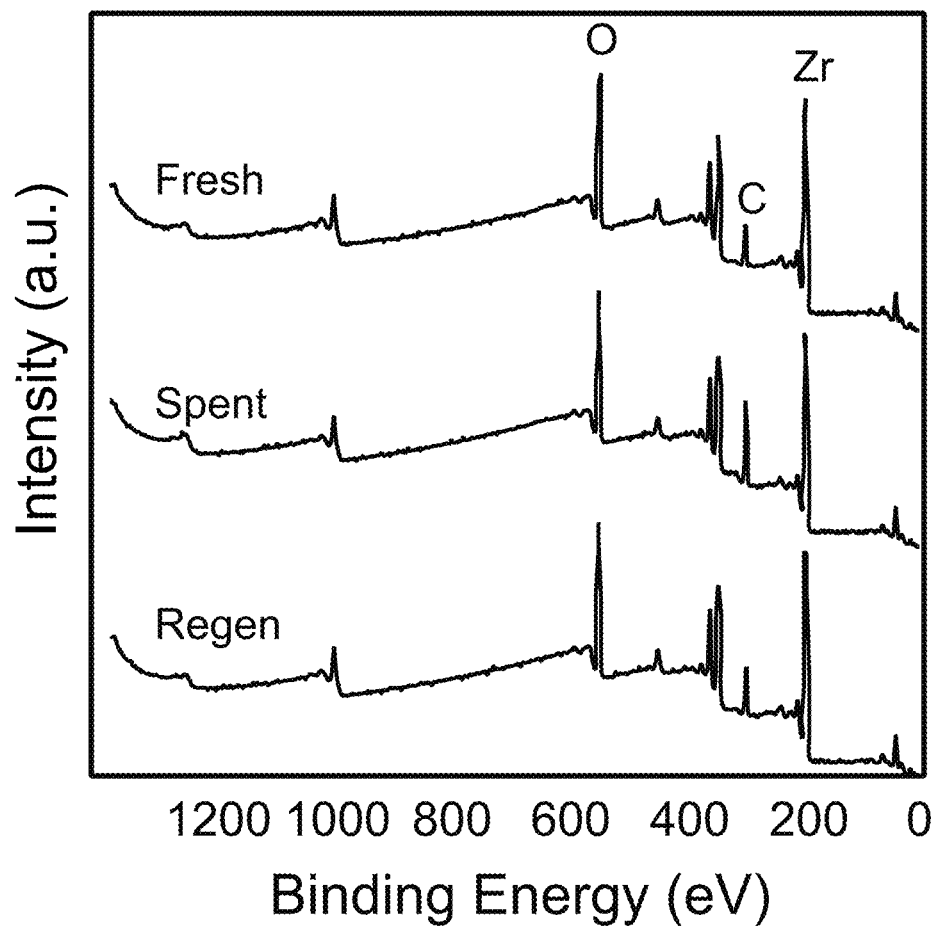
FIG. 6B illustrates ketonization catalyst performance with the biogenic $C_6/C_8$ VFA sample, XPS survey spectra of fresh, spent, and regenerated $ZrO_2$, according to some embodiments of the present disclosure.
Figure 7:
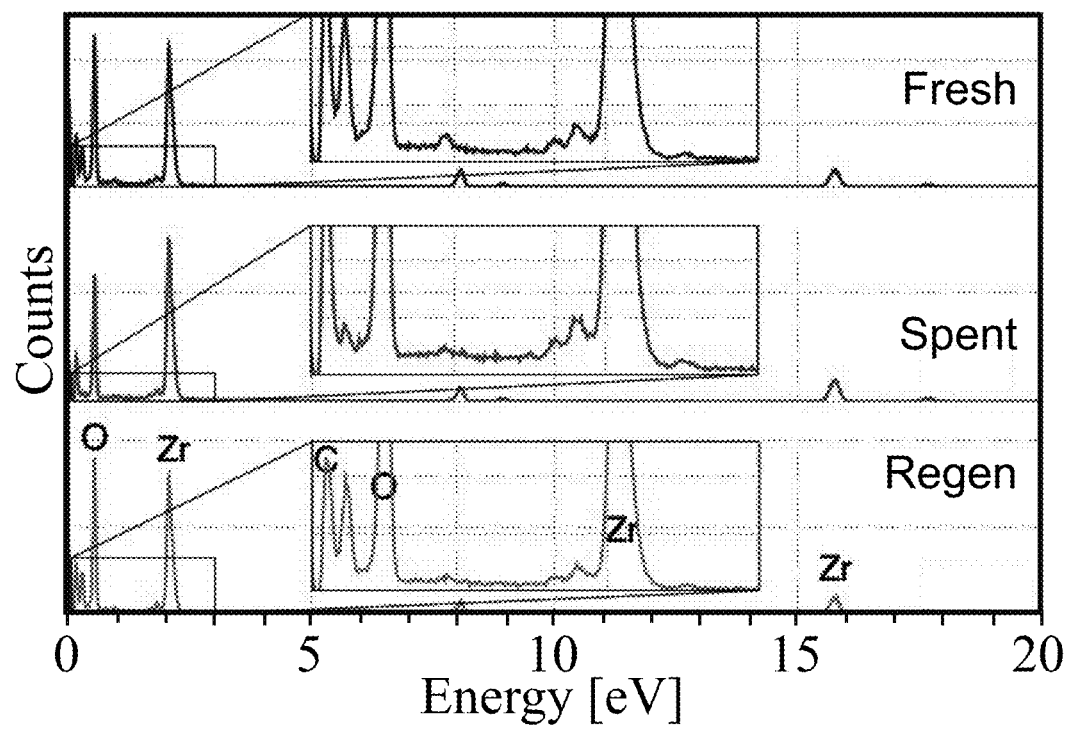
FIG. 7 illustrates EDS spectra generated from fresh, spent, and regenerated $ZrO_2$, according to some embodiments of the present disclosure.

Additional experiments were then performed with biogenic VFAs to assess the deposition of biogenic impurities and the ability to regenerate the catalyst. The biogenic VFA feed contained trace alkali impurities, as well as sulfur, which may deposit on the catalyst surface and poison acid sites over time, particularly alkali elements that are known to deactivate reducible metal oxides. A complete conversion experiment was performed for over 100 hours of TOS with the $C_6/C_8$ VFA sample (see FIG. 6A). Analysis of the used $ZrO_2$ catalyst by X-ray photoelectron spectroscopy (XPS) (see FIG. 6B), and Table 3) and scanning transmission electron spectroscopy in conjunction with energy dispersive x-ray spectroscopy (STEM-EDS) (see FIG. 7) showed no measurable levels of biogenic impurities on the catalyst surface, within the limits of detection. Analysis of the self-separating ketonization organic phase showed impurity levels at or below ppm detection limits, which suggests preferential partitioning of impurities into the aqueous phase occurred. Thermal gravimetric analysis of the spent catalyst measured a carbon content of about 1.8 wt % (see Table 4), which may be due to the formation of larger oligomers from ketone condensation that deposit on the surface. BET surface area and total pore volume decreased by <10%, consistent with the relatively low coke content.

TABLE 3

Surface composition (atomic %) of fresh, spent, and regenerated $ZrO_2$ determined by XPS.

| Catalyst | Zr | O | C | Na |
|---|---|---|---|---|
| Fresh | 18.1 | 45.4 | 36.3 | 0.3 |
| Spent | 13.1 | 36.0 | 50.4 | 0.5 |
| Regen | 17.5 | 12.7 | 37.9 | 0.3 |

TABLE 4

Fresh, spent, and regenerated $ZrO_2$ catalyst material properties used for 100 hours of continuous time on stream ketonization of the $C_6/C_8$ VFA sample

| $ZrO_2$ Catalystسample | Surface Area ($m^2$/g) | Pore Vol (mL/g) | Total Acidity (μmol/g) | Carbon Content (wt %) |
|---|---|---|---|---|
| Fresh | 51.3 | 0.29 | 246 | NA |
| 100-h Spent | 47.6 | 0.27 | ND | 1.8 |
| Regenerated | 48.4 | 0.30 | 233 | 0.0 |

NA: Not applicable for fresh catalyst
ND: Not determined due to carbon laydown that interferes with measurement.

Figure 6C:
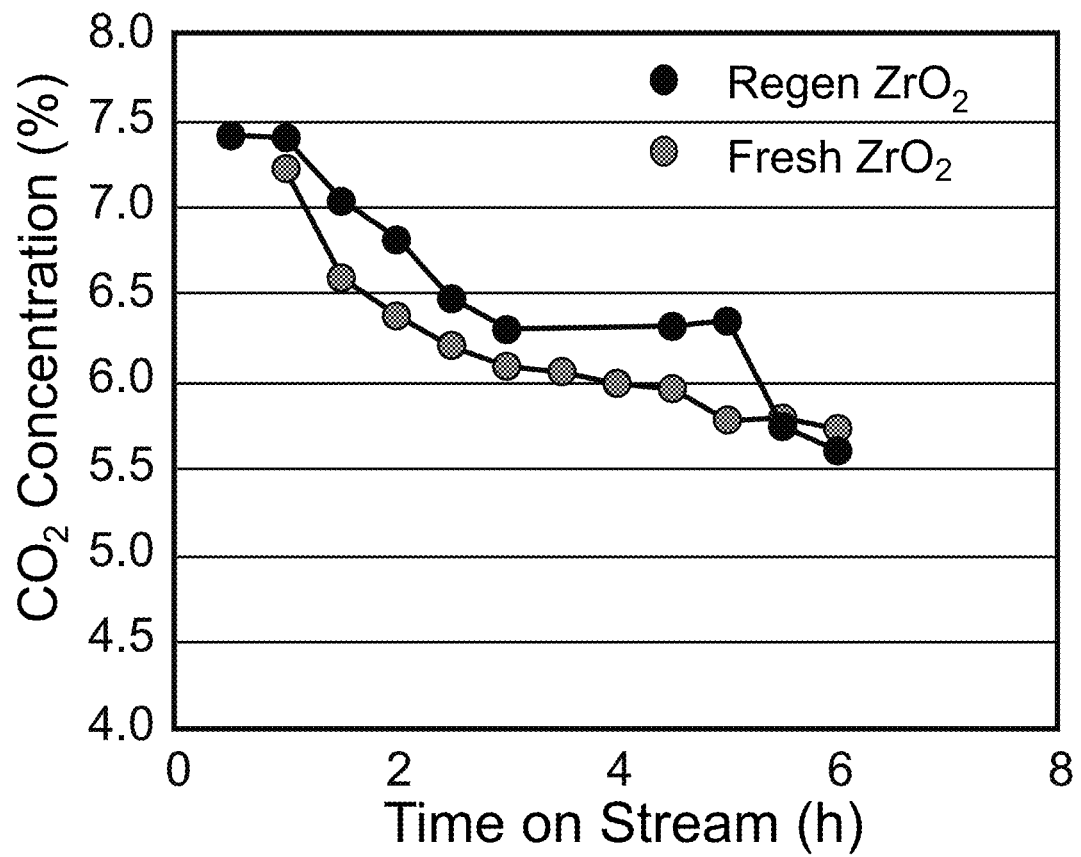
FIG. 6C illustrates ketonization catalyst performance with the biogenic $C_6/C_8$ VFA sample, ketonization catalyst stability under partial conversion conditions before and after regeneration using the spent full conversion catalyst, according to some embodiments of the present disclosure. Reaction conditions: Catalyst loading 2 g $ZrO_2$, Ar flow 166 mL(STP) min$^{-1}$ at 1 atm, bed temperature 290° C., WHSV 7.7 h$^{-1}$ based on VFA mass flow rate. Regeneration conditions: 5° C./min to 500° C., hold 12 h, cool naturally, in flowing air.

Regeneration of the used (for 100 hours) $ZrO_2$ catalyst exposed to biogenic impurities was performed by a typical oxidation cycle in flowing air at 500° C. Following regeneration, carbon was no longer detected on the catalyst surface by thermogravimetric analysis (TGA) and similar textural properties and surface acidity were observed as the fresh catalyst (see Table 4 above). Ketonization conversion tests (~37% VFA conversion, 290° C., weight hourly space velocity of 7.7 h$^{-1}$ confirmed comparable ketonization activity between the fresh and regenerated catalyst using the biogenic $C_4/C_6$ VFA sample with online detection of effluent gas $CO_2$ by nondispersive infrared detection (NDIR), with differences within experimental error (see FIG. 6C). As anticipated based on the spent catalyst characterization results, impurities were not detected on the regenerated $ZrO_2$ (see FIG. 6B) with comparable crystallite sizes before and after oxidative treatment.

Figure 8A:
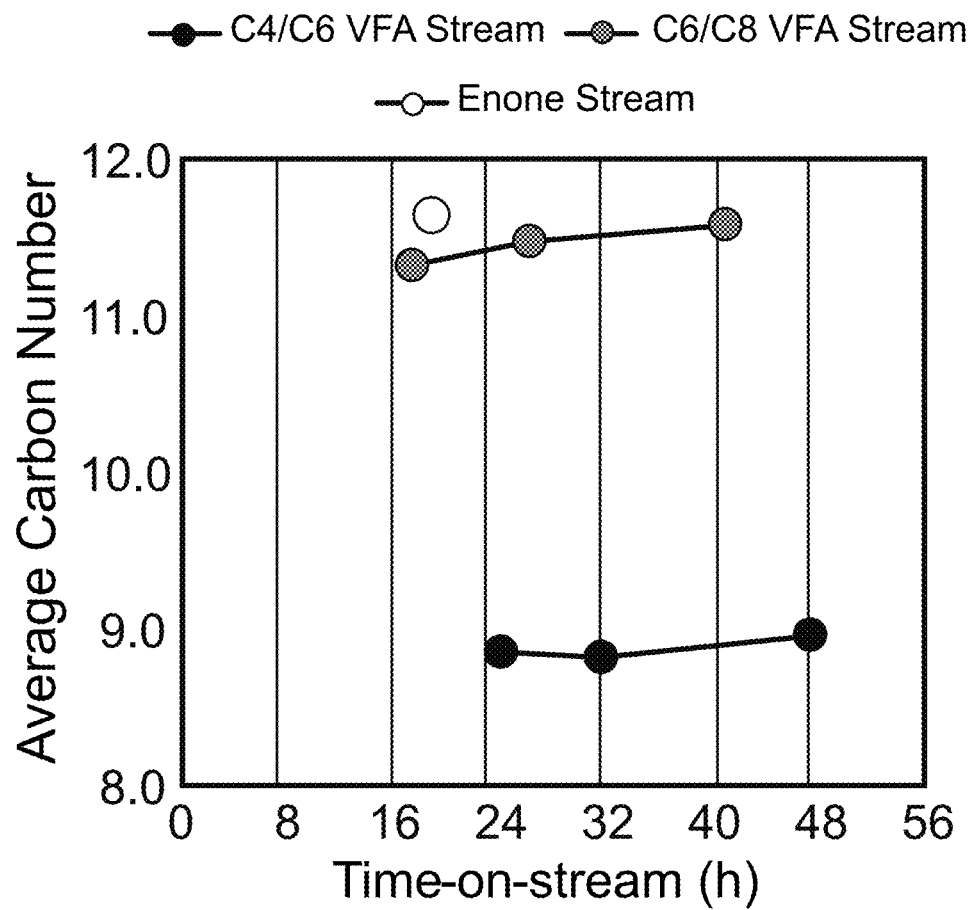
FIG. 8A illustrates average hydrocarbon carbon number versus time-on-stream variation during ketone and enone hydrodeoxygenation for various samples, according to some embodiments of the present disclosure. hydrocarbon mass yield.
Figure 8B:
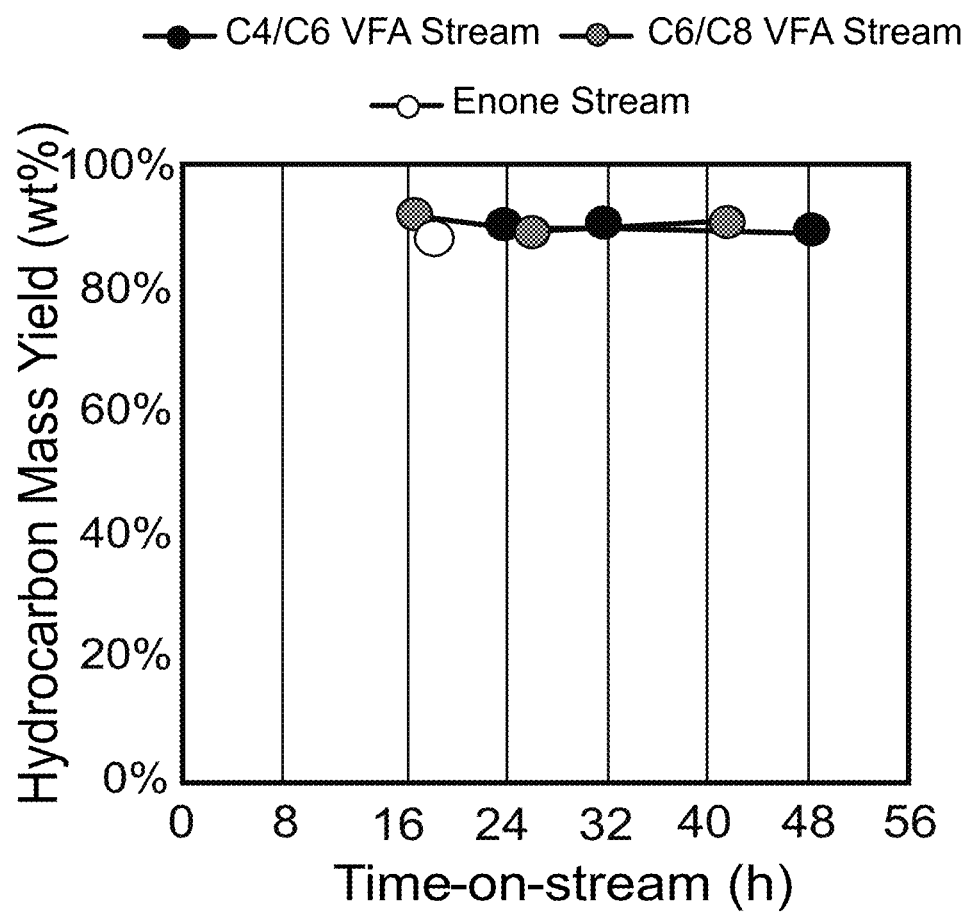
FIG. 8B illustrates hydrocarbon mass yield versus time-on-stream variation during ketone and enone hydrodeoxygenation for various samples, according to some embodiments of the present disclosure.

Next the ketones derived from the $C_6/C_8$ VFA sample were processed directly by hydrodeoxygenation to produce predominantly normal paraffins suitable for Fast Track VFA-SAF. Hydrodeoxygenation was performed with a 3% Pt/$Al_2O_3$ catalyst. In this example, stable hydrodeoxygenation hydrocarbon production was observed for up to 48 hours of TOS under complete conversion conditions with a liquid mass balance of 99% (see FIGS. 8A and 8B). Following hydrodeoxygenation, the hydrocarbon phase was decanted and trace amounts of <$C_7$ hydrocarbons (≤9.8% of sample mass) were removed by distillation prior to neat and blended fuel property analysis. The overall VFA-to-hydrocarbon carbon yield was 79% (mass yield 58%), which approached theoretical (82% carbon yield and 61% mass yield).

Neat fuel properties of Fast Track VFA-SAF produced from the $C_6/C_8$ VFA sample were then evaluated by Tier α and β screening (see Table 1). Values were compared to specifications for an aviation fuel containing SAF, as defined by ASTM D7566 Table 5. The neat Fast Track VFA-SAF displayed an average carbon number of 11.3, with 7 wt % isoparaffins and 2 wt % cycloparaffins detected. Fuel property measurements of the neat sample (see Table 6) confirmed its moderately higher net heat of combustion (nHOC) than the selected reference fossil jet fuel (43.98 MJ/kg, Jet A 43.0 MJ/kg), with viscosity and surface tension being within the typical range of fossil jet. Normalized sooting concentration measurements for the 10 vol % and 20 vol % blends (see Table 7) suggest that neat Fast Track VFA-SAF extrapolates to a 65% reduction in sooting relative to fossil Jet A (see Table 6). However, the high concentration of small (≤$C_9$) normal paraffins resulted in flash point being below specifications (31° C., spec 38° C.), gravimetric density being below specifications (743 kg/m$^3$, spec 775-840 kg/m$^3$), and boiling point distribution being below the typical range for Jet A (see Table 6). The limited degree of molecular branching also resulted in freezing point above spec (-27° C., spec -40° C.). Flashpoint and boiling point limitations of the neat fuel can be overcome by distillation to remove out-of-specification cuts, while density require structural compositional adjustments.

TABLE 5

Elemental analysis of the feed and upgrading products for C6/C8 and C4/C6 food-waste derived VFA samples.

| | ppm | | | | | |
|---|---|---|---|---|---|---|
| | $C_4/C_6$ VFA | $C_4/C_6$ Ketone | $C_4/C_6$ FT | $C_6/C_8$ VFA | $C_6/C_8$ Ketone | $C_6/C_8$ FT |
| Al | <0.4 | <0.4 | <0.4 | 1.2 | <1 | <0.4 |
| B | <0.2 | <0.2 | <0.2 | 1.8 | <1 | <0.2 |
| Ca | <0.1 | <0.1 | <0.1 | 0.8 | <0.1 | <0.1 |
| Fe | 0.4 | <1 | <1 | 3.0 | <0.1 | <0.1 |
| K | <1 | <1 | <1 | 236 | <1 | <1 |
| Mg | <0.1 | <0.1 | <0.1 | 4.1 | <0.1 | <0.1 |
| Mn | <0.1 | <0.1 | <0.1 | <0.2 | <0.2 | <0.1 |
| N | 37.0 | ND | 1.2 | 67.7 | 25.9 | ND* |
| Na | 11.8 | <1 | <1 | 104.8 | <1 | <1 |
| P | <1 | <1 | <1 | <10 | <10 | <1 |
| S | 8.2 | 1.0 | <1 | 32 | <10 | <1 |
| Si | <1 | <1 | <1 | <1 | <1 | <1 |
| Zn | <0.1 | <1 | <0.1 | <1 | <1 | <0.1 |

FT: Fast Track.
ND: Not determined due to volume limitations

TABLE 6

Fuel properties for n-paraffin Fast Track VFA-SAF and isoparaffin Aldol Condensation VFA-SAF, and blend criteria and Jet A fuel properties out-of-spec properties in bold.

| Property | 10% SAF Jet Blend Criteria$^a$ | Jet A | Fast Track $C_6/C_8$ VFA-SAF 10% | Fast Track $C_6/C_8$ VFA-SAF 20% | Fast Track $C_6/C_8$ VFA-SAF 100% | Fast Track $C_4/C_6$ VFA-SAF 10% | Fast Track $C_4/C_6$ VFA-SAF 20% | Fast Track $C_4/C_6$ VFA-SAF 100% | Aldol Cond. $C_4/C_6$ VFA-SAF 30% | Aldol Cond. $C_4/C_6$ VFA-SAF 100% | VFA-SAF Fast/Aldol 70% Blend$^d$ | Alcohol Derived |
|---|---|---|---|---|---|---|---|---|---|---|---|---|
| $T_{cloud\ or\ freeze}$ (° C.) | <-40 | -52 | -47 | -44.5 | -26.9 | -50.9 | -52.2 | -61.7 | -52.6 | -53.4 | -60.7 | -48 |
| IBP (° C.)$^b$ | — | 159 | 151 | 148 | 102 | 150 | 140 | 136 | 151 | 181 | 143 | ND |
| T5 (° C.) | — | 173 | 169 | 164 | 135 | 165 | 162 | 142 | 179 | 209 | 165 | ND |
| T10 (° C.) | Ph. <205 | 177 | 175 | 174 | 147 | 171 | 162 | 138 | 184 | 216 | 173 | ND |
| T20 (° C.) | — | 185 | 185 | 183 | 166 | 178 | 172 | 147 | 193 | 218 | 189 | ND |
| T30 (° C.) | — | 192 | 191 | 192 | 176 | 186 | 178 | 146 | 200 | 220 | 198 | ND |
| T50 (° C.) | report | 205 | 206 | 206 | 199 | 202 | 195 | 149 | 212 | 222 | 213 | ND |
| T70 (° C.) | — | 221 | 220 | 221 | 219 | 218 | 214 | 153 | 224 | 228 | 223 | ND |
| T80 (° C.) | — | 231 | 229 | 230 | 223 | 228 | 225 | 165 | 233 | 242 | 233 | ND |
| T90 (° C.) | report | 245 | 243 | 243 | 235 | 242 | 240 | 179 | 251 | 268 | 254 | ND |
| T95 (° C.) | — | 256 | 255 | 254 | 256 | 254 | 254 | 183 | 268 | 290 | 277 | ND |
| $T_{boil}$ or T100 (° C.) | Ph. <300 | 271 | 270 | 268 | 271 | 267 | 267 | 202 | 289 | 309 | 298 | ND |
| Density, 15° C. (g/mL) | 0.775-0.840 | 0.802 | 0.798 | 0.792 | 0.743 | 0.795 | 0.787 | 0.723 | 0.796 | 0.780 | 0.776 | 0.778 |
| v, 15° C. (cSt) | | 1.8 | ND | ND | ND | 1.81 | 1.70 | 1.07 | 2.14 | 2.78 | 1.96 | ND |

TABLE 6-continued

Fuel properties for n-paraffin Fast Track VFA-SAF and isoparaffin Aldol Condensation VFA-SAF, and blend criteria and Jet A fuel properties out-of-spec properties in bold.

| Property | 10% SAF Jet Blend Criteria[a] | Jet A | Fast Track $C_6/C_8$ VFA-SAF 10% | Fast Track $C_6/C_8$ VFA-SAF 20% | Fast Track $C_6/C_8$ VFA-SAF 100% | Fast Track $C_4/C_6$ VFA-SAF 10% | Fast Track $C_4/C_6$ VFA-SAF 20% | Fast Track $C_4/C_6$ VFA-SAF 100% | Aldol Cond. $C_4/C_6$ VFA-SAF 30% | Aldol Cond. $C_4/C_6$ VFA-SAF 100% | VFA-SAF Fast/Aldol 70% Blend[d] | Alcohol Derived |
|---|---|---|---|---|---|---|---|---|---|---|---|---|
| v, −20° C. (cSt) | <8 | 4.7 | 4.38 | 4.30 | 3.45 | 4.02 | 3.64 | 1.91 | 5.23 | 8.38 | 4.62 | 6.0 |
| v, −40° C. (cSt) | <12 | 9.551 | 8.89 | 8.64 | — | 7.95 | 6.96 | 2.99 | 11.54 | 24.17 | 9.97 | 14.0 |
| Surface Tension, RT (mN/m) | — | 24.8 | 25.8 | 25.1 | 24.0 | 25.8 | 25.0 | 23.1 | 25.8 | 25 | 24.2 | 22 |
| $T_{flash}$ (° C.) | 38-66 (or ≥38) | 48 | 48 | >38 | 31 | 42 | 39 | 24 | 53 | 62 | 39 | 29 |
| % C | — | 86.1 | 86.3% | 85.5% | 84.3% | 85.7% | 85.7% | 83.0% | 85.2% | 84.9% | 84.7% | ND |
| % O | — | 0 | 0.7% | 0.6% | 0.7% | 0.7% | 0.4% | 2.4% | 1.2% | 0.4% | 1.2% | ND |
| % H | — | 14% | 14.4% | 13.9% | 15.4% | 13.6% | 13.8% | 14.6% | 13.6% | 14.7% | 14.2% | ND |
| N (mg/kg) | <2 | ND | ND | ND | ND | ND | ND | <1.0 | 1.2 | ND | ND | ND |
| Acidity (mg KOH/g) | — | 0.005 | ND | ND | ND | ND | ND | 0.15 | 0.10 | ND | ND | ND |
| nHOC (MJ/kg) | >42.8 | 43.01 | 43.18 | 43.43 | 43.98 | 43.39 | 43.39 | 44.49 | 43.45 | 44.41 | 43.74 | 44 |
| LHV (MJ/L) | ≥Jet A * | 34.49 | 34.45 | 34.40 | 32.68 | 34.50 | 34.15 | 32.18 | 34.59 | 34.62 | 33.93 | 34 |
| Cetane Number (CN) | — | 48.4 | 51.5 | 53.0 | ND | 50.9 | 51.9 | 63.6 | 56 | 73 | 63.6 | ND |
| NSC[c] | ≤1* | 1 | ND | 0.871 | ND | 0.931 | 0.870 | 0.354 | 0.851 | 0.526 | 0.655 | ND |

TABLE 7

Measured fuel properties for the 10 vol % Fast Track VFA-SAF (Fast) blend produced from the $C_6/C_8$ VFA sample, 30 vol % Aldol Condensation VFA-SAF (Aldol) blend produced from the $C_4/C_6$ VFA sample, and 20%/50% Fast Track/Aldol VFA-SAF blend produced from the $C_4/C_6$ sample. Values are provided for D7566 specs and fossil Jet A. Volume percent closure for blends is with fossil Jet A.

| Fuel Property | Blend Criteria (D7566 Table 1) | Jet A POSF 10325 | 10% $C_6/C_8$ Fast | 30% $C_4/C_6$ Aldol | 20%/50% $C_4/C_6$ Fast/Aldol |
|---|---|---|---|---|---|
| VFA Sample | NA | NA | $C_6/C_8$ | $C_4/C_6$ | $C_4/C_6$ |
| Acidity (mg KOH/g) | Max 0.10 | 0.005 | *0.02* | ND | 0.10 |
| Aromatics (%) | Max 25 | 18 | 16.2 | 12.9 | 5.8 |
| Sulfur (ppm) | Max 3 | 421 | ND | ND | ND |
| T10 | Max 205 | 177 | 175 | 184 | 189 |
| T50 | Report | 205 | 206 | 212 | 213 |
| T90 | Report | 245 | 243 | 251 | 254 |
| T100 | Max 300 | 271 | 270 | 289 | 277 |
| Flash Pt (° C.) | Min 38 | 48 | 48 | 53 | 39 |
| Density 15° C. (kg/m³) | 775 to 840 | 802 | 798 | 796 | 776 |
| Freeze Pt (° C.) | Max −40 | −52 | −47 | −53 | −61 |
| Visc. −20° C. (mm²/s) | Max 8.0 | 4.7 | 4.4 | 5.2 | 4.6 |
| Visc. −40° C. (mm²/s) | Max 12 | 9.6 | 8.9 | 11.5 | 10.0 |
| Surface Ten. 20° C. (mN/m) | NA | 24.8 | 25.8 | 25.8 | 24.2 |
| nHOC (MJ/kg) | Min 42.8 | 43.0 | 43.2 | 43.4 | 43.7 |
| Indicated Cetane Number | NA | 48 | 52 | ND | 64 |
| Normalized Soot Concentration | NA | 1 | 0.93 | 0.85 | 0.66 |

ND: Not determined experimentally due to volume limitations.
NA: Not applicable
Italics: Estimated based on neat measurement.

To address neat fuel property limitations, Fast Track VFA-SAF was blended at 10 vol % with Jet A. Blending at 10 vol % resulted in all measured fuel properties being within spec (see Tables 6 and 7. The freezing point of neat Jet A increased by 5° C. to −47° C. upon blending, staying well below the limit of −40° C. No change was observed in the flash point of Jet A after blending due to the low concentration of volatile components. The boiling point distribution of the blend was within the typical range of fossil jet fuel (see Table 6). Improvements in neat Jet A fuel properties upon blending included a modest increase in specific energy density to 43.2 MJ/kg, an increase in the indicated cetane number from 48 to 52, and a decrease in the normalized soot concentration of 7%. Additionally, the acidity of the blend is anticipated to be 0.02 mg KOH/g (based on the measured 0.15 mg KOH/g acidity of the neat fuel), which is well within the blend maximum of 0.10 mg KOH/g. While Fast Track limits blending to 10 vol %, additional testing determined that the 20 vol % blend still met flashpoint criteria (see Tables 6 and 8).

TABLE 8

Flashpoint (° C.) of the Fast Track $C_6/C_8$ VFA-SAF, Fast Track $C_4/C_6$ VFA-SAF, and Aldol Condensation $C_4/C_6$ VFA SAF, with out-of-specification (flashpoint <38° C.) in bold.

| SAF Blend | Fast Track $C_6/C_8$ VFA-SAF | Fast Track $C_4/C_6$ VFA-SAF | Aldol Cond. $C_4/C_6$ VFA-SAF |
|---|---|---|---|
| 10% | 48 | 42 | — |
| 20% | 38 | 39 | — |
| 30% | — | — | 53 |
| 50% | 34 | — | — |
| 100% | 31 | 24 | 62 |

In addition, as described above, branched iso-paraffins produced from aldol condensation VFA-SAF were evaluated for their neat and blended Tier α and Tier β fuel properties. Batch aldol condensation reactions were performed with the ketones (having less than 8 carbon atoms) derived $C_4/C_6$ VFA sample. Ketones <$C_8$ were initially separated by fractional distillation and condensed at 20 wt % in decane using $Nb_2O_5$ powder catalyst due to its high acidity and activity for internal ketone condensation. Single pass ketone conversion to enones (i.e. the branched, oxygenated olefins shown in Reaction 3) was dependent on molecular structure, varying between 12% and 100% (see Table 9). Carbon loss to gas-phase products was insignificant, with liquid mass balance closure >90% after catalyst filtration. Previous efforts have demonstrated the regenerability of $Nb_2O_5$ for 4-heptanone condensation and recycle of solvent and unreacted ketone, (24) with further work needed to evaluate continuous reactor configurations. Enone products were recovered by distillation and processed neat over the same 3 wt % $Pt/Al_2O_3$ hydrodeoxygenation catalyst. The recovered hydrocarbon phase was used for testing without further workup.

TABLE 9

Percent conversion ($[R_{in}] - [R_{out}])/[R_{in}]$ of mixed ketone aldol condensation.

| Component | Trial 1 | Trial 2 | Trial 3 | Average |
|---|---|---|---|---|
| 2-pentanone | 100% | 100% | 100% | 100% |
| 3-pentanone | 92% | 92% | 93% | 92% |
| 3-hexanone | 77% | 76% | 76% | 76% |
| 2-methyl-3-hexanone | 41% | 40% | 32% | 38% |
| 4-heptanone | 58% | 58% | 55% | 57% |
| 3-heptanone | 61% | 65% | 61% | 63% |
| 2-methyl-4-heptanone | 32% | 34% | 29% | 32% |
| 3-Methyl-4-heptanone | 14% | 16% | 7% | 12% |
| 5-dimethyl-3-hexanone | 22% | 29% | 13% | 21% |
| 4-octanone | 52% | 53% | 48% | 51% |
| 3-octanone | 70% | 73% | 71% | 71% |
| 4-nonanone | 49% | 50% | 44% | 48% |
| decane (solvent) | −2% | −4% | −3% | −3% |

The neat Aldol Condensation VFA-SAF showed a higher average carbon number of 13.8 due to the coupling step that converts $C_5$-$C_7$ ketones into predominantly $C_{10}$-$C_{14}$ enones (see Table 6). The sample contained 76% isoparaffins, with 13% normal paraffins, 9% mono-cycloparaffins, and 1% aromatics, with ring structures likely due to trimer formation during ketone condensation. The relatively low percentage of ≤$C_{10}$ hydrocarbons resulted in a higher flash point of 62° C. compared to Jet A, while the high degree of branching resulted in a freezing point of −53° C. comparable to Jet A, despite the higher average carbon number. However, the isoparaffin branching resulted in low temperature viscosity at −40° C. being out of spec (24 cSt, spec max 12 cSt), with a strong temperature dependence relative to the Fast Track VFA-SAF and Jet A (see Table 6).

Fuel property tests (see Table 7) determined an upper blend limit of 30 vol % for Aldol Condensation VFA-SAF, with viscosity at −40° C. as the limiting fuel property. The higher carbon number distribution increased the boiling point distribution upon blending with Jet A, while the blend's flashpoint of 53° C. was within the typical range of fossil jet. Freezing point was modestly improved to −53° C., while specific energy density increased to 43.4 MJ/kg that was above the typical range of fossil jet. Normalized sooting concentration of the 30 vol % blend was reduced by 15% relative to fossil Jet A.

Figure 9:
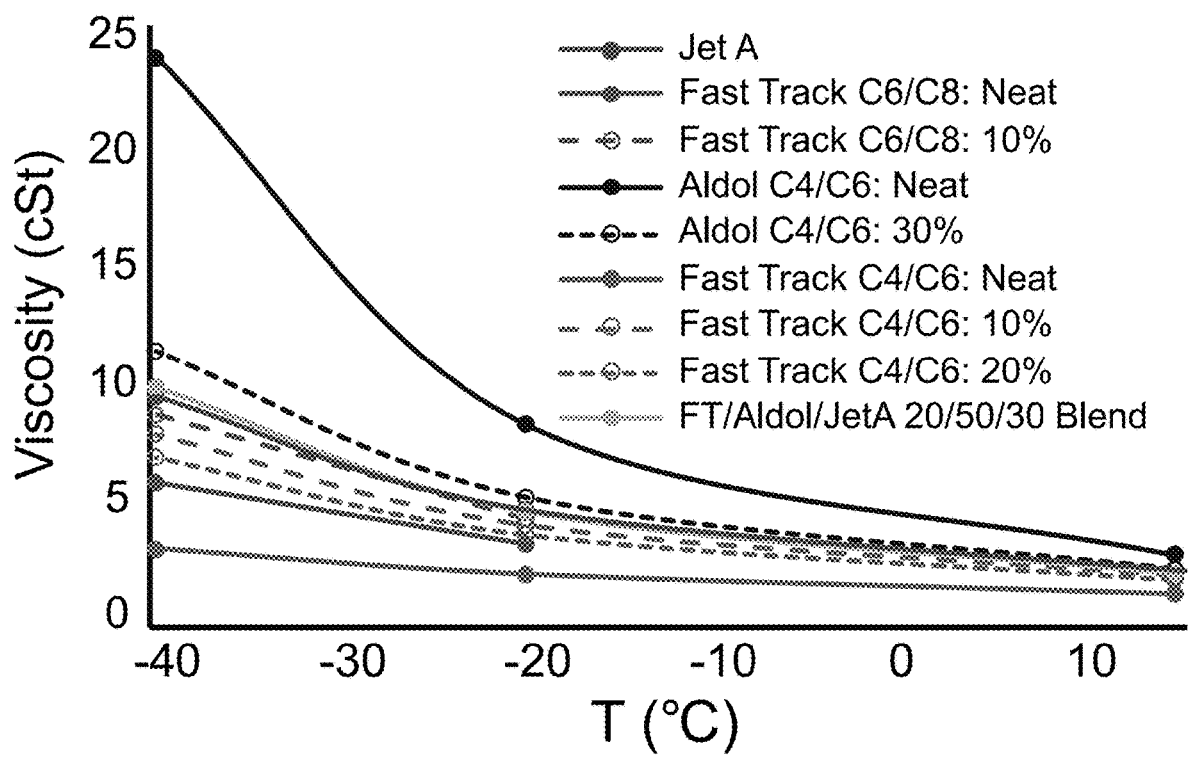
FIG. 9 illustrates viscosity as a function of temperature for the Fast Track $C_6/C_8$ VFA-SAF, Fast Track $C_4/C_6$ VFA-SAF, Aldol Condensation $C_4/C_6$ VFA-SAF, and Fast/Aldol $C_4/C_6$ VFA-SAF, according to some embodiments of the present disclosure.

Synergistic blending was then evaluated by combining Fast Track and Aldol Condensation VFA-SAF due to their complementary limiting fuel properties. Samples were produced from the same $C_4$/$C_6$ VFA starting material using ketones ≥$C_8$ for Fast Track, and ketones <$C_8$ for Aldol Condensation. Since flashpoint is typically dictated by the lowest boiling components in the mixture, a 20 vol % blend limit was maintained for Fast Track VFA-SAF (see Tables 6 and 8). In contrast, viscosity is a function of the overall hydrocarbon mixture composition; therefore, it was reasoned that the low viscosity Fast Track normal paraffins would offset the high-viscosity Aldol Condensation isoparaffins. FIG. 9 illustrates viscosity as a function of temperature for the Fast Track $C_6$/$C_8$ VFA-SAF, Fast Track $C_4$/$C_6$ VFA-SAF, Aldol Condensation $C_4$/$C_6$ VFA-SAF, and Fast/Aldol $C_4$/$C_6$ VFA-SAF, according to some embodiments of the present disclosure. As shown in Table 6, co-blending normal 20 vol % Fast Track VFA-SAF increased the blend limit of Aldol Condensation VFA-SAF from 30 vol % to 50 vol %, resulting in an overall VFA-SAF content of 70 vol %. Fuel property measurements (see Table 7) determined the 70 vol % blend displayed a reduced freezing point of −61° C. and significantly increased energy density of 43.7 MJ/kg, well above the typical range for fossil jet. Normalized soot concentration decreased by 34%, consistent with the blend's reduced aromatic content of 5.8%, which remains above the minimum currently required for polymer seal swell. Cetane number of the blend increased well above the range of conventional jet fuel (CN=64), while surface tension decreased below the typical range. The latter may have positive implications on ignition quality due to improved (decreased droplet size) fuel spray properties.

FURTHER EXAMPLES

Example 1: In this example, a wet (e.g. 10 wt % and 90 wt % water) waste-derived VFA mixture included C2-C5 acids, with a relatively low C2 concentration of about 7 wt % was used as a feedstock to produce fuels as described herein. For this example, the major components in the final resultant fuel, having physical properties and performance metrics similar to jet fuel, referred to herein as a "biojet blendstock", were identified as iso-paraffins. This example highlights the ability of the chemistry and methods described herein to adjust C2 acid levels to tune the iso-paraffin-to-cycloparaffin ratio for a desired fuel blendstock composition and fuel properties. The VFA biojet blendstock directly obtained from catalytic upgrading was shown to have favorable jet fuel properties, alleviating the need for downstream separation steps, such as distillation. Further, the biojet blendstock included a high energy density, a high specific energy, a high cloud point, and a flash point comparable to commercial Jet A, with a lower intrinsic sooting tendency. Additionally, three surrogate fuels (where "surrogate" is defined as a simple fuel mixture of known components designed to emulate the composition and fuel properties of a complex fuel mixture) were prepared from commercially available cycloparaffins and iso-paraffins identified from other VFA and municipal solid waste (MSW) biojet samples. The biojet surrogate fuel properties were characterized to serve as a baseline for other blend studies and to inform future process designs.

Wet waste-derived VFA upgrading to biojet blendstock: Volatile fatty acids (VFAs) derived from wet food waste were supplied by Earth Energy Renewables. A sample used for conversion was a neat acids mixture comprising of C2-C5 carboxylic acids. This waste-derived VFA feed had a relatively low C2 acid content relative to the higher-carbon carboxylic acids and contained branched VFAs including iso-C4 and iso-C5 acids (see Table 10).

TABLE 10

Model and wet waste-derived VFA composition (wt %).

| VFA | C2 | C3 | C4 | iso-C4 | C5 | iso-C5 | Total |
|---|---|---|---|---|---|---|---|
| Model mixture | 37.0 | 27.1 | 17.0 | 0 | 19.0 | 0 | 100.1 |
| Waste-derived | 6.6 | 34.1 | 28.0 | 2.8 | 21.3 | 8.1 | 100.9 |

In these examples, as described above, wet waste-derived VFAs were upgraded to biojet blendstock through an integrated catalytic conversion process aimed at increasing the carbon number and degree of branching, as well as removing oxygen to produce jet range hydrocarbons. This process included three sequential conversion steps: ketonization, aldol condensation, and hydrodeoxygenation (HDO), as described above. Ketonization occurred with neat carboxylic acids to generate a self-separating ketone organic phase and aqueous phase. Ketones were then coupled by aldol condensation in an organic solvent to form alkenones (i.e. enones). Following condensation, the solvent and unreacted ketones were separated from the alkenone product and recycled. Neat alkenones then underwent HDO to generate the final hydrocarbon product, including iso-paraffins and cycloparaffins. A final distillation step is not necessarily required, and was not needed in this example, with the full HDO product being used for jet fuel. This provides a significant advantage because it improves overall VFA-to-jet yield and reduces energy consumption for separation.

Figure 10:
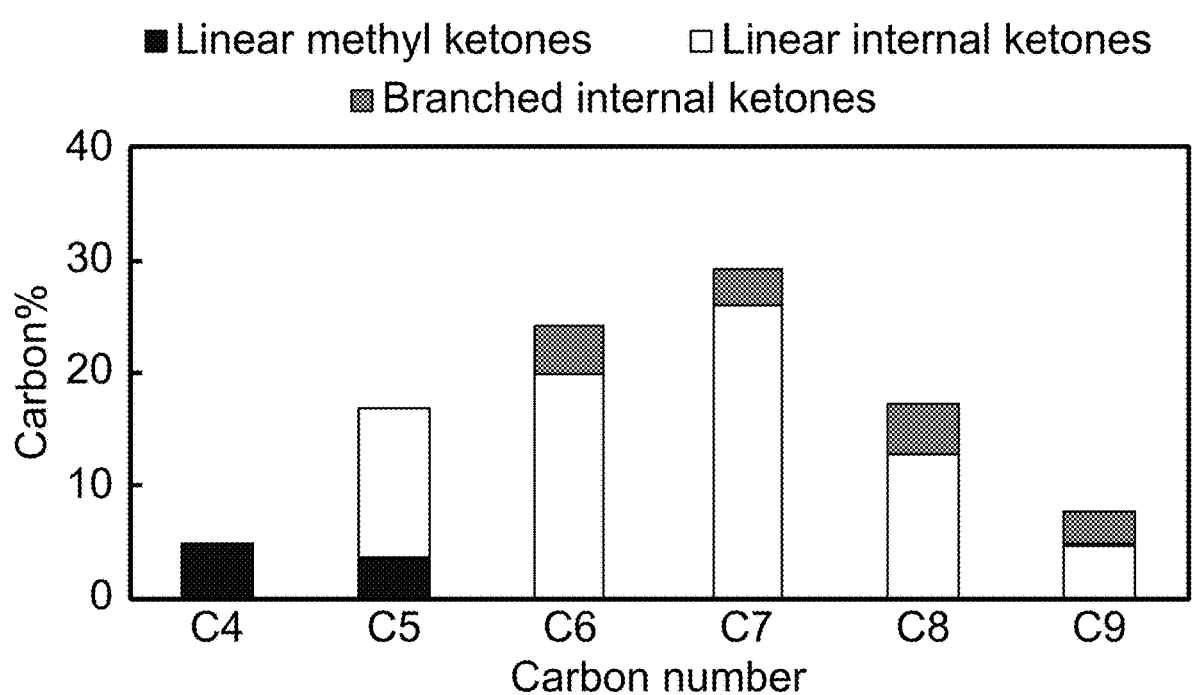
FIG. 10 illustrates carbon distribution of an exemplary ketone product obtained from the ketonization of wet waste-derived VFAs, according to some embodiments of the present disclosure. Ketonization conditions: $ZrO_2$ catalyst loading 3 g, argon flow 100 sccm at 1 atm, bed temperature 435° C., WHSV 3.8 h$^{-1}$ based on VFA mass flow rate.

For this example, VFAs were selectively converted to ketones in a continuous flow reactor, extending the carbon number range from C2-C5 for the starting VFAs to longer-chain ketones with carbon numbers up to C9 (see FIG. 10). VFAs conversion was nearly complete for over 8 hours of time-on-stream with an overall mass recovery of ~100%. The mass yield of organic phase ketone product was 67%, close to the theoretical yield of 63%. The gas-phase product was primarily $CO_2$, with light hydrocarbon products accounting for <1% of the total product. The mixed ketone products consisted of a range of structures, including 9 wt % linear methyl ketones, 76 wt % linear internal ketones, and 14 wt % branched internal ketones. Based on the high fraction (90 wt %) of internal ketones, it may be expected that further conversion of the mixed ketone product may result in a majority of iso-paraffins in the final hydrocarbon blendstock.

Figure 11A:
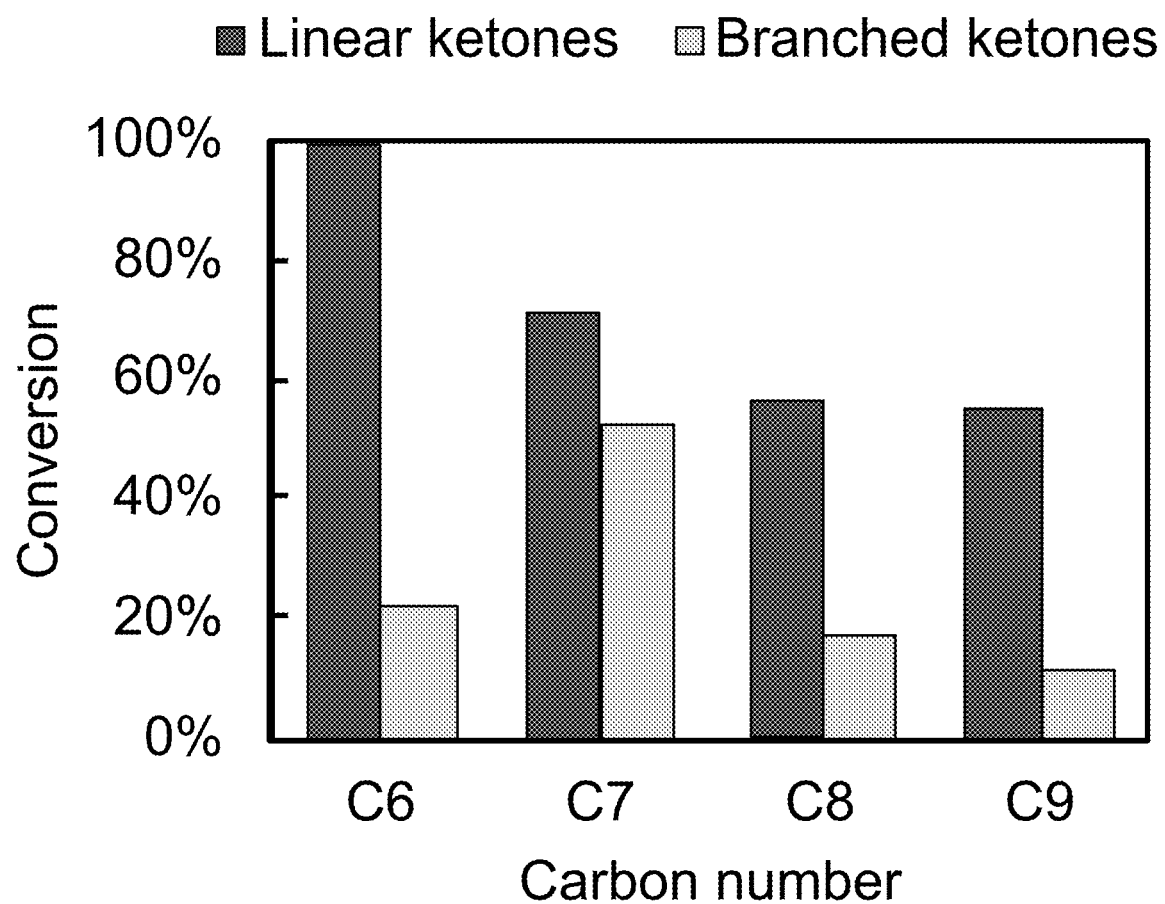
FIG. 11A illustrates conversion of longer-chain ketones to produce alkenone products, according to some embodiments of the present disclosure. Condensation conditions: 30 g feed comprised of 20 wt % ketone in heptane, 1.5 g $Nb_2O_5$, initial helium headspace at atmospheric pressure, 180° C., 24 hours, stirring 800 rpm. Conversion of ketones smaller than C6 not reported due to interference between heptane solvent and these compounds during GC analysis.

Referring again to FIG. 2, aldol condensation of the mixed ketone product to alkenones (typically C8-C18) was performed in a batch reactor to further increase carbon number and reduce oxygen content via dehydration reactions. $Nb_2O_5$ was chosen as the catalyst for condensation due to its high activity for internal ketone condensation. Ketone conversion was revealed to depend on molecular structure, with ketone conversion varying between 12% and 100%. For linear ketones, ketone conversion appeared to increase with decreasing ketone carbon number, while this trend was not observed for branched ketones (see FIG. 11A). Branching imparted steric hindrance and significantly reduced condensation reactivity of branched ketones compared to linear ketones. Loss of carbon to the gas-phase products was insignificant during condensation.

Figure 11B:
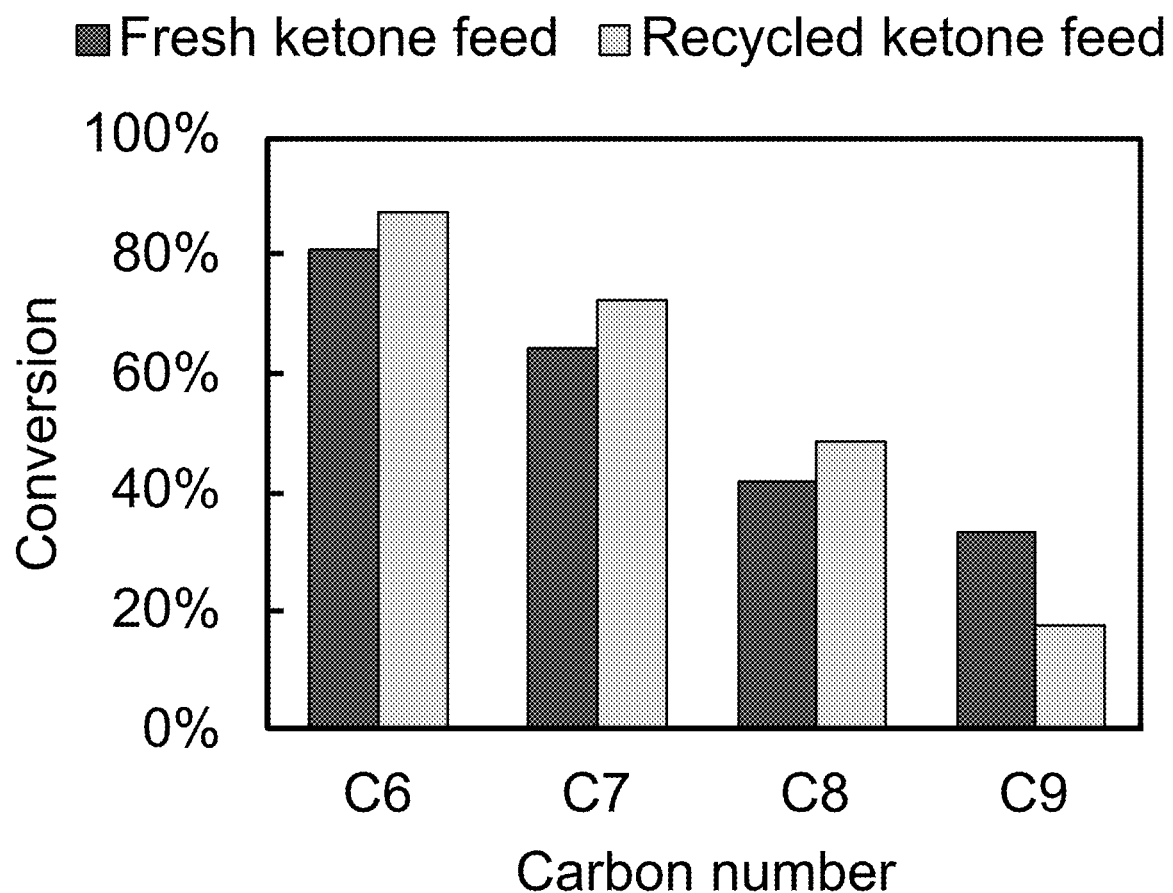
FIG. 11B illustrates a comparison of longer-chain ketone conversion in fresh ketone feed and in recycled ketone feed during condensation, according to some embodiments of the present disclosure. Conditions listed above for FIG. 12A.

Solvent and unreacted ketones were separated from higher-boiling alkenone products using spinning-band distillation. To evaluate the feasibility of ketone recycling, the recovered ketones were mixed with the recovered solvent at 20 wt % and tested for condensation performance. Under similar reaction conditions, longer-chain ketones exhibited slightly higher conversion in the recycled ketone feed than in the fresh ketone feed (see FIG. 11B). The observed higher conversion may be due to less competition from the more reactive linear methyl ketones at a lower fraction in the recycled ketone feed. These results suggest that ketone recycling is promising to improve the conversion of complex ketone mixtures derived from wet waste-VFAs for higher overall product yield.

Figure 12:
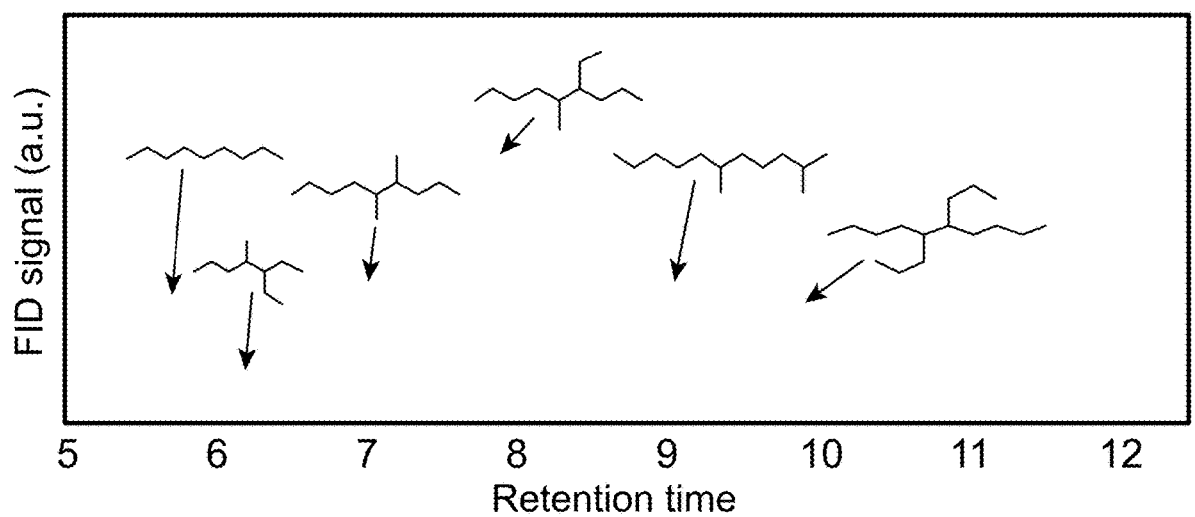
FIG. 12 illustrates GC-Polyarc/FID chromatogram of biojet derived from the HDO process and potential component structure based on library search, according to some embodiments of the present disclosure. HDO conditions: Pt/$Al_2O_3$ catalyst loading 1 g, $H_2$ flow 150 sccm at 500 psi, bed temperature 345° C., WHSV 2.6 h$^{-1}$ based on feed mass flow.

In the HDO conversion step, the oxygen functionality remaining in the alkenones was removed using a continuous flow reactor in the presence of a $Pt/Al_2O_3$ catalyst and $H_2$. This process produced a self-separating hydrocarbon organic phase and aqueous phase, with minimal gas-phase byproduct formation. The integrated catalytic conversion process generated 25 mL of biojet blendstock from wet waste-derived VFAs, meeting the milestone target of ≥20 mL. The biojet blendstock comprises a range of hydrocarbon molecules, the majority of which were identified as iso-paraffins (i.e. branched paraffins) (see FIG. 12). The low concentration of C2 acids in the VFA feed resulted in a low fraction of methyl ketones, which are precursors to cycloparaffins. These results highlight the tunable production of iso-paraffins versus cycloparaffins for desired biojet fuel applications.

Example 1

Fuel properties of wet waste VFA biojet blendstock and blend: The fuel properties of the exemplary VFA biojet blendstock described above were evaluated. The ≥20 mL produced provided sufficient volume to test these fuel properties and for synthesizing a blend containing 10 vol % biojet blendstock in Jet A commercial jet fuel. The results of these tests and comparison with the ASTM D7566-19 jet criteria are reported in Table 11.

TABLE 11

Fuel properties of the model VFA upgrading product, the wet waste-derived VFA biojet blendstock, and the blend (10 vol % wet waste VFA biojet blendstock in Jet A) are shown alongside the selected jet fuel criteria.

| Property | Jet Criteria | Jet A | Model VFA Biojet | Waste VFA Biojet (Aldol route) | 10 vol % VFA Blend[a] |
|---|---|---|---|---|---|
| $T_{cloud\ or\ freeze}$ (° C.) | <−40 | −52 | −42 | <−75 | −51 |
| T10 (° C.) | <205 | 176 | 183 | 199 | 178 |
| T50 (° C.) | — | 205 | 235 | 223 | 208 |
| T90 (° C.) | — | 244 | 272 | 274 | 247 |
| $T_{boil}$ or T100 (° C.) | <300 | 269 | 303 | 311 | 276 |
| $T_{flash}$ (° C.) | >38 | 48 | — | 43 | 44 |
| % C | — | 86.1 | 85.9 | 85.0 | 85.7 |
| % O | — | 0 | 0 | 0 | 0 |
| % H | — | 13.9 | 14.5 | 15.2 | 14.0 |
| LHV (MJ/kg) | >42 | 40.0 | 43.6 | 43.4 | 42.9 |
| LHV (MJ/L) | ≥32 | 32.1 | 35.6 | 34.0 | 34.2 |
| Density at RT (g/mL) | 0.775-0.840 | 0.802 | — | 0.784 | 0.798 |
| NSC[c] | <1 | 1.00 | — | 0.67 | 0.97 |

[a] 10 vol % waste-derived VFA Biojet blendstock in Jet A

[b] Normalized soot concentration (Jet A = 1)

As shown, both the model VFA upgrading product and the biojet blendstock meet all jet criteria except for the total boiling point (T100) requirement. However, it should be noted that the VFA biojet blendstock was not fractionally distilled following HDO, and the full crude product was utilized for fuel property analysis. Additionally, while the biojet blendstock T100 overshoots the maximum of 300° C. by 11° C., the 10 vol % blend data shows incorporating VFA biojet blendstock with Jet A does not push this boiling point above the limit. This suggests that at the low blend levels, the neat VFA biojet HDO product remains a promising blendstock candidate. A final distillation may allow for 100% VFA biojet to meet full ASTM specifications. Compared to the model VFA upgrading product, the wet waste VFA biojet blendstock exhibited lower freezing point and energy density. This favorable change is likely due to the high iso-paraffin fraction resulting from low C2 acid content. However, volumetric energy density was reduced, consistent with the high iso-paraffin content. These results illustrate the ability to tailor the VFA acid composition to tune desired fuel properties of the final HDO product.

Figure 13:
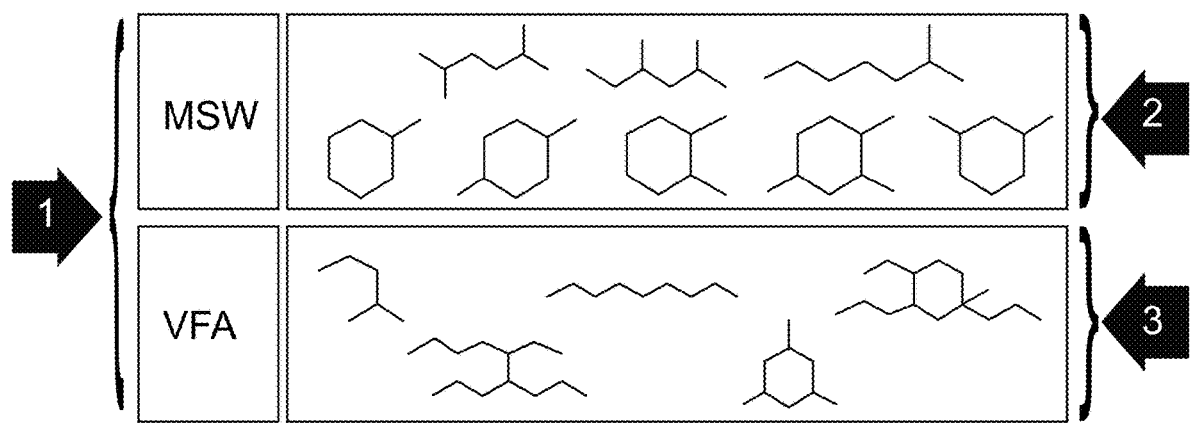
FIG. 13 illustrates compositions of Surrogates 1 (MSW/VFA component combination), 2 (MSW components only), and 3 (VFA components only), according to some embodiments of the present disclosure.

Biojet surrogate blendstocks and fuel properties: Surrogate fuels were then synthesized to evaluate the impact of biojet blendstock composition on fuel properties of interest. The surrogate fuels were a mixture of commercially available hydrocarbons that were representative of those identified in the waste-derived biojet samples produced via the indirect liquefaction of municipal solid waste (MSW, measured properties in Table 12) or the VFA platform. Computational tools and published data were initially leveraged to evaluate the fuel properties of identifiable components within the both VFA and MSW pathway components (see FIG. 13).

TABLE 12

Fuel properties of the municipal solid waste (MSW) upgrading product

| Property | Jet Criteria | MSW Biojet |
|---|---|---|
| $T_{cloud\ or\ freeze}$ (° C.) | <−40 | <−80 |
| $T_{flash}$ (° C.) | >38 | 22 |
| HHV (MJ/kg) | >42 | 47.4 |
| Density at RT (g/mL) | 0.775-0.840 | 0.719 |

Once it was established which hydrocarbon species would likely impact target fuel properties, three surrogates were designed to represent the VFA and MSW biojet products. Surrogate 1 was a selection of commercially available linear, branched, and cyclic alkanes seen in the product mixtures of both the VFA and MSW pathways. Surrogate 2 contained representative compounds from only the MSW pathway, and Surrogate 3 was derived from only the VFA pathway.

Fuel properties measurements of the three surrogates largely met jet criteria (see Table 13). However, a shortcoming of Surrogates 1 and 2 is the flashpoint being below 38° C. It is apparent that the MSW products depress the flashpoint of the mixed MSW and VFA Surrogate 2, when comparing the high flashpoint of Surrogate 3 (VFA only). However, the MSW pathway may still be a viable route if the flashpoint remains above the cutoff when blended with commercial jet fuel, or if lower boiling components can be easily distilled out of the mixture. Surrogate 2 also displays a volumetric energy density barely below the 32 MJ/L cutoff, but this is unlikely to affect properties of the final blend. Surrogate 3, comprising products of the VFA pathway, appears to have the advantage of higher-carbon compounds and therefore meets the measured jet criteria.

TABLE 13

Fuel properties of Surrogates 1, 2, and 3 shown alongside the selected jet fuel criteria.

| Property | Jet Criteria | Surrogate 1 | Surrogate 2 | Surrogate 3 |
|---|---|---|---|---|
| $T_{cloud\ or\ freeze}$ (° C.) | <−40 | <−75 | <−75 | <−75 |
| T10 (° C.) | <205 | 110.2 | 119.9 | 90.2 |
| $T_{boil}$ or T100 (° C.) | <300 | 255.7 | 149.7 | 260 |
| $T_{flash}$ (° C.) | >38 | <27 | <27 | >105 |
| LHV (MJ/kg) | >42 | 43.25 | 43.08 | 43.80 |
| LHV (MJ/L) | >32 | 32.20 | 31.96 | 32.73 |
| YSI | <150 | 66.50 | 61.70 | 76.60 |

Example 2

Figure 14:
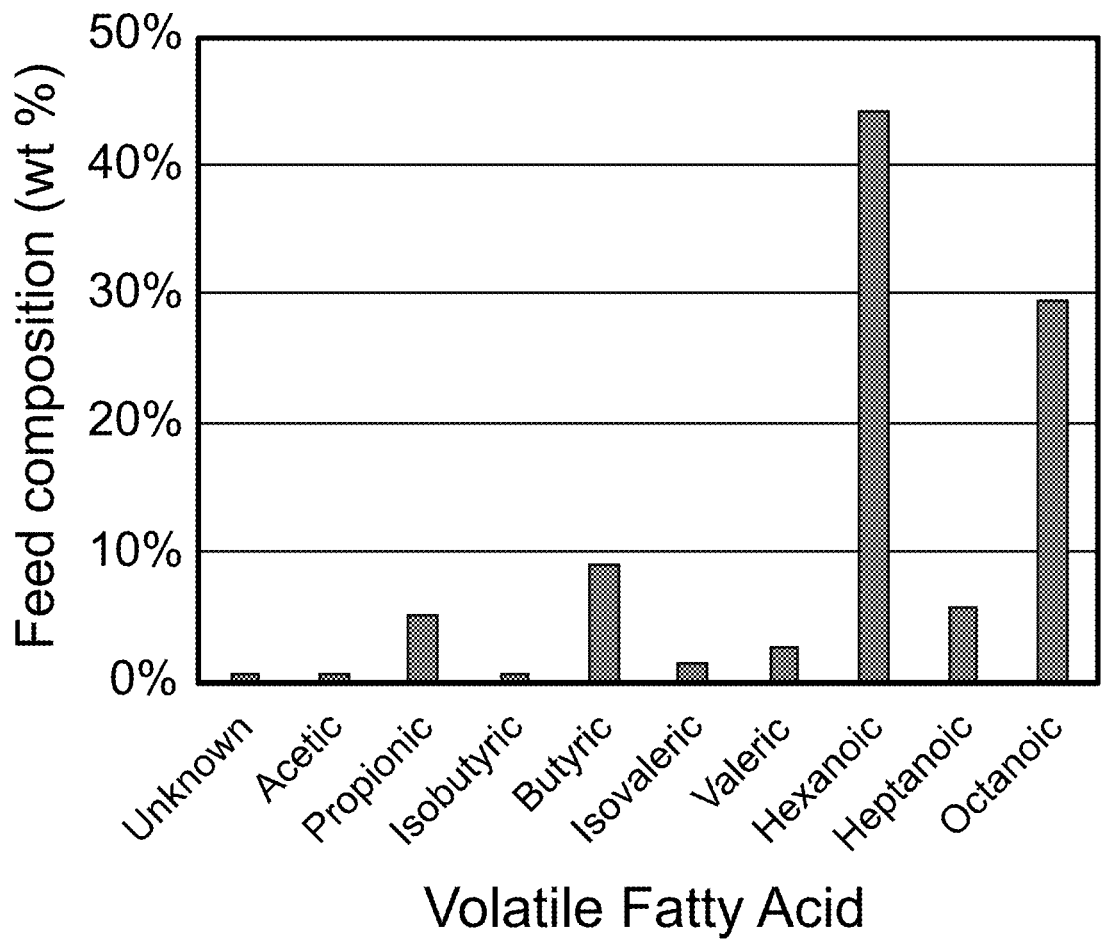
FIG. 14 illustrates the distribution of catalytically upgraded bioderived materials, according to some embodiments of the present disclosure.

As shown herein, reaction chemistry enabling the catalytic upgrading of VFAs to useful fuels has been substantially advanced, including the use of continuous flow reactors. In some embodiments of the present disclosure, an enriched $\geq C_6$ VFA fraction was utilized to allow for the entire VFA hydrocarbon biofuel to fall into carbon distribution range of biojet for VFA-SAF, with minimum to no production of VFA-naphtha. Based on process economics and desired fuel production targets (e.g., SAF vs. naphtha), the incoming VFA distribution for catalytic upgrading may be readily tailored for neat VFAs from fermentation with a C3-C5 and $\geq C6$ fraction to allow fuel property tuning. Near theoretical conversion of EER waste-derived VFA feedstocks has been demonstrated, with an example VFA profile shown in FIG. 14.

Figure 15:
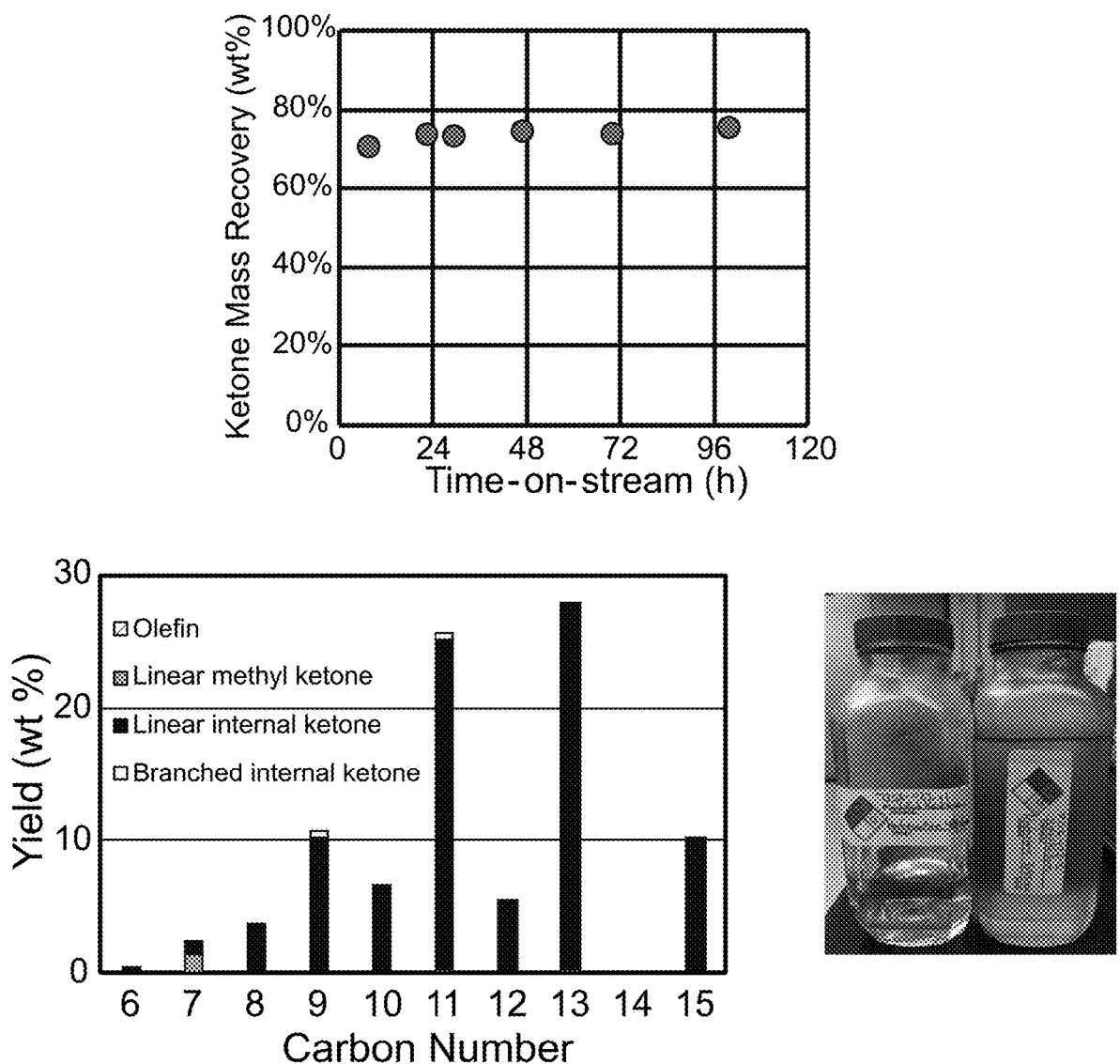
FIG. 15 illustrates a ketone distribution and liquid product samples obtained from processing VFAs by ketonization, with the initial VFA profile shown in FIG. 14, according to some embodiments of the present disclosure. Reaction conditions were as follows: Catalyst loading 5 g amphoteric metal oxide catalyst, Ar flow 167 sccm at 1 atm, bed temperature 350° C., WHSV 3.8 h$^{-1}$ based on VFA mass flow rate. Stable ketone sample profiles and mass balances were monitored throughout the 100-h run.
Figure 16:
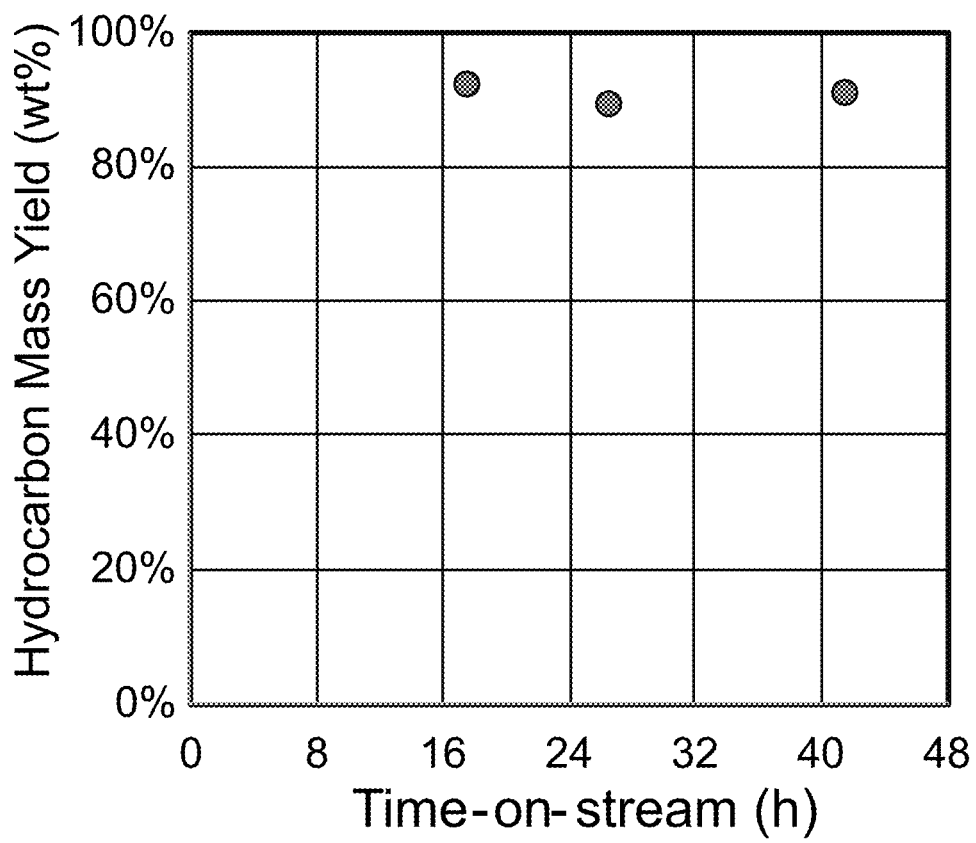
FIG. 16 illustrates a stable mass balance and liquid product sample when processing VFA-derived ketones by HDO, with the ketone profile shown in FIG. 15, according to some embodiments of the present disclosure. Reaction conditions were as follows: Catalyst loading 5 g metal supported catalyst, $H_2$ flow 300 sccm at 34 atm, bed temperature 345° C., WHSV 4.4 h$^{-1}$ based on liquid feed mass flow rate. Stable HDO sample profiles and mass balances were monitored throughout the run.
Figure 16:

As shown herein, VFA ketonization has been demonstrated with stable performance for over 100 hours of TOS and near theoretical ketone mass yields of ~65% (see FIG. 15). Elemental analysis demonstrated that the VFA-derived ketones displayed lower impurity levels. The resulting mixed ketones have demonstrated stable HDO performance for over 24 hours of TOS with near theoretical paraffin mass yields of ~90%, as shown in FIG. 16.

TABLE 14

Impurity analysis of VFA feed (FIG. 14) and post-ketonization product (FIG. 15).

| | Elemental Analysis (ppm) | | | | | | | | | | | | |
|---|---|---|---|---|---|---|---|---|---|---|---|---|---|
| | Al | B | Ca | Fe | K | Mg | Mn | Na | P | S | Si | Zn | Zr |
| EER C-C8 VFA Blend | <1.8 | <4.2 | 0.8 | 3.0 | 236 | 4.1 | <0.2 | 105 | <10 | 32 | <1 | <1 | <1 |
| VFA-Derived Ketones | <1 | <1 | <0.1 | <1 | <1 | <0.1 | <0.2 | <1 | <10 | <10 | <1 | <1 | <1 |

Figure 17:
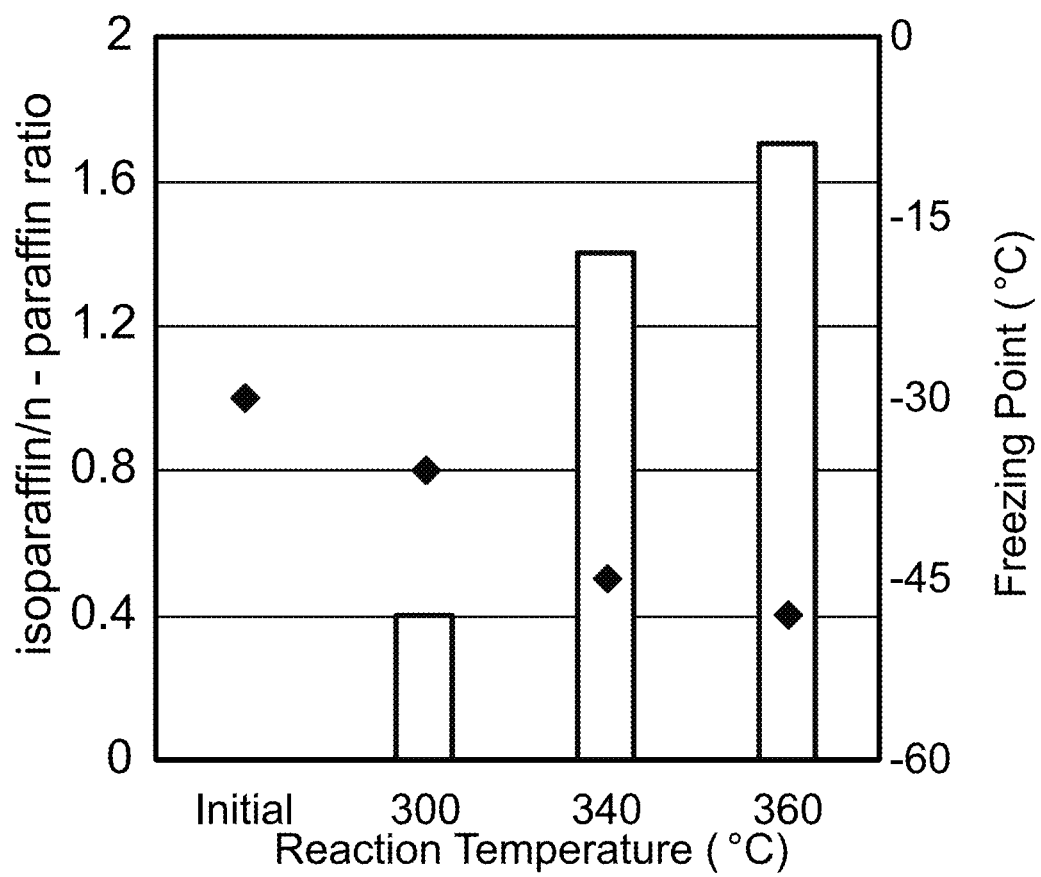
FIG. 17 illustrates the partial conversion of n-decane into iso-paraffins through hydroisomerization with corresponding freezing point reductions, according to some embodiments of the present disclosure. Reaction conditions were as follows: Catalyst loading 1 g metal supported catalyst, $H_2$ flow 40 sccm at 1 atm, varied bed temperature, WHSV 1.9 $h^{-1}$ based on n-decane mass flow rate.
Figure 18:
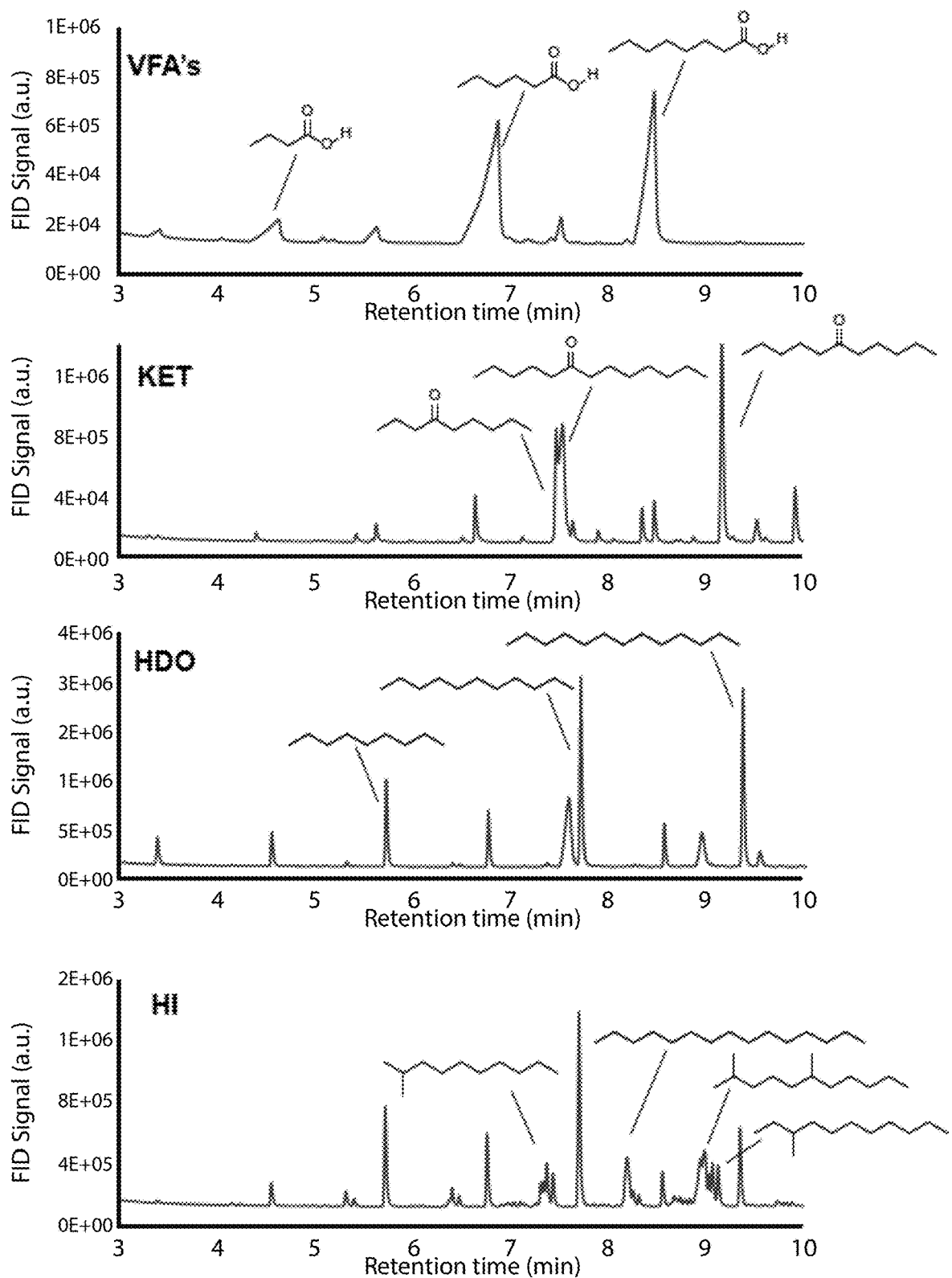
FIG. 18 illustrates GC chromatogram traces of when catalytically upgrading neat VFAs via catalytic ketonization, hydrodeoxygenation, and isomerization, with major compounds identified by GC-MS, according to some embodiments of the present disclosure.

As shown herein, hydroisomerization reactions have been completed to demonstrate improvements in freezing point with model paraffins (see FIG. 17) that was applied to the EER ketone HDO product. Varying process conditions such as the bed temperature and hydrogen pressure led to various levels of isomerization to influence cold flow properties. Isomerization of the EER VFA-derived HDO product was performed at 340° C. to generate a final mixed paraffin stream with 95% mass recovery and GC chromatogram trace shown in see FIG. 18.

The final mixed paraffin VFA-SAF was then evaluated for its predicted and measured fuel properties when blended into Jet A at 10% volume. Promisingly, no distillation was performed and the neat VFA hydrocarbon product was blended and tested following HDO and ISO. Fuel property predictions utilized UDRI in-house blending model, which showed all of the evaluated properties would meet ASTM "Fast Track" blend spec. Flash point and freezing point were the fuel properties of most concern, as these are both highly dependent on the VFA-SAF carbon number distribution and degree of isomerization. Experimental measurements of the VFA-SAF 10% blend confirmed that flash point and freezing point specifications were met when blending the HDO and ISO samples with Jet A, as shown in Table 15, with comparable energy density and boiling point distribution. These conversion and fuel property testing results highlight the promise of the VFA-SAF pathway for scale-up and ASTM "Fast Track" qualification.

TABLE 15

ASTM requirements of aviation turbine fuels per D1655 and measured fuel properties of conventional Jet A and the 10% VFA-SAF blend produced in FIGS. 14-18.

| Jet Fuel Property | ASTM D1655 Spec | Conventional Jet A | 10% VFA-SAF HDO | 10% VFA-SAF HDO-ISO |
|---|---|---|---|---|
| Density at 15° C. | 775 to 840 g/L | 803 g/L | 798 g/L | 798 g/L |
| Viscosity at −20° C. | max 8.0 cSt | 4.5 cSt | 4.38 cSt | 4.33 cSt |
| Flash Point | ≥38° C. | 48° C. | 48° C. | 48° C. |
| Freezing Point | ≤−40° C. | −51° C. | −47° C. | −51° C. |
| Higher Heating Value* | N/A | 45.95 MJ/kg | 46.22 MJ/kg | 46.17 MJ/kg |
| T0 | report | 159.2 | 151.1 | 148.5 |
| T10 | max 205° C. | 176.8 | 175.3 | 174.4 |
| T20 | report | 185.4 | 184.8 | 183.6 |
| T50 | report | 205.4 | 205.8 | 204.4 |
| T90 | report | 244.6 | 242.7 | 241.9 |
| T100 | max 300° C. | 270.5 | 270.3 | 270.4 |

*Higher heating value reported due to pending C/H analysis for VFA-SAF

Tables 16 and 17 summarize fuel property measurements for major VFA biojet components and fuel property measurements for major MSW biojet components, respectively, according to some embodiments of the present disclosure.

TABLE 16 fuel property measurements for major VFA biojet components

| | $T_{boil\ or\ 90}$ (° C.) | $T_{flash}$ (° C.) | Density @RT (kg/m3) | $T_{freeze/cloud}$ (° C.) | Net HOC (LHV, MJ/kg) | Yield Sooting Index | Cetane Number |
|---|---|---|---|---|---|---|---|
| 2-methylpentane | 56 | −31 | 700 | −106 | 46 | 36 | 32 |
|  | 60 | −7 | 670 | −154 | 48 | 37 | 35 |
| 3-methylheptane | 106 | 8 | 700 | −80 | 46 | 50 | 35 |
|  | 118 |  | 705 | −100 | 48 | 49 | 45 |
| 4-methylnonane | 152 | 34 | 700 | −55 | 45 | 64 | 40 |
|  | 166 |  | 730 | −99 |  |  |  |
| 5-methylundecane | 194 | 57 | 800 | −32 | 45 | 78 | 47 |
| 3-ethyl-4-methylheptane | 138 | 29 | 700 | −66 | 45 | 78 | 40 |
|  | 221 |  | 747 |  |  |  |  |
| 5-ethyl-4-propylnonane | 221 | 74 | 800 | −20 | 45 | 94 | 46 |
|  |  |  |  |  |  | 98 |  |
| 5-butyl-6-propyldecane | 274 | 108 |  | 12 | 45 | 12 | 50 |
| 1-Nonane | 143 | 27 | 700 | −56 | 45 | 51 | 70 |
|  | 151 | 31 | 718 | −53 |  | 50 | 61 |
| Mesitylene | 170 | 42 | 864 | −22 | 41 | 322 |  |
|  | 165 | 53 | 900 | −45 |  | 311 |  |
| 1,1,3-trimethylcyclohexane | 134 | 19 | 800 | −45 | 44 | 80 | 27 |
|  | 137 |  | 778 | −66 | 47 | 84 |  |
| 1,3-diethyl-1,4-dimethylcyclohexane | 193 | 56 |  | −13 | 44 | 106 | 33 |
| 4-ethyl-1-methyl-1,3-dipropylcyclohexane | 250 | 93 |  | 20 | 44 | 128 | 40 |
|  |  |  |  |  |  | 148 |  |
| 1,3-dibutyl-1-methyl-4-propylcyclohexane | 298 | 124 |  | 51 | 44 | 149 | 47 |
| 1,1,3-triethyl-2,4,6-trimethylcyclohexane | 239 | 85 |  | 13 | 44 | 138 | 58 |

TABLE 16-continued fuel property measurements for major VFA biojet components

| | $T_{boil\ or\ 90}$ (° C.) | $T_{flash}$ (° C.) | Density @RT (kg/m3) | $T_{freeze/cloud}$ (° C.) | Net HOC (LHV, MJ/kg) | Yield Sooting Index | Cetane Number |
|---|---|---|---|---|---|---|---|
| 2,4,6-triethyl-1,1,3-tripropylcyclohexane | 331 | 145 | | 74 | 44 | 181 | 82 |
| 1,1,3-tributyl-2,4,6-tripropylcyclohexane | 401 | 190 | | 128 | 44 | 223 | 103 |

TABLE 17 fuel property measurements for major MSW biojet components

| | $T_{boil\ or\ 90}$ (° C.) | $T_{flash}$ (° C.) | Density @RT (kg/m3) | $T_{freeze/cloud}$ (° C.) | Net HOC (LHV, MJ/kg) | Yield Sooting Index | Cetane Number |
|---|---|---|---|---|---|---|---|
| 2,5-dimethylhexane | 109 | 1 | 700 | −92 | 46 | 55 | 27 |
| | 108 | 26 | 694 | −91 | 48 | 56 | |
| 2,4-dimethylhexane | 109 | 1 | 700 | 701 | −92 | 55 | 27 |
| | 109 | 10 | 701 | | 48 | 56 | |
| 2-methylheptane | 109 | 4 | 700 | −80 | 46 | 50 | 49 |
| | 116 | 4 | 698 | −109 | 48 | 49 | |
| 2,3-dimethylhexane | 109 | 1 | 700 | −92 | 46 | 55 | 25 |
| | | | 710 | | 48 | | |
| 3-methylheptane | 109 | 5 | 700 | −80 | 46 | 50 | 35 |
| | 118 | 1 | 705 | −121 | 48 | 49 | |
| 2,2,3-trimethylhexane | 129 | 14 | 700 | −73 | 45 | 68 | 20 |
| | | | | −79 | 48 | | |
| 2,5-dimethylheptane | 131 | 18 | 700 | −79 | 45 | 62 | 35 |
| | 136 | 23 | 720 | | | | |
| 2,6-dimethylheptane | 131 | 16 | 700 | −79 | 45 | 62 | 35 |
| | | | 706 | −103 | | | |
| 2-methyloctane | 132 | 20 | 700 | −68 | 45 | 57 | 57 |
| | 143 | 26 | 714 | −80 | 48 | | |
| 3,5-dimethyloctane | 132 | 25 | 700 | −67 | 45 | 68 | 30 |
| | 159 | | 740 | | | | |
| 2,6-dimethyloctane | 154 | 33 | 700 | −67 | 45 | 68 | 41 |
| | 159 | | 730 | | | | |
| 2-methylnonane | 155 | 35 | 700 | −55 | 45 | 63 | 63 |
| | 166 | | 726 | −75 | 48 | | |
| 3-methyloctane | 132 | 21 | 700 | −68 | 45 | 57 | 44 |
| | 144 | 32 | 720 | −108 | | | |
| 2,7-dimethyloctane | 154 | 32 | 700 | −67 | 45 | 68 | 41 |
| | 159 | | 720 | −55 | 48 | | |
| 1,3-dimethylcyclohexane | 124 | 11 | 800 | −65 | 45 | 67 | 22 |
| | 121 | 9 | 784 | −76 | 46 | | |
| 1-ethyl-2-methylcyclopentane | 401 | 9 | 800 | −65 | 45 | 67 | 29 |
| | | | | −106 | 47 | | |
| Methylcyclohexane | 124 | 5 | 800 | −74 | 45 | 56 | 24 |
| | 101 | −6 | 774 | −126 | 47 | 54 | |
| 1,4-dimethylcyclohexane | 124 | 11 | 800 | −66 | 45 | 67 | 22 |
| | 120 | | 761 | −87 | 46 | 67 | |
| 1,2-dimethylcyclohexane | 124 | 12 | 800 | −66 | 45 | 67 | 22 |
| | 123 | 15 | 796 | −50 | 47 | | |
| 1,2,4-trimethylcyclohexane | 143 | 24 | 800 | −58 | 45 | 79 | 26 |
| | 144 | 19 | 786 | −84 | 47 | 83 | |
| 1,1,4-trimethylcyclohexane | 147 | 28 | 800 | −45 | 45 | 78 | 27 |
| | | | 765 | | | | |
| 1-ethyl-4-methylcyclohexane | 147 | 28 | 800 | −54 | 45 | 74 | 31 |
| | | | 790 | −80 | | | |
| 1,1,2,3-tetramethylcyclohexane | 166 | 40 | 800 | −37 | 45 | 90 | 22 |
| 2-ethyl-1,3-dimethylcyclohexane | 166 | 39 | 800 | −46 | 45 | 90 | 22 |
| | | | 767 | | | | |
| 1-methyl-2-propylcyclohexane | 177 | 42 | 800 | −42 | 45 | 80 | 35 |
| | | | 813 | | | | |

Examples of Alcohols to Iso-Paraffins

Referring to Reactions 5 and 6 above, alcohol dehydration (Step 2) was conducted in a 0.5" stainless steel flow reactor tube, enclosed in a clamshell furnace (Thermcraft) (Carbolite Gero), and dual thermocouples measuring the temperature along the heated inlet and in the center of the catalyst bed. In a typical experiment, the reactor vessel was packed with 2 g of sieved Purolite CT482DR, diluted with silica with 1:1 volume, filled with and inert glass beads and quartz wool at both ends to hold the catalyst bed in place. Prior to the reaction, the Purolite catalyst was pretreated by washing with distilled water until acid leaching was no longer observed, subsequently dried overnight at 393 K and stored in a desiccator. The alcohol feed contained 3-pentanol, 3-hexanol, and 4-heptanol with 3:10:37 molar ratio and was fed to the reactor system by a HPLC pump (Chromtech) at 0.05 mL/min. He gas was introduced through a calibrated mass flow controller (Brooks) at 60 mL/min. Pressure in the reactor was maintained at about atmospheric pressure by a back-pressure regulator (Swagelok). Gas flow and system pressure were controlled by valve controller. Reactor temperature was set at 423K, controlled and monitored via a dual thermocouple by a power controller. Liquid effluent samples was collected from the knockout pot periodically. Aqueous and organic layers were separated and analyzed by GC/MS and GC/Polyarc-FID. The organic layers were combined and used as feed for oligomerization. Alkene yield was defined by, $$\text{Alkene carbon yield \%} = \frac{n\_carbon_{alkene}}{n\_carbon_{alcohol\ of\ the\ same\ carbon\ number}} \times 100\%.$$

Oligomerization (Step 3) was carried out in a 75 mL batch reactor vessel (multi-series batch 5000 Parr), containing the feed solution (20 mL of organic products from step 1) and 12 wt % of pretreated Purolite. The reactor was sealed, purge three times with He and pressurized to 20 bar He before heating to the desired temperature of 423K and stirred at 800 rpm. After about 5.5 hours of reaction time, the reactors were quenched in an ice bath to stop the reaction. The spent catalyst was filtered and washed with acetone while the liquid products were collected and analyzed by GC/MS and GC/Polyarc-FID.

Hydrogenation was (Step 4) conducted in the same 75 mL batch reactor vessel described above. Feed solution (15 mL of product from step 2) and 10 wt % of 5% $Pt/Al_2O_3$ were loaded into the reactor vessel, purged with He and pressurized to 20 bar $H_2$. The reaction was set at 383 K for about 11 hours. Thereafter, the reactor was quenched with a final $H_2$ pressure of about 13 bar and the liquid product was collected and analyzed by GC/MS and GC/Polyarc-FID and GCxGC (UDayton).

Figure 19:
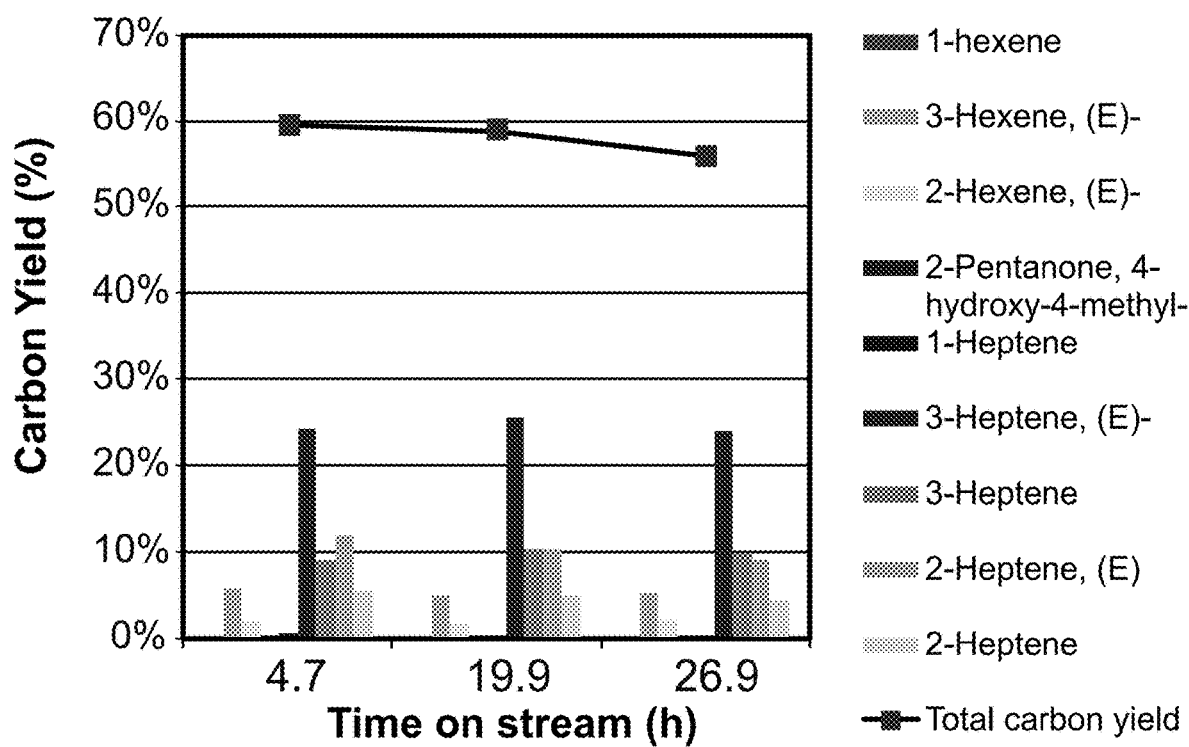
FIG. 19 illustrates alcohol dehydration products, according to some embodiments of the present disclosure. Reaction conditions: 0.05 mL/min alcohol feed (C5:C6:C7=3:10:37 molar ratio), 60 mL/min He, 423 K, 1 atm.

No $C_5$-$C_7$ alcohols were detected after the alcohol dehydration step, indicating full conversion. The organic product contained >99% $C_6$-$C_7$ alkenes isomers and stereoisomers (see FIG. 19). No $C_5$ products were identified. Overall carbon yield was ~60% and slightly decreased with longer time on stream. Carbon loss may be due to the combination of carbonaceous laydown and undetectable products in gas phase.

Figure 20:
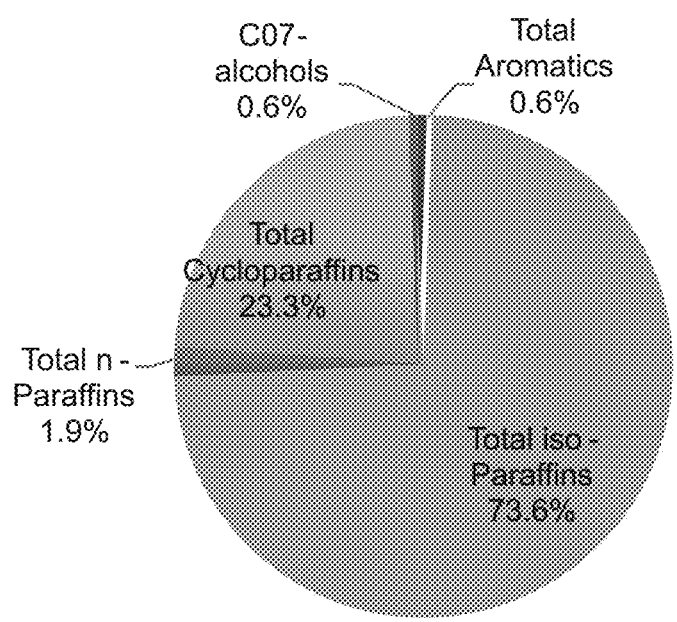
FIG. 20 illustrates a final hydrogenation product composition, obtained from secondary alcohol reactants, according to some embodiments of the present disclosure.

The oligomerization and hydrogenation products contained mostly $C_{12}$-$C_{14}$ hydrocarbon. The individual hydrocarbons were not identified and quantified due to significant overlapping of the peaks in the GC. The product mass recovery was about 68% and about 72% for the oligomerization step and hydrogenation step, respectively. Greater than 90% of the $C_6$ and $C_7$ alkenes were converted to oligomers. The final hydrogenation products were analyzed with GCxGC, and contained mostly iso-paraffin, and cycloparaffins with traces of n-paraffins, aromatics and $C_7$ alcohols with carbon range $C_7$-$C_{30}$ (FIG. 20). Fuel predictions were performed for the final hydrogenation product where the $C_7$ alcohols and >$C_{29}$ hydrocarbons were omitted. Except for higher viscosity and lower flashing point, other fuel parameters including surface tension, density, heat of combustion and cetane number are in acceptable range for jet fuel. In the next step, the hydrogenation products were distilled to separate the <$C_8$ and >$C_{19}$ products and the final jet cut will be re-evaluated with GCxGC and fuel predictions. The last column in Table 5 summarizes the properties of the resultant iso-paraffin, according to some embodiments of the present disclosure.

Methods:

VFAs derived from Food Waste. VFAs derived from food waste were provided by Earth Energy Renewables using their integrated fermentation and VFA recovery pilot facility. In brief, VFAs were produced by arrested anaerobic digestion using mixed microbial consortia. The fermentation was performed at mesophilic temperatures under conditions which suppressed methane formation. Carbon dioxide and residual solids containing cell mass and indigestible organic matter are the two main byproducts from fermentation. Fermentation broth was processed online to recover highly pure ≥$C_3$ VFAs using a proprietary extraction and distillation process. $C_2$ VFA, process water, and caustic were recycled back to fermentation continuously. Recovered VFAs from two food waste fermentation runs were provided, with each run containing two fractions comprised of $C_3$-$C_5$ VFAs and ≥$C_6$ VFAs. Once received at NREL, prior to catalytic upgrading VFA fractions were filtered through a 0.45-μm Nylon membrane vacuum filter from GVS Filter Technology and combined to produce three samples with varying VFA compositional profiles. This included a predominantly $C_4$ VFA sample, $C_4/C_6$ VFA sample, and $C_6/C_8$ VFA sample.

Model VFAs. Model VFAs were purchased from Sigma Aldrich to mimic biogenic VFA profiles. Samples were used as received.

Catalyst Materials. $ZrO_2$ pellets were obtained from Johnson Matthey. Pellets were crushed and sieved to 30-50 mesh particles, and calcined in stagnant air at 500° C. for 2 h before use (5° C./min ramp to temperature). Niobic acid hydrate (HY-340) was obtained from CBMM and used as received. $Pt/Al_2O_3$ catalyst was prepared with chloroplatinic acid hexahydrate obtained from Sigma Aldrich and $Al_2O_3$ pellets obtained from Alfa Aesar.

Fossil Jet Fuel. The fossil jet fuel used as a blending base fuel was required to represent an "average" aviation fuel with respect to physical and chemical properties. The selected POSF 10325 Jet A was source directly from the Shell Mobile without exposure to the pipeline infrastructure.

VFA Characterization. Water content of VFA samples was determined using Karl-Fischer titration on a Metrohm 870 KF Titrino plus using the Aquastar CombiTitrant 5 solvent. Inductively coupled plasma mass spectrometry was performed by Huffman Hazen Laboratories to determine impurity concentrations for several elements in VFA, ketone and hydrocarbon samples.

Simplified Kinetic Model for VFA Ketonization. The ketone product distribution was predicted using a simplified kinetic model for VFA ketonization at nearly 100% conversion of all the acids. The model was generalized for a reaction network of n-VFAs. Each unique VFA composition (including number of reactants, acid chain length, and acid concentration) is the model input and ketone distribution is model output. Reaction rate order of two was assumed since the rate limiting step of the acid ketonization was proposed to be the coupling of the two adsorbed acid molecules. The rate of a ketonization between two VFAs is described by Eqn. 1. The set of differential equations in Eqn. 2-4 was solved with ode45 in Matlab for the temporal profiles of the acids, ketones, $CO_2$ and $H_2O$ by products.

$$r_{ij} = k_{ij} C_{acid_i} C_{acid_j} \quad \text{(Eqn. 1)}$$

$$\frac{dC_{acid_i}}{dt} = \frac{dC_{acid_j}}{dt} = -r_{ij} \text{ If } i \neq j \quad \text{(Eqn. 2)}$$

$$\frac{dC_{acid_i}}{dt} = \frac{dC_{acid_j}}{dt} = -2r_{ij} \text{ If } i = j \quad \text{(Eqn. 3)}$$

$$\frac{dC_{ketone_{ij}}}{dt} = r \quad \text{(Eqn. 4)}$$

Whereas $k_{ij}$ is the rate constant of ketonization between $acid_i$ and $acid_j$, and $C_{acid}$ is the concentration (mol/L) of the acid reactant, $C_{ketone_{ij}}$ is the concentration of ketone product from reaction of $acid_i$ and $acid_j$. For each ketonization reaction, the amount of water or $CO_2$ formed is equal to that of the ketone. We assume that $k_{ij}=2 k_{ii}$. Because it has been reported that the rate constant for cross-ketonization ($i \neq j$) is double that for self-ketonization ($i=j$)

HDO Catalyst Synthesis. $Pt/Al_2O_3$ catalyst was prepared by strong electrostatic adsorption method with chloroplatinic acid hexahydrate as Pt precursor. $Al_2O_3$ of 30-50 mesh (crushed and sieved from Alfa Aesar $Al_2O_3$ pellets) and Pt precursor were added to deionized water, and solution pH was adjusted to 3 by adding HCl. After stirring overnight, the catalyst particles were recovered by filtration extensively washed with deionized water. The catalyst was dried in the air and reduced in flowing $H_2$ (200 mL min$^{-1}$) at 300° C. for 4 h prior to use.

Catalyst Characterization.

Physisorption. Nitrogen physisorption was performed using a Quadrasorb evo (Quantachrome). In a typical measurement, 0.10 g of catalyst was degassed under flowing He at 200° C. for 16 h. Full adsorption and desorption isotherms were recorded for each sample at −196° C. (77 K). Surface area was computed using the multi-point Brunauer-Emmett-Teller (BET) method, while pore volume and pore size distribution were determined using the Barrett, Joyner and Halenda (BJH) method for the desorption isotherm.

$NH_3$ temperature programmed desorption. Temperature programmed desorption (TPD) of $NH_3$ was performed using an Autochem II 2920 (Micromeritics) to measure catalyst acidity (FIG. S5). Approximately 0.10 g of catalyst was loaded into a quartz u-tube and supported by quartz wool. After purging the system with helium, the catalyst was pretreated by ramping to 120° C. for 1 h, then 500° C. for 2 h in flowing helium. After cooling to 120° C., a stream of premixed 10% $NH_3$ (balance helium) was passed over the catalyst for 1 h to saturate acidic sites on the catalyst surface. Following a 2-h helium purge at 120° C. to remove physisorbed $NH_3$, the sample temperature was ramped to 500° C. at 10° C. min$^{-1}$ in helium carrier gas at 50 cm3 (STP) min$^{-1}$, while $NH_3$ concentration in the effluent was monitored by a thermal conductivity detector (TCD). After calibrating the TCD, the desorption peak area was used to calculate the total quantity of acid sites by assuming a 1:1 stoichiometry of $NH_3$ binding to acid sites.

Pyridine diffuse reflectance Fourier transform infrared spectroscopy (DRIFTS). DRIFTS measurements were performed using a Thermo Nicolet iS50 FT-IR spectrometer equipped with a Harrick Praying Mantis reaction chamber. $ZrO_2$ samples were treated at 350° C. (5° C. min$^{-1}$ ramp) for 2 h under flowing $N_2$, cooled to 150° C. and purged with $N_2$ for 10 min before collecting a background spectrum. The samples were then dosed with pyridine vapor by flowing $N_2$ through a pyridine filled bubbler at room temperature for 5 min before removing physisorbed pyridine under $N_2$ by heating to 200° C. (5° C. min$^{-1}$ ramp) and holding for 30 min. The samples were cooled back to 150° C. and the spectra were collected by taking 64 scans at a resolution of 4 cm $N_2$. The background spectra were subtracted from the average spectra before identifying peaks associated with Brønsted and Lewis acid sites.

Thermal Gravimetric Analysis. The irreversibly adsorbed carbon amount of spent catalysts was measured by a Setaram Setsys Evolution thermal gravimetric analyzer (TGA) coupled with a Nicolet 6700 Fourier Transform InfraRed (FTIR) spectrometer via a transfer line heated at 200° C. The FTIR spectrometer is equipped with a gas cell maintained at 225° C. to prevent vapor condensation. The catalyst was heated to 800° C. under zero air (19-21% oxygen with a balance of nitrogen). The onset of carbon combustion was determined by the observation of carbon dioxide in the FTIR. Prior to the onset of carbon combustion, only water was observed in the FTIR spectra. Therefore, the carbon content was calculated by subtracting the mass loss due to water from the total mass loss recorded by the TGA.

Microscopy. Scanning transmission electron microscopy with energy dispersive X-ray spectroscopy (STEM-EDS) was used to reveal morphology and elemental distribution of fresh, spent and regenerated $ZrO_2$ catalyst (see FIG. 7). High resolution (HR)-STEM imaging was conducted utilizing an aberration-corrected a JEOL 2200FS STEM/TEM instrument equipped with a CEOS GmbH (Heidelberg, Ger) corrector on the illuminating lenses and operated at 200 kV. The MAG 7C mode was used to achieve a probe with a nominal 41 pA current and associated resolution of a nominal 0.07 nm. STEM-EDS was performed on FEI F200X Talos operating at 200 kV and equipped with an extreme field emission gun (X-FEG) electron source, high-angle annular dark-field (HAADF) detector and Super-X EDS system with 4 silicon-drift detectors (SDD) (Broker)(Flash® 6 series with detector size 120 mm$^2$) with a solid angle of 0.9 Steradian for chemical analysis. To avoid and/or decrease any potential electron beam damage during spectroscopy analysis but maintain high signal-to-noise ratio, the current of the electron beam was controlled and was set to 480 pA. For scanning transmission electron microscopy (STEM) analysis, the catalysts were drop-cast onto lacey carbon-coated copper grids (SPI Supplies part no. Z3820C) from isopropanol suspensions.

X-ray Photoelectron Spectroscopy (XPS). XPS was used to identify the elements that exist on the catalyst surface and to what elements they are bonded to as well as to identify their chemical state. The XPS analysis was performed using a Thermo Scientific K-Alpha XPS instrument using a 400-micron diameter x-ray spot. Three samples, fresh, spent and regenerated $ZrO_2$, were analyzed. The three powder samples were mounted for analysis by dispersing onto double-sided tape fixed to a clean glass slide. After insertion into the analysis chamber, a wide energy range survey scan was acquired to determine all elements present. Next, a set of narrow energy range core level spectra were acquired for each identified element. The survey data were acquired to obtain the overall surface composition for each sample (see Table 3). The surface compositions were determined using the core level data. Analysis also involved comparison of the C 1s, O 1s, and Zr 3d core level spectra for the three catalysts to identify the bonding. The C 1s showed at least four type of carbon bonding: C—C; C—O; O=C—O; and a small carbonate feature. O is also showed multiple bonding configurations: O—Zr; O=C, and O—C. The Zr 3d was a doublet having both Zr $3d_{5/2}$ and Zr $3d_{3/2}$ spin orbit split pairs. Two distinct forms of Zr were found in fresh $ZrO_2$; one at Zr $3d_{5/2}$~182 eV (assigned to $ZrO_2$) and one at Zr $3d_{5/2}$~183 eV, which is likely related to a surface hydroxide or carbonate. The Zr—O portion was dominant in the spent and regenerated $ZrO_2$.

Chemical Product Analysis:

Gas chromatography. Samples of liquid products were analyzed using gas chromatography on an Agilent 7890 GC system equipped with a Polyarc-flame ionization detector (Polyarc-FID) for quantifying concentrations and a mass spectrometer (MS, Agilent Technologies) for identifying products. The instrument utilized an HP-5MS column (30 m×0.25 4 mm), split injection (25:1), an injection volume of 1 µL, an inlet temperature of 260° C., ramped under a program (40° C. for 2 min, then 18° C. $min^{-1}$ to 280° C.), and helium as the carrier gas at 29 cm $sec^{-1}$. The eluent from the column was split into the Polyarc-FID and MS instruments for simultaneous measurements. The Polyarc (Advanced Research Company) device catalytically converts organic compounds into methane before traditional FID to allow for facile concentration measurements for several products in a sample based upon a single standard calibration curve.

Ketonization Flow Reactor:

Conversion, Mass Yield and Selectivity. VFA ketonization experiments were performed in a custom built trickle bed flow reactor (Parr) consisting of a mass flow controller (Brooks Instruments) for adjusting the flowrate the argon gas, a high-pressure liquid chromatography pump (Chromtech) for controlling liquid addition, a clamshell furnace for temperature control, a tube-in-tube heat exchanger for condensing liquids from the reactor effluent, and a knock-out pot for collecting liquid product mixtures. All ketonization reactions were performed at atmospheric pressure with no back-pressure regulation. The liquid and gas feeds mixed above the reactor tube (½" outer diameter, Dursan-coated stainless steel (SilcoTek Coating Co.) and flowed across the $ZrO_2$ catalyst bed (30-50 mesh, Johnson Matthey). Liquid samples were analyzed by GC while the effluent gas was analyzed by an online non-dispersive infrared detector for concentrations of $CO_2$, CO, $CH_4$ and $O_2$. Conversion, yield, and selectivity from the ketonization reactions were calculated using the following equations:

$$\text{Conversion} = \frac{Mol_{acid,in} - Mol_{acid,out}}{Mol_{acid,in}} \quad \text{(Eqn. 5)}$$

$$\text{Yield (mass \%)} = \frac{Mass_{product,out}}{(Mass_{acid,in})} * 100\% \quad \text{(Eqn. 6)}$$

$$\text{Selectivity (\%)} = \frac{Yield_{Ketones}}{(Yield_{Ketones} + Yield_{Non-targets})} * 100\% \quad \text{(Eqn. 7)}$$

Post-Ketonization Distillation:

The organic phase from the $C_4/C_6$ ketonization reaction was decanted from the aqueous phase and then distilled in a BR Instruments® Micro-distillation column to separate $\leq C_7$ ketones from $\geq C_8$ ketones. The BR Instruments® Micro-distillation column was run at 45 torr and heated at an initial rate of 10% and increased to 12.5% after the first few milliliters of distillate were collected. The reflux ratio was held at twenty until the first few milliliters of distillate were collected at which point the reflux ratio was decreased to five. The condenser circulating an 80:20 water to ethylene glycol mixture was held at 5° C. for the duration of the distillation. A Teflon band rotating 120 rpm was used in the column. The lighter ketones $\leq C_7$ were collected in the distillate from room temperature up to 160° C. and utilized for aldol condensation while the heavier ketones $\geq C_8$ were used for subsequent HDO process. This process removed all but 7% of $C_7$ ketones (and all measurable $C_4$-$C_6$ ketones) from the heavier fraction and approximately 21% of $C_5$-$C_9$ ketones distilled into the light fraction.

Ketonization Catalyst Regeneration:

Following 100 h testing with biogenic VFAs, the $ZrO_2$ catalyst was recovered from the reactor for further characterization and regeneration. Catalyst regeneration conditions were as follows: 5° C./min to 500° C., hold 12 h, cool naturally, in flowing air.

Ketone Aldol Condensation:

Ketone condensation experiments were performed in a Dean-Stark reactor system.

In a 500-mL round-bottom flask, 250 g feed (20 wt % ketone in decane) and 25 g niobic acid hydrate were mixed with a Teflon-coated magnetic stir bar. The flask was immersed in an oil bath heated by a hot plate set at 190° C. The reactor is open to atmosphere through a trap and a condenser. A small quantity of organics (decane and ketones) as well as water (a condensation product) were collected in the trap after cooled by the condenser operating at 4° C. Each experiment was conducted for 6-7 h, after which the reactor was cooled down naturally. Reaction mixture was filtered through 0.45-µm PTFE membranes to separate the liquid from the catalysts. Ketone conversion was summarized in Table 9. Due to the challenges with separating and identifying the enone products, enone yield and selectivity were not quantified. Instead, the mass yield of "upgradable" condensation products was measured from post-condensation distillation.

Post-Condensation Distillation:

The organic phase from the aldol condensation reaction was distilled in a BR Instruments® Micro-distillation column to remove unreacted ketones and solvent. The BR Instruments® Micro-distillation column was run at 50 torr and heated at an initial rate of 12.5% and increased to 17.5% after the first few milliliters of distillate were collected. The reflux ratio was held at 20 until the first few milliliters of distillate were collected at which point the reflux ratio was decreased to 2. The condenser circulating an 80:20 water to ethylene glycol mixture was held at 5° C. for the duration of the distillation. A monel band rotating 120 rpm was used in the column.

Mass Yield and Fraction Composition. The unreacted ketones and solvent fraction was collected in the distillate from room temperature up to 175° C. while the remaining were used for further HDO process. This left approximately 10 wt % of solvent in the fuel which theoretically could be removed but proved difficult in benchtop distillation without significant loss of product. It should also be noted that the unreacted ketones could be removed from the solvent for recycle to the aldol condensation reactor. The mass yield of the enone fraction is 41%. From a carbon content of 73.4% for the ketones and 80.7% for the enones, the C yield of the enone was calculated as 46%.

Hydrodeoxygenation Flow Reactor:

Hydrodeoxygenation experiments of ketone and enone sample mixtures were performed in a custom built trickle bed flow reactor consisting of a mass flow controller (Brooks Instruments) for adjusting the flowrate the hydrogen gas, a high-pressure liquid chromatography pump (Chromtech) for controlling liquid addition, a heat-traced inlet line for pre-heating the liquid/gas mixture, a clamshell furnace for temperature control of the reactor tube, a tubein-tube heat exchanger for condensing liquids from the reactor effluent, and a knock-out pot for collecting liquid product mixtures. A back-pressure regulator (Brooks Instruments) maintained the reactor at a pressure of 500 psig. The liquid and gas feeds mixed above the reactor tube (½" outer diameter, Dursan-coated stainless steel (SilcoTek Coating Co.)) and flowed across the Pt/Al$_2$O$_3$ catalyst bed (3 wt % Pt, synthesis procedure previously reported. Catalyst bed sizes were increased from our previous work to account for sulfur impurities in the VFA feeds and mitigate deactivation of the platinum sites using previously reported correction factors. Liquid samples were analyzed by GC/FID-MS and showed complete conversion with no remaining oxygenate molecules appearing by GC-MS.

Fuel Property Analysis:

The fuel properties of the VFA-SAF were estimated and measured using Tier α and β respectively. Tier α consists of using GCxGC and GC to conduct hydrocarbon type analysis and distillation curve testing, respectively. The results of this hydrocarbon type analysis is then used to produce property predictions which include density, surface tension, viscosity, cetane number (CN), net heat of combustion (nHOC), flash point, and freeze point. Tier β consists of measuring several key properties, and then using those measurements in combination with correlations to the combustion prediction figure of merit panels to predict likely outcomes of Tier 3 and Tier 4 testing. Table 1 details the testing volume required and ASTM method for each measurement, alongside properties predicted at each tier. Additional measurements described in the table were taken to supplement typical coverage of the Tier α and β testing.

Sooting Tendency Analysis:

Sooting tendency is a fuel property that can be measured at the laboratory scale but is intended to characterize the relative propensity of a fuel to cause soot emissions at the full device scale. In the aviation sector, sooting tendency is typically measured with the ASTM D1322 smoke point (SP) test. SP is determined with a specified wick burner and is defined as the height of the test fuel's flame that is at the threshold of emitting soot from its tip. SP is inversely related to sooting tendency: a sootier fuel will produce more soot for a given fuel flowrate and thus soot will break through the tip of the flame at a lower flowrate, which corresponds to a shorter flame. Studies have shown that sooting tendencies derived from 1/SP correlate with emissions from real aviation gas turbines.

However, SP has several disadvantages when applied to the development of SAF. First, it requires a relatively large amount of fuel: ASTM D1322 requires 10 mL and recommends 20 mL. These volumes are necessary to fully saturate the wick and create a steady-state system, so they cannot be reduced. Second, SP has a narrow dynamic range and cannot be directly applied to fuels whose sooting characteristics differ significantly from Jet A, especially fuels such as SAF that have lower sooting tendencies. The upper limit to the SP that can be measured with the ASTM D1322 apparatus is ~50 mm, which prevents direct measurements for the normal paraffins that dominate the Fast Track VFA-SAF. The SP of n-dodecane, which is near the center of the carbon number distribution for Fast Track VFA-SAF, has been determined by indirect means to be ~60 mm.

Therefore, in this study we characterized sooting tendency using a newer approach we have developed that is based on measurements of soot yield in doped methane flames. The fundamental concept is to add a small amount of the test fuel (~1000 ppm) to the fuel of a methane/air flame, and then measure the resulting soot concentration. Since the dopant concentration is small, only a small volume of fuel is required (<100 μL per measurement). Furthermore, the dynamic range is large since the method depends on a quantitative soot measurement—instead of the subjective choice of the threshold where soot is emitted from a wick burner flame—and the dopant concentration can be varied to suit different fuels. Indeed, we have successfully applied this approach to hydrocarbons ranging in sooting tendency from methanol (a C1 oxygenated hydrocarbon) to pyrene (a four-ring polycyclic aromatic hydrocarbon). We have shown that the results with this new approach correlate with SP for conventional aviation fuels, and independent researchers have reached a similar conclusion.

The specific methodology used in the current study was modified to suit SAF. Our earlier work focused on pure hydrocarbons. They were added to the flame at a fixed mole fraction and the resulting soot yield was rescaled into a yield sooting index (YSI) relative to two endpoint compounds with defined values. The current study involves real fuel mixtures, which have a complex composition such that the molecular weight is not know precisely, so they cannot be added to the flame on a mole fraction basis. Instead, they were added at a fixed liquid-phase volumetric flowrate (1000 μL/h). Furthermore, the measured soot yields were not rescaled relative to endpoint species but instead they were normalized to the soot yield for the POSF 10325 Jet A sample described in Table 7.

Whether or not a reactant or product described herein is "bioderived" may be determined by analytical methods. Using radiocarbon and isotope ratio mass spectrometry analysis, the bio-based content of materials can be determined. ASTM International, formally known as the American Society for Testing and Materials, has established a standard method for assessing the biobased content of carbon-containing materials. The ASTM method is designated ASTM-D6866. The application of ASTM-D6866 to derive a "biobased content" is built on the same concepts as radiocarbon dating, but without use of the age equations. The analysis is performed by deriving a ratio of the amount of radiocarbon (14C) in an unknown sample to that of a modern reference standard. The ratio is reported as a percentage with the units "pMC" (percent modern carbon). If the material being analyzed is a mixture of present-day radiocarbon and fossil carbon (containing no radiocarbon), then the pMC value obtained correlates directly to the amount of biomass material present in the sample. Thus, ASTM-D866 may be used to validate that the compositions described herein are and/or are not derived from renewable sources.

FURTHER EXAMPLES

1 Method Examples—Carboxylic Acids to Paraffins

Example 1. A method comprising: a first treating of a first mixture comprising a carboxylic acid having between 2 and 12 carbon atoms, inclusively, to form a second mixture comprising a ketone having between 2 and 25 carbon atoms, inclusively; and a second treating of at least a first portion of the second mixture to form a first product comprising a paraffin having 8 or more carbon atoms.

Example 2. The method of Example 1, wherein the carboxylic acid has between 2 and 8 carbon atoms, inclusively.

Example 3. The method of Example 1, wherein the ketone has between 3 and 15 carbon atoms, inclusively.

Example 4. The method of Example 1, wherein: the first treating comprises the reaction

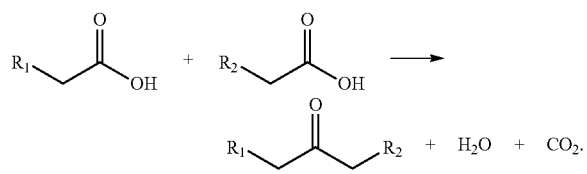

$R_1$ comprises between 1 and 11 carbon atoms, and $R_2$ comprises between 1 and 11 carbon atoms.

Example 5. The method of Example 1, wherein the first treating is performed at a temperature between about 325° C. and about 450° C.

Example 6. The method of Example 5, wherein the temperature is between about 325° C. and about 375° C.

Example 7. The method of Example 1, wherein the first treating is performed at a pressure between about 0 psig and about 250 psig.

Example 8. The method of Example 7, wherein the pressure is between about 0 psig and about 10 psig.

Example 9. The method of Example 1, wherein the first mixture further comprises at least one of $H_2$ gas or an inert gas.

Example 10. The method of Example 1, wherein the first mixture further comprises water.

Example 11. The method of Example 10, wherein the water is present at a concentration between greater than 0 wt % and about 25 wt %.

Example 12. The method of Example 1, wherein the first treating is performed in the presence of a catalyst comprising a metal oxide.

Example 13. The method of Example 12, wherein the metal oxide comprises at least one of zirconium, titanium, or niobium.

Example 14. The method of Example 13, further comprising a transition metal.

Example 15. The method of Example 14, wherein the transition metal comprises at least one of platinum, palladium, ruthenium, nickel, cobalt, or molybdenum.

Example 16. The method of Example 12, wherein the catalyst comprises a solid in a form comprising at least one of a powder or a pellet.

Example 17. The method of Example 16, wherein the solid has a surface area between about 25 $m^2/g$ and about 250 $m^2/g$.

Example 18. The method of Example 17, wherein the surface area is between about 180 $m^2/g$ and about 220 $m^2/g$.

Example 19. The method of Example 16, wherein the solid has a total acidity between about 100 umol/g and about 400 umol/g.

Example 20. The method of Example 19, wherein the total acidity is between about 210 umol/g and about 260 umol/g.

Example 21. The method of Example 19, wherein the total acidity is due substantially to Lewis acid sites.

Example 22. The method of Example 16, wherein the first treating is performed in a packed bed reactor at a WHSV between about 1 $h^{-1}$ and about 10 $h^{-1}$.

Example 23. The method of Example 22, wherein the WHSV is between about 4 $h^{-1}$ and about 8 $h^{-1}$.

Example 24. The method of Example 1, wherein the second treating results in the deoxygenation of at least a portion of the ketone to form the paraffin.

Example 25. The method of Example 1, wherein the second treating is performed at a temperature between about 250° C. and about 450° C.

Example 26. The method of Example 25, wherein the temperature is between about 300° C. and about 370° C.

Example 27. The method of Example 1, wherein the second treating is performed at a pressure between about 0 psig and about 1500 psig.

Example 28. The method of Example 27, wherein the pressure is between about 400 psig and about 600 psig.

Example 29. The method of Example 1, wherein the second mixture further comprises water.

Example 30. The method of Example 29, wherein the water is present at a concentration between greater than 0 wt % and about 25 wt %.

Example 31. The method of Example 1, wherein the second treating is performed in the presence of a catalyst comprising a metal oxide.

Example 32. The method of Example 31, wherein the metal oxide comprises at least one of zirconium, titanium, niobium, aluminum, or silicon.

Example 33. The method of Example 32, further comprising at least one of a transition metal or sulfur.

Example 34. The method of Example 33, wherein the transition metal comprises at least one of platinum, palladium, ruthenium, nickel, cobalt, or molybdenum.

Example 35. The method of Example 30, wherein the catalyst comprises a solid in a form comprising at least one of a powder or a pellet.

Example 36. The method of Example 35, wherein the solid has a surface area between about 25 $m^2/g$ and about 550 $m^2/g$.

Example 37. The method of Example 36, wherein the surface area is between about 180 $m^2/g$ and about 220 $m^2/g$.

Example 38. The method of Example 35, wherein the solid has a total acidity about 100 umol/g and about 400 umol/g.

Example 39. The method of Example 38, wherein the total acidity is between about 300 umol/g and about 360 umol/g.

Example 40. The method of Example 39, wherein the total acidity is due substantially to Lewis acid sites.

Example 41. The method of Example 35, wherein the second treating is performed in a packed bed reactor at a WHSV between about 1 $h^{-1}$ and about 10 $h^{-1}$.

Example 42. The method of Example 41, wherein the WHSV is between about 4 $h^{-1}$ and about 8 $h^{-1}$.

Example 43. The method of Example 1, wherein the paraffin comprises a normal paraffin.

Example 44. The method of Example 43, wherein the normal paraffin has between 8 and 15 carbon atoms, inclusively.

Example 45. The method of Example 44, wherein the first product further comprises a cetane number between about 45 and about 70.

Example 46. The method of Example 44, wherein the first product further comprises a lower heating value between about 30 MJ/L and about 40 MJ/L, inclusively.

Example 47. The method of Example 1, wherein at least a portion of the carboxylic acid is bioderived as determined by ASTM-D6866.

Example 48. The method of Example 47, wherein the portion of the carboxylic acid is derived from a waste stream comprising at least one of a food processing waste or a water having a high organic content.

Example 49. The method of Example 48, wherein the waste stream comprises at least one of a municipal food waste, an animal manure, or a waste water sludge.

Example 50. The method of Example 48, wherein the waste stream comprises at least one an oil, a fat, a grease, or a pretreated lignocellulosic biomass.

Example 51. The method of Example 1, further comprising, prior to the second treating: separating the second mixture to form the first portion of the second mixture and a second portion of the second mixture, wherein: the first portion comprises a ketone having 8 or more carbon atoms, and the second portion comprises a ketone having less than 8 carbon atoms.

Example 52. The method of Example 51, wherein the separating is performed by distilling the second mixture.

Example 53. The method of Example 51, wherein the first portion further comprises a ketone having less than 8 carbon atoms at a concentration less than 1 wt %.

Example 54. The method of Example 51, further comprising: a third treating of the second portion to form a third mixture comprising an intermediate, wherein: the third treating comprises the reaction

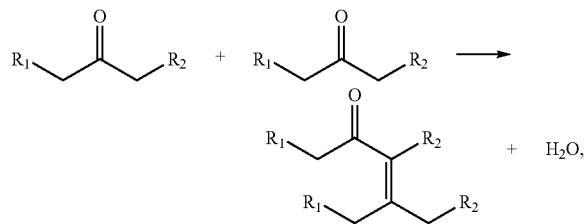

resulting in the forming of the intermediate and water, $R_1$ comprises between 1 and 6 carbon atoms, inclusively, $R_2$ comprises between 1 and 6 carbon atoms, inclusively, and the intermediate has a form comprising at least one of a linear molecule, a branched molecule, or a cyclic molecule.

Example 55. The method of Example 54, further comprising a fourth treating of at least a portion of the third mixture to form a second product comprising a paraffin having 10 or more carbon atom.

Example 56. The method of Example 55, wherein the paraffin of the second product comprises a branched paraffin.

Example 57. The method of Example 55, wherein the fourth treating results in the deoxygenation of at least a portion of the intermediate to form the paraffin.

Example 58. The method of Example 55, wherein the fourth treating is performed at conditions similar to those of the second treating.

Example 59. The method of Example 55, wherein the fourth treating and the second treating are performed in a single reactor.

Example 60. The method of Example 55, wherein the second product further comprises a cetane number between about 50 and about 85.

Example 61. The method of Example 55, wherein the second product further comprises a lower heating value between about 30 MJ/L and about 40 MJ/L, inclusively.

Example 62. The method of Example 55, further comprising mixing at least a portion of the first product with at least a portion of the second product to form a blended product.

Example 63. The method of Example 54, further comprising co-feeding the second mixture and the third mixture with at least one of a fat, an oil, or a grease to a deoxygenation step.

2 Method Examples—Secondary Alcohols to Paraffins

Example 1. A method comprising: a first reacting of a secondary alcohol resulting in the conversion of at least a portion of the secondary alcohol to an alkene; a second reacting of the alkene resulting in the conversion of at least a portion of the alkene to a branched alkene; and a third reacting of the branched alkene resulting the conversion of at least a portion of the branched alkene to a branched paraffin.

Example 2. The method of Example 1, wherein the first reacting is performed in a packed bed reactor.

Example 3. The method of Example 1, wherein the first reacting is performed at a temperature between about 100° C. and about 300° C.

Example 4. The method of Example 1, wherein the first reacting is performed at a pressure between about 1 atm and about 10 atm.

Example 5. The method of Example 1, wherein the first reacting is catalyzed using an acidic solid catalyst.

Example 6. The method of Example 5, wherein the acidic solid catalyst comprises an ion-exchange resin.

Example 7. The method of Example 1, wherein the second reacting is performed in a packed bed reactor.

Example 8. The method of Example 1, wherein the second reacting is performed at a temperature between about 100° C. and about 300° C.

Example 9. The method of Example 1, wherein the second reacting is performed at a pressure between about 10 atm and about 100 atm.

Example 10. The method of Example 1, wherein the second reacting is catalyzed using an acidic solid catalyst.

Example 11. The method of Example 10, wherein the acidic solid catalyst comprises an ion-exchange resin.

Example 12. The method of Example 1, wherein the third reacting is performed in a packed bed reactor.

Example 13. The method of Example 1, wherein the third reacting is performed at a temperature between about 100° C. and about 250° C.

Example 14. The method of Example 1, wherein the third reacting is performed at a pressure between about 10 atm and about 100 atm.

Example 15. The method of Example 1, wherein the third reacting is catalyzed using a solid catalyst comprising a transition metal positioned on a metal oxide support.

Example 16. The method of Example 1, further comprising, prior to the first reacting, converting a ketone to the secondary alcohol.

3 Composition Examples—Fast Track

Example 1. A composition for a liquid fuel, the composition comprising: a normal paraffin having more than 7 carbon atoms, wherein: the normal paraffin is bioderived, and the composition is characterized by at least one of a physical property or a performance metric that is improved compared to the same physical property or the same performance metric of a reference petroleum-based liquid fuel.

Example 2. The composition of Example 1, wherein the reference petroleum-based liquid fuel comprises diesel fuel or jet fuel.

Example 3. The composition of Example 1, wherein the normal paraffin is derived from a volatile fatty acid.

Example 4. The composition of Example 1, wherein the at least one of the physical property or the performance metric comprises at least one of a cetane value, a lower heating value (LHV), a normalized soot concentration, a surface tension, or a density.

Example 5. The composition of Example 4, wherein the composition has a cetane value between about 45 and about 70, inclusively.

Example 6. The composition of Example 4, wherein the composition has a LHV between about 30 MJ/L and about 40 MJ/L, inclusively.

Example 7. The composition of Example 4, wherein the normalized soot concentration is between less than 1.0 and greater than 0.50.

Example 8. The composition of Example 4, wherein the surface tension is between about 23.0 mN/m and about 26.0 mN/m, inclusively.

Example 9. The composition of Example 4, wherein the density is between about 0.7 g/cm3 and about 0.81 g/cm3, inclusively.

Example 10. The composition of Example 4, wherein the normal paraffin has between 8 and 15 carbon atoms, inclusively.

4 Composition Examples—Aldol Condensation

Example 1. A composition for a liquid fuel, the composition comprising: an iso-paraffin having more than 7 carbon atoms, wherein: the iso-paraffin is bioderived.

Example 2. The composition of Example 1, wherein the iso-paraffin has more than 9 carbon atoms.

Example 3. The composition of Example 2, wherein: the iso-paraffin comprises the structure

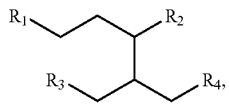

$R_1$ comprises a hydrocarbon having between 1 and 6 carbon atoms, inclusively, $R_2$ comprises a hydrocarbon having between 1 and 6 carbon atoms, inclusively, $R_3$ comprises a hydrocarbon having between 1 and 6 carbon atoms, inclusively, and $R_4$ comprises a hydrocarbon having between 1 and 6 carbon atoms, inclusively.

Example 4. The composition of Example 1, wherein the iso-paraffin is derived from a volatile fatty acid.

Example 5. The composition of Example 1, wherein the composition is characterized by at least one of a physical property or a performance metric comprising at least one of a cetane value, a lower heating value (LHV), a normalized soot concentration, a surface tension, or a density.

Example 6. The composition of Example 5, wherein the composition has a cetane value between about 45 and about 80, inclusively.

Example 7. The composition of Example 5, wherein the composition has a LHV between about 30 MJ/L and about 40 MJ/L, inclusively.

Example 8. The composition of Example 5, wherein the normalized soot concentration is between less than 1.0 and greater than 0.50.

Example 9. The composition of Example 5, wherein the surface tension is between about 23.0 mN/m and about 26.0 mN/m, inclusively.

Example 10. The composition of Example 5, wherein the density is between about 0.70 g/cm$^3$ and about 0.81 g/cm$^3$, inclusively.

Example 11. The composition of Example 1, wherein the iso-paraffin comprises at least one of 5-methylundecane, 3-ethyl-4-methylheptane, 5-ethyl-4-propylnonane, or 5-butyl-6-propyldecane.

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A method comprising:
   reacting a mixture of carboxylic acids to form a first mixture comprising ketones;
   separating the first mixture to form a second mixture comprising ketones having eight or more carbon atoms and a third mixture comprising ketones having less than eight carbon atoms; and
   a first treating of at least a portion of the second of the second mixture to form a first product comprising a paraffin having 11 carbon atoms, wherein:
   the reacting comprises

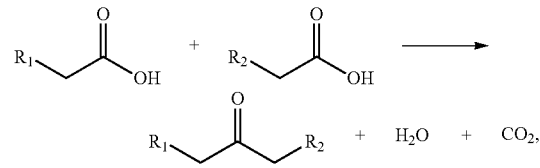

$R_1$ comprises between 1 and 11 carbon atoms, inclusively, and
   $R_2$ comprises between 1 and 11 carbon atoms, inclusively.

2. The method of claim 1, wherein:
   the carboxylic acids in the mixture of carboxylic acids have between 2 and 8 carbon atoms, inclusively.

3. The method of claim 1, wherein the ketones in the first mixture have between 3 and 15 carbon atoms, inclusively.

4. The method of claim 1, wherein the first treating results in the deoxygenation of at least a portion of the ketones having eight or more carbon atoms to form the paraffin.

5. The method of claim 1, wherein:
   the first product comprises a plurality of paraffins, and each paraffin has between 8 and 15 carbon atoms, inclusively.

6. The method of claim 5, wherein the plurality of paraffins comprise normal paraffins.

7. The method of claim 1, wherein at least a portion of the first mixture is bioderived as determined by ASTM-D6866.

8. The method of claim 1, further comprising:
a second treating of the third mixture to form a fourth mixture comprising an intermediate, wherein:
the second treating comprises the reaction

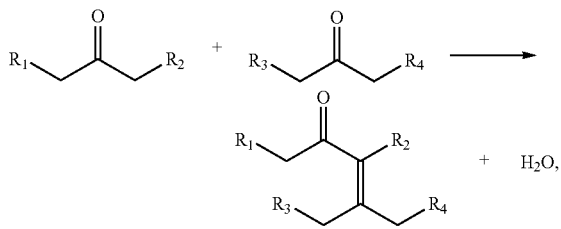

resulting in the forming of the intermediate and water,
$R_1$ comprises between 1 and 6 carbon atoms, inclusively,
$R_2$ comprises between 1 and 6 carbon atoms, inclusively,
$R_3$ comprises between 1 and 6 carbon atoms, inclusively,
$R_4$ comprises between 1 and 6 carbon atoms, inclusively, and
the intermediate has a form comprising at least one of a linear molecule, a branched molecule, or a cyclic molecule.

9. The method of claim 8, further comprising a third treating of at least a portion of the fourth mixture to form a second product comprising a paraffin having 10 or more carbon atoms.

10. The method of claim 9, wherein the paraffin of the second product comprises a branched paraffin.

11. The method of claim 9, wherein the third treating results in the deoxygenation of at least a portion of the intermediate to form the paraffin of the second product.

12. The method of claim 9, further comprising mixing at least a portion of the first product with at least a portion of the second product to form a blended product.

13. The method of claim 8, further comprising co-feeding at least a portion of at least one of the second mixture or the fourth mixture with at least one of a fat, an oil, or a grease to a deoxygenation step.

14. The method of claim 13, wherein the deoxygenation step is performed by at least one of the first treating or the third treating.

* * * * *